(12) United States Patent
Yeung et al.

(10) Patent No.: US 10,959,666 B2
(45) Date of Patent: Mar. 30, 2021

(54) WEARABLE HIP JOINT-ACTION DETECTORS

(71) Applicants: King-Wah Walter Yeung, Cupertino, CA (US); Wei-Wei Vivian Yeung, Cupertino, CA (US)

(72) Inventors: King-Wah Walter Yeung, Cupertino, CA (US); Wei-Wei Vivian Yeung, Cupertino, CA (US)

(73) Assignee: ENBIOMEDIC, Cupertino, CA (US)

( * ) Notice: Subject to any disclaimer, the term of this patent is extended or adjusted under 35 U.S.C. 154(b) by 1339 days.

(21) Appl. No.: 14/963,136

(22) Filed: Dec. 8, 2015

(65) Prior Publication Data

US 2016/0198995 A1 Jul. 14, 2016

Related U.S. Application Data

(60) Provisional application No. 62/102,494, filed on Jan. 12, 2015.

(51) Int. Cl.
*A61B 5/00* (2006.01)
*A61B 5/11* (2006.01)

(52) U.S. Cl.
CPC .......... *A61B 5/4528* (2013.01); *A61B 5/1116* (2013.01); *A61B 5/1118* (2013.01); *A61B 5/1128* (2013.01); *A61B 5/6823* (2013.01); *A61B 5/6826* (2013.01); *A61B 2562/0219* (2013.01); *A61B 2562/0257* (2013.01)

(58) Field of Classification Search
CPC ...................................................... A61B 5/11
See application file for complete search history.

(56) References Cited

U.S. PATENT DOCUMENTS

| 4,651,446 | A | 3/1987 | Yukawa | |
|---|---|---|---|---|
| 6,005,548 | A | 12/1999 | Latypov | |
| 6,491,647 | B1 * | 12/2002 | Bridger | A61B 5/021 128/900 |
| 7,463,997 | B2 | 12/2008 | Pasolini | |
| 8,050,881 | B1 * | 11/2011 | Yeung | A61B 5/0024 370/503 |
| 8,165,844 | B2 | 4/2012 | Luinge | |
| 2013/0312168 | A1 * | 11/2013 | Raanan | A41D 13/0506 2/465 |

(Continued)

*Primary Examiner* — Daniel L Cerioni
*Assistant Examiner* — Yasmeen S Warsi

(57) ABSTRACT

An activity detector worn on or in the vicinity of the waist detects hip-joint actions of the user, by using a proximity sensor in the activity detector to sense the separation between the activity detector housing and a body target linked by the hip joint. For example, when the housing of an activity detector adjacent to the lower abdomen incorporates one or more sensing plates of a capacitive proximity sensor, flexion, extension, abduction, or adduction of the hip joint can be detected as the separation between the sensing plates and the lower abdomen changes. Besides the lower abdomen, alternative body targets include the thigh, buttocks, etc. Besides capacitive proximity sensors, alternative proximity sensors include active infrared proximity sensors, imaging sensors, etc. The activity detector can also incorporate an accelerometer to obtain additional movement and orientation data, which can be combined with the separation data to detect more complex activities.

25 Claims, 14 Drawing Sheets

(56) References Cited

U.S. PATENT DOCUMENTS

2014/0074431 A1 3/2014 Modi
2014/0200496 A1* 7/2014 Hyde .................. A61F 5/02
                                                602/19

* cited by examiner

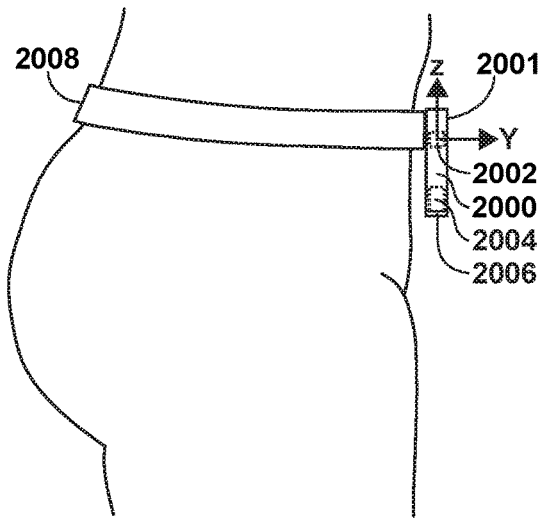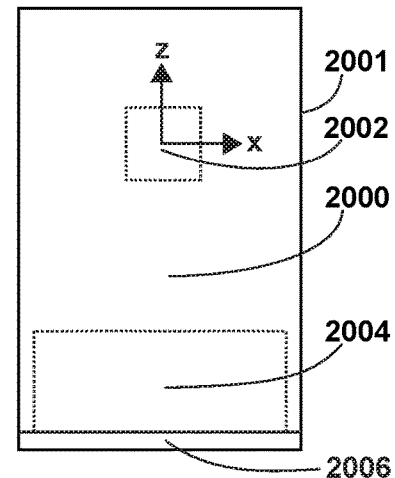
FIG. 20AFIG. 20B
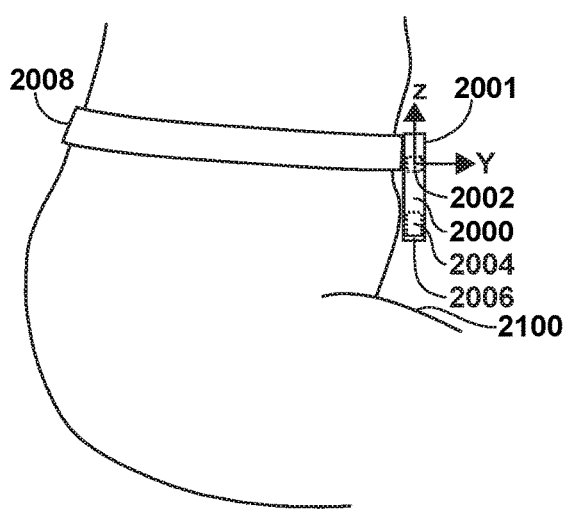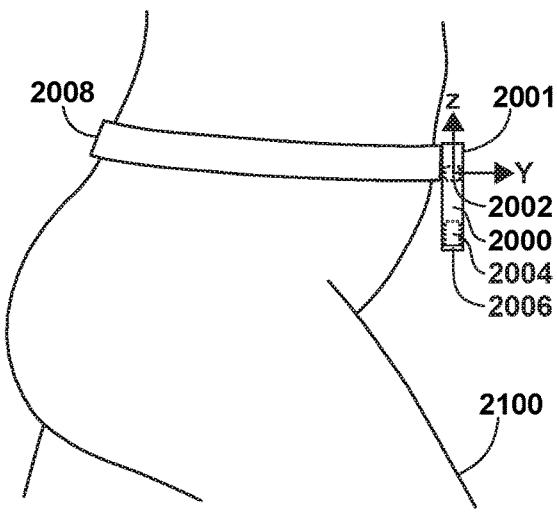
FIG. 21AFIG. 21B

WEARABLE HIP JOINT-ACTION DETECTORS

CROSS-REFERENCE TO RELATED APPLICATIONS

This application claims the benefit of provisional application Ser. No. 62/102,494, filed 2015 Jan. 12 by the present inventors.

BACKGROUND

Prior Art

Physical activity is one of the most important factors in reducing the risk of obesity, cardiovascular disease, diabetes, metabolic syndrome, colon cancer, breast cancer, and depression. In addition, a recent study shows that prolonged sitting is linked to higher risk of death from heart disease and other causes, even if a person gets regular exercise. Pedometers are commonly used to monitor physical activity, and are usually worn on the waist, wrist, or foot of a user. A modern pedometer typically incorporates an accelerometer to detect body vibrations for counting steps as a user walks or runs, but cannot detect other types of physical activity. For example, we have found that a pedometer cannot reliably distinguish between sitting and standing, because a user is stationary in both cases. We have also found that a pedometer might mistakenly count steps when a user's body vibrates on a traveling vehicle, or when a user steers a vehicle while wearing a wrist-worn pedometer.

U.S. Pat. No. 7,463,997 (2008) to Pasolini et al. discloses a step-detection algorithm for a pedometer incorporating an accelerometer carried by a user, such as on the user's belt or shoulder. U.S. patent application Pub. No. 2014/0074431 (2014) by Modi discloses step-detection optimizations for a pedometer incorporating an accelerometer worn on a user's wrist. The challenges of detecting steps reliably by using the accelerometer data of a pedometer are discussed in these two publications.

U.S. Pat. No. 4,651,446 (1987) to Yukawa et al. discloses a pedometer that uses a step sensor mounted on the instep of footwear for detecting the flexing motion of the instep as a user walks or runs. The step sensor can be a strain transducer, a piezoelectric element, or simply a switch which closes during the flexing motion of the instep. Although this pedometer can detect steps reliably without suffering interference from body vibrations not related to walking or running, it still cannot detect whether a user is sitting, standing, or performing any type of physical activity other than walking and running. Furthermore, we have found that this type of step sensor would not be very reliable and durable because of wear and tear of the mechanical parts after repeated use.

U.S. Pat. No. 6,005,548 (1999) to Latypov et al. discloses a method for tracking a user's spatial position and orientation by placing a sensor of relative rotation angles at each of the main joints of the user, such as the hip, knee, shoulder, and elbow joints. This sensor of relative rotation angles of a joint is a strain gauge or an optical-fiber sensor, which is physically attached to the body segments connected by the joint. Although this method can detect many types of physical activity performed by a user, physically attaching a sensor of rotation angles to two body segments connected by a joint is inconvenient and cumbersome.

U.S. Pat. No. 8,165,844 (2012) to Luinge et al. discloses a system for capturing motion of a human body by placing a wireless sensor module on each body segment. Each sensor module contains accelerometers and gyroscopes for collecting three-dimensional inertial data, and optionally magnetometers for sensing the earth's magnetic field. Although this method can detect any physical activity, the relatively complex system requires placing a sensor module on each of the two body segments linked by a joint for determining the degree of flexion of the joint. The system is too complicated and costly for detecting common physical activities such as walking, running, sitting, and standing, so it is not practical for widespread use.

The basic element of any physical activity is a joint action, which also includes the degree of the joint action in this description. A joint action is any movement of a joint that is allowed by the anatomy of the joint, such as flexion, extension, abduction, adduction, internal rotation, or external rotation. For this reason, a physical activity performed by a human being or an animal can be determined by detecting the joint actions of the joints (simply called actions of the joints in this description) that are involved in the physical activity. However, the aforementioned prior-art approaches for monitoring physical activities either do not detect joint actions or use complicated devices for detecting joint actions. In short, they suffer from a number of disadvantages:

(a) Accelerometer-based pedometers might mistakenly count steps when a user's body vibrates.

(b) A current physical-activity monitor, such as a pedometer, worn on the waist, wrist, or foot of a user, can only detect that the user is walking or running, but not any other type of physical activity, such as sitting or standing.

(c) Current joint-action sensors that can detect a user performing a physical activity by sensing the actions of the joints involved in the physical activity are inconvenient, cumbersome, and costly, so they are not practical for widespread use.

For improving and simplifying physical-activity monitoring, U.S. Pat. No. 8,050,881 (2011) to Yeung et al. (the same inventors of the present invention) discloses a physical-activity monitoring system that incorporates only three sensors on the body of a user. The sensors are accelerometers worn on the wrist, waist, and thigh (the accelerometer worn on the thigh is for improving detection of physical activities of the lower extremities) of a user. The accelerometers are used for monitoring the orientations and movements of the body segments of a user to detect the type and intensity of physical activity performed. The accelerometers on the wrist are useful in detecting activities involving the upper extremities. The degree of flexion of the hip joint can be determined from the orientations of the waist and thigh with respect to the vertical direction of the earth's gravitational acceleration, so that stationary activities, such as standing and sitting, can be detected. The waist and thigh accelerometers can also detect more rigorous activities, such as walking, running, or jumping, from simultaneous, fast-changing accelerations. However, we have found that it would be a major improvement in usability for the physical-activity monitoring system if the sensor worn on the thigh were not required for detecting actions of the hip joint.

SUMMARY

In accordance with a first embodiment of a wearable joint-action sensor, the sensor comprises a capacitive proximity sensor that is worn on the right waist of the torso of a user, above the right thigh of the right upper leg, for detecting flexion and extension of the right hip joint, without requiring the user to attach a sensor to the right thigh. The capacitive proximity sensor detects the amount of separation between the capacitive proximity sensor and the right abdomen of the torso above the right thigh as the right hip joint is flexed or extended. Based on the amount of separation and its rate of change, the wearable joint-action sensor can detect actions of the right hip joint of the user, such as walking, running, sitting, and standing.

In accordance with a second embodiment of a wearable joint-action sensor, the sensor comprises a capacitive proximity sensor that is worn on the right shoulder of the torso of a user and attached with a shoulder pad. The capacitive proximity sensor detects the amount of separation between the capacitive proximity sensor and the region comprising both the right shoulder and the top of the right upper arm, as the right shoulder joint is abducted or adducted. Any other action of the right shoulder joint, such as flexion or extension, can be detected by placing an additional sensing plate of the capacitive proximity sensor on the shoulder pad, where the capacitive proximity sensor can detect the amount of separation between the sensing plate of the capacitive proximity sensor and the region comprising both the right shoulder and the top of the right upper arm, as the right shoulder joint performs the action. Based on the amount of separation and its rate of change, the wearable joint-action sensor can detect actions of the right shoulder joint of the user, such as swinging, lifting, jumping rope, and pushing up.

In accordance with a third embodiment of a wearable joint-action sensor, the sensor comprises a capacitive proximity sensor that is worn on the wrist region of the right forearm of a user. The capacitive proximity sensor detects the amount of separation between the capacitive proximity sensor and the wrist regions of the right forearm and the right hand as the right wrist joint is flexed or extended. Based on the amount of separation and its rate of change, the wearable joint-action sensor can detect actions of the right wrist joint, such as waving, pushing, and slapping.

In accordance with a fourth embodiment of a wearable joint-action sensor, the sensor comprises a capacitive proximity sensor that is mounted on the instep of the right footwear that is worn by a user. The capacitive proximity sensor detects the amount of separation between the capacitive proximity sensor and the instep of the right foot as the right ankle joint is flexed (plantar flexion) or extended (dorsiflexion). Based on the amount of separation and its rate of change, the wearable joint-action sensor can detect actions of the right ankle joint, such as kicking, tip toeing, walking, and running.

In accordance with a fifth embodiment of a wearable joint-action sensor, the sensor comprises a capacitive proximity sensor that is worn on the right upper arm of a user above the elbow. The capacitive proximity sensor detects the amount of separation between the capacitive proximity sensor and the right upper arm above the elbow pit (antecubital fossa) as the right elbow joint is flexed or extended. Based on the amount of separation and its rate of change, the wearable joint-action sensor can detect actions of the right elbow joint, such as lifting, stretching, and punching.

In accordance with a sixth embodiment of a wearable joint-action sensor, the sensor comprises a capacitive proximity sensor that is worn on the first finger segment of the right index finger of a user. The capacitive proximity sensor detects the amount of separation between the capacitive proximity sensor and a region comprising both the first and second segments of the right index finger near the first finger joint (the proximal interphalangeal joint) as the first finger joint is flexed or extended. Based on the amount of separation and its rate of change, the wearable joint-action sensor can detect actions of the first finger joint of the right index finger, such as typing, flicking, and pointing.

In accordance with a seventh embodiment of a wearable joint-action sensor, the sensor comprises a capacitive proximity sensor that is worn on top of two adjacent sections of the upper spinal column of a user. The capacitive proximity sensor detects the amount of separation between the capacitive proximity sensor and a region comprising the two adjacent sections of the upper spinal column as the upper spinal column is flexed or extended. Based on the separation and its rate of change, the wearable joint-action sensor can detect actions of the upper spinal column, such as flexion and extension. The wearable joint-action sensor can inform the user of poor posture because of excessive flexion of the upper spinal column by activating a reminder to produce vibration, sound, voice, display, or light.

In accordance with an eighth embodiment of a wearable joint-action sensor, the sensor comprises an active infrared proximity sensor (or a visible- or infrared-light imaging sensor) and a triaxial accelerometer that is worn on the right waist of the torso of a user above the right thigh of the right upper leg. By using four infrared-light sources, the active infrared proximity sensor detects the amount of separation between the active infrared proximity sensor and the right thigh of the right upper leg, and the amount of deviation of the right thigh from the midline of the active infrared proximity sensor. Based on the amount of separation and the amount of deviation of the right thigh from the midline of the active infrared proximity sensor, and its rates of change, the wearable joint-action sensor can detect actions of the right hip joint and many types of physical activity, such as walking, running, sitting, standing, and dancing. Furthermore, by combining the joint actions detected by using the active infrared proximity sensor and the body actions detected by using the triaxial accelerometer, the wearable joint-action sensor can detect additional types of physical activity, such as jumping, somersaulting, sitting up, pushing up, and biking.

In addition to being used for detecting many types of physical activity, a wearable joint-action sensor can be used for controlling a computing device or for serving as a reminder as follows. When a wearable joint-action sensor uses a communication device to communicate with a computing device, such as a smartwatch, fitness wristband, smartphone, or computer, a joint action detected by the wearable joint-action sensor can be used for controlling the computing device, such as turning a display on or off, turning an audio recorder on or off, playing back a recorded audio message, or receiving or terminating a phone call. Furthermore, multiple wearable joint-action sensors, each used for detecting actions of a joint (such as a finger joint, wrist joint, toe joint, or ankle joint), can communicate with a computing device, such as an electronic piano (or any electronic music instrument), electronic game console, or computer, to perform complex operations of the computing device. A wearable joint-action sensor can also communicate with a reminder, such as a voice recorder, vibrator, beeper, display, or simply a light-emitting diode (LED), to remind a user or someone else (such as a caregiver of the user) that a predetermined desirable or undesirable joint action is or has been detected.

DRAWINGS

Figures

FIG. 20A is a graphical illustration of a possible location of a wearable joint-action sensor incorporating an active infrared proximity sensor and a triaxial accelerometer for detecting actions of the right hip joint of a user in accordance with the eighth embodiment.

FIG. 20B is a front view (the surface that faces the right abdomen of the user) of the wearable joint-action sensor in FIG. 20A.

FIG. 21A is a graphical illustration of the separation between the active infrared proximity sensor and the right thigh, and the orientation of the triaxial accelerometer, as the right hip joint of the user in FIG. 20A is flexed.

FIG. 21B is a graphical illustration of an increase in the amount of separation between the active infrared proximity sensor and the right thigh, and the orientation of the triaxial accelerometer, as the degree of flexion of the right hip joint of the user in FIG. 21A decreases.

DETAILED DESCRIPTION

Figure 1:
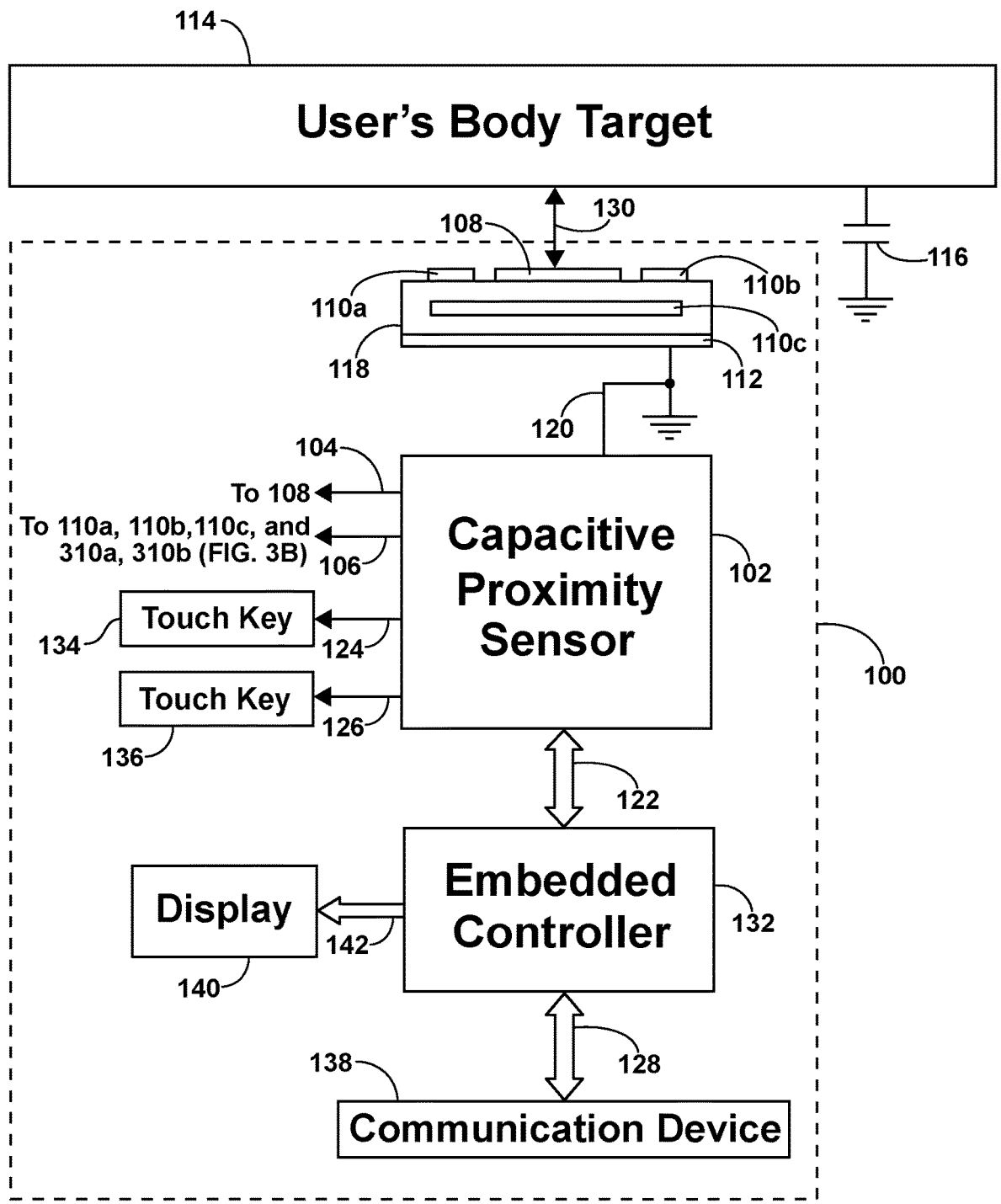
FIG. 1 is a block diagram showing schematically a wearable joint-action sensor incorporating a capacitive proximity sensor in accordance with the embodiments of the invention.

A proximity sensor is used in each of the embodiments of the wearable joint-action sensor for detecting actions of a joint, such as flexion and extension, by detecting the amount of separation between the proximity sensor and a target near the joint. We have found that using a proximity sensor to detect actions of a joint for monitoring physical activity of a user has a number of advantages:

(a) A single proximity sensor in the wearable joint-action sensor can detect actions of a joint directly without the need for obtaining data from multiple sensors located on the two body segments linked by a joint. As discussed in the first and eighth embodiments below, the wearable joint-action sensor worn on the right waist of a user can detect actions of the right hip joint, such as flexion, extension, abduction, and adduction, so that physical activities, such as walking, running, dancing, standing, and sitting, can be detected without requiring attaching a second sensor to the right thigh, as suggested by the prior arts.

(b) A proximity sensor in the wearable joint-action sensor can detect actions of a joint accurately without suffering from being significantly influenced by vibration of a user's body as an accelerometer-based physical-activity monitor would be, because an accelerometer-based physical-activity monitor detects movements of a single body segment (which moves during vibration) while the proximity sensor in the wearable joint-action sensor detects relative movements of two body segments (which tend to move together during vibration) linked by a joint.

(c) The wearable joint-action sensor based on proximity sensing is easy to wear, compact, efficient, and low cost, so it is practical for widespread use for physical-activity monitoring or for controlling a computing device, such as an electronic game console, electronic piano (or any electronic music instrument), smartwatch, fitness wristband, smartphone, or computer.

(d) The wearable joint-action sensor based on proximity sensing is very reliable and durable because it does not suffer from wear and tear of mechanical parts after repeated use.

Proximity sensors are well known in the art of sensing, and they have a high reliability and long functional life because there is no moving mechanical part. Common proximity sensors include capacitive proximity sensors, active infrared proximity sensors (which use both infrared-light sources and detectors), passive infrared proximity sensors (which use only infrared-light detectors), inductive proximity sensors, magnetic proximity sensors, ultrasonic proximity sensors, single-chip radars (which are widely used in automobiles for safety and convenience), visible- or infrared-light imaging sensors or auto-focus rangefinders (with or without a light source), and time-of-flight proximity sensors (which are advanced active infrared proximity sensors) that measure the time that light (typically infrared light) takes to travel to the target and reflect back to the sensor.

Many different types of proximity sensors can be used in the embodiments of the wearable joint-action sensor. An active infrared proximity sensor (including time-of-flight proximity sensors), ultrasonic proximity sensor, or single-chip radar requires emitting a beam of waves to its target for detecting the amount of separation between the sensor and the target, so it consumes additional power for producing the beam of waves. Without emitting a beam of waves, an inductive proximity sensor or a magnetic proximity sensor detects the amount of separation between the proximity sensor and a metal target, but it would be inconvenient for the user to wear the metal target on a body segment. Visible- or infrared-light imaging sensors or autofocus rangefinders can be used as proximity sensors, but they require adequate illumination of their targets. Without adequate illumination, infrared-light imaging sensors or autofocus rangefinders, or passive infrared proximity sensors (often referred to as pyroelectric sensors), can perform proximity sensing based on the infrared radiation of a warm target, such as a body segment of a human being or an animal if the body segment is not covered with thick clothing.

A capacitive proximity sensor is simple, low-cost, and does not require emitting a beam of waves or using a metal target. We presently contemplate using a capacitive proximity sensor in the wearable joint-action sensor, although any other type of proximity sensor, such as an active infrared proximity sensor, can replace the capacitive proximity sensor in the embodiments of the wearable joint-action sensor. Using a capacitive proximity sensor for the embodiments should not be construed as limiting the scope of the embodiments, but merely as providing illustrations of some of the presently preferred embodiments. For example, the capacitive proximity sensor in the embodiments of the wearable joint-action sensor can be replaced with an active or passive infrared proximity sensor, visible- or infrared-light imaging sensor or rangefinder (with or without a light source), ultrasonic proximity sensor, single-chip radar, or any other type of proximity sensor, without departing from the spirit and the scope of the embodiments.

Many techniques have been developed for measuring capacitance. A simple technique is to charge an unknown capacitor with a constant current source to produce a voltage change across the unknown capacitor, so that the value of capacitance of the unknown capacitor is simply equal to the charge (i.e. the constant current multiplied by the charging time) divided by the voltage change. A capacitive proximity sensor can measure an increase in capacitance when a target moves closer to the sensing plate of the capacitive proximity sensor, and vice versa, so the capacitance measured with the sensing plate of the capacitive proximity sensor can be used for representing the separation between the capacitive proximity sensor and the target, if the target remains the same.

In general, there are two types of capacitive proximity sensing systems: mutual-capacitive proximity sensing and self-capacitive proximity sensing. In a mutual-capacitive proximity sensing system, a sensing target (such as a finger) alters the mutual capacitive coupling between two sensing pads (i.e. two electrodes) on a sensing plate. The capacitive change is sensed by a capacitance sensor for detecting the separation between the sensing pads (i.e. the sensing plate, because the thickness of a sensing pad is usually negligible) and the target. In a self-capacitive proximity sensing system, a target (such as a finger) capacitance to ground increases the parasitic capacitance of a sensing pad (on a sensing plate) to ground. This is sensed by a capacitance sensor for detecting the separation between the sensing pad (i.e. the sensing plate) and the target. Either mutual-capacitive proximity sensing or self-capacitive proximity sensing can be used for the wearable joint-action sensor, although we presently contemplate using self-capacitive proximity sensing because of the availability of low-cost self-capacitive proximity sensors.

Capacitive proximity sensors have been used in mobile phones for detecting close proximity of a user's cheek as the user holds the phone next to the ear during a call, so that the touchscreen of the phone can be disabled to prevent accidental touchscreen taps. An advanced capacitive proximity sensor available from Semtech Corporation of California (Product Number: SX9300) can be used in a mobile phone for accurately discriminating between an inanimate object and human body proximity, so that the mobile phone can reduce its radio-frequency emission power in the presence of a human body to control the radio-frequency power absorbed by the human body to be within a safe level. The advanced capacitive proximity sensor consists of two capacitive proximity sensors and two sensing pads (one sensing pad for each capacitive proximity sensor) of equal surface areas, with one sensing pad (the inner sensing pad) completely surrounded by the other sensing pad (the outer sensing pad). By using this approach for capacitive proximity sensing, the advanced capacitive proximity sensor is able to discriminate between proximity generated by a low-permittivity object (such as a table) and a high-permittivity object (such as a human body).

A capacitive proximity sensor adjusted to a very short range can be used as a touch key, such as a key on the key pad of a mobile phone. For the embodiments of the wearable joint-action sensor, touch sensing can also be used, because it is a form of proximity sensing. Any proximity sensor, such as a capacitive proximity sensor, active infrared proximity sensor (including time-of-flight proximity sensors), passive infrared proximity sensor, inductive proximity sensor, magnetic proximity sensor, ultrasonic proximity sensor, single-chip radar, and visible- or infrared-light imaging sensor or auto-focus rangefinder (with or without a light source) can also be used for touch sensing to detect joint actions in the embodiments of the wearable joint-action sensor.

For the embodiments of the wearable joint-action sensor, we contemplate using an 8-channel capacitive touch sensor with proximity detection and signal guard that is available from Microchip Technology Inc. of Arizona (Product Number: CAP1298), although a capacitive proximity sensor manufactured by another company, such as Semtech Corporation of California (Product Number: SX9300, as discussed above), can also be used. Alternatively, an active infrared proximity sensor, such as an infrared proximity sensor available from Maxim Integrated Products Inc. of California (Product Number: MAX44000) operating with one or more external infrared light-emitting diodes (LEDs, the active light sources of the active infrared proximity sensor), or any other type of proximity sensor, can be used for the embodiments of the wearable joint-action sensor. We presently contemplate using one or more channels of the capacitive proximity sensor for self-capacitive proximity sensing, and the remaining channels for capacitive touch sensing of conventional touch keys, so that a user can interact with the wearable joint-action sensor by using the tip of a finger to touch the touch keys.

FIG. 1

Wearable Joint-Action Sensor

FIG. 1 shows a block diagram of a wearable joint-action sensor 100 incorporating a capacitive proximity sensor 102, which has multiple capacitive proximity-sensing channels. FIG. 1 also shows a side view of a sensing pad 108 (with optional signal guards 310a and 310b shown in FIG. 3B removed to expose sensing pad 108) on a sensing plate 118 of wearable joint-action sensor 100, as well as a user's body target 114, which is one or both (i.e. the region comprising both of the two body segments) of the two body segments linked by a joint, of which actions are sensed by wearable joint-action sensor 100. User's body target 114 serves as the target for capacitive proximity sensor 102 (i.e. for sensing pad 108 on sensing plate 118 of capacitive proximity sensor 102). A body segment, such as the torso (including the abdomen, waist, chest, shoulder, etc. of the torso), a section of the spinal-column, the head, the neck, an upper arm, a forearm (including the wrist region, etc. of the forearm), a hand (including the wrist region, back, palm, fingers, etc. of the hand), a finger segment, an upper leg (including the thigh, buttock, etc. of the upper leg), a lower leg (including the ankle region, etc. of the lower leg), a foot, or a toe segment, is one of the constituent parts into which the body of a human or an animal is divided or marked off by natural boundaries for the discussion of the embodiments.

Sensing pad 108 on sensing plate 118 is connected to a channel 104 of capacitive proximity sensor 102 for capacitive proximity sensing, so that the amount of a separation 130 between sensing pad 108 on sensing plate 118 and user's body target 114 can be detected for detecting actions of the joint (the joint is not shown in FIG. 1), such as flexion and extension. To simplify discussion in this description, the separation between sensing plate 118 and user's body target 114 is also separation 130, because the thickness of sensing pad 108 is usually negligible. Furthermore, separation 130 is also used as the separation between capacitive proximity sensor 102 and user's body target 114, because capacitive proximity sensor 102 uses sensing pad 108 on sensing plate 118 for detecting separation 130.

In the embodiments of wearable joint-action sensor 100 for sensing joint actions, wearable joint-action sensor 100 is strategically worn on a first body segment of a joint, which links the first body segment to a second body segment. User's body target 114 is one of the two body segments linked by the joint or both body segments in a region near the joint (i.e. a region comprising both body segments). Sensing pad 108 on sensing plate 118 is in an appropriate proximity of user's body target 114 for joint-action detection by detecting separation 130 with capacitance, which represents separation 130, obtained from capacitive proximity sensor 102. When the surface of user's body target 114 is not parallel to the surface of sensing pad 108 on sensing plate 118, the amount of separation 130 is represented by an average capacitance sensed by sensing pad 108. Furthermore, when user's body target 114 for detecting actions of a joint is a combination of the first body segment and the second body segment near the joint (i.e. user's body target 114 is a region comprising both the first body segment and the second body segment near the joint), the amount of separation 130 is also represented by an average capacitance detected by using sensing pad 108 on sensing plate 118, where the body segment that is larger and closer in front of sensing pad 108 contributes more to the average capacitance of the two body segments in the region near the joint.

Any additional clothing material (not shown in FIG. 1) that covers user's body target 114 or any additional protective material (not shown in FIG. 1) that covers sensing pad 108 can change the capacitance between user's body target 114 and sensing pad 108, even though separation 130 is unchanged. When the air gap between the surfaces of the covering materials of user's body target 114 and sensing pad 108 is large, the capacitance between user's body target 114 and sensing pad 108 largely results from the air gap. In this case, the capacitance resulting from the air gap is connected in series with the capacitances resulting from the covering materials (the covering materials are usually relatively thin), which are usually much larger than the capacitances resulting from the air gap, so that the capacitance resulting from the air gap dominates the total capacitance of the series combination of capacitances.

When the air gap between the surfaces of the covering materials approaches the total thickness of the covering materials, the capacitances resulting from the covering materials, which remain constant as the capacitance resulting from the air gap changes, contribute significantly to the capacitance between user's body target 114 and sensing pad 108. In this case, the capacitance between user's body target 114 and sensing pad 108 approaches the constant series combination of the capacitances of the covering materials as the air gap decreases. This constant series combination of capacitances is in series with a capacitance 116 (a relatively constant capacitance after the user wears wearable joint-action sensor 100 on the body) of user's body target 114 to ground, and if possible, the total series capacitance can be determined by having the user perform a joint action that closes the air gap and then obtaining the corresponding capacitance data from capacitive proximity sensor 102. To compute the capacitance resulting from the air gap, this capacitance data can be stored and used along with the capacitance data obtained from capacitive proximity sensor 102 when the air gap is not closed, because the capacitance data obtained when the air gap is not closed is a serial combination of the stored capacitance data (obtained when the air gap is closed) and the capacitance resulting from the air gap.

The capacitance obtained from capacitive proximity sensor 102 is typically a binary number (such as the count of a binary counter) that is proportional to the standard measurement of capacitance in Farads. Converting the capacitance obtained from capacitive proximity sensor 102 to the capacitance measurement in Farads is usually unnecessary. Using the capacitance obtained from capacitive proximity sensor 102, the computed separation of the air gap (i.e. the size of the air gap), which is obtained from the computed capacitance resulting from the air gap, can also be a binary number that is related to the separation in a standard measurement unit (such as in millimeter). Separation 130 (i.e. the capacitance that represents separation 130, as discussed below) is equal to the separation of the air gap plus the total thickness of the covering materials (not shown in FIG. 1), which can either be determined though the method described above (for the protective material on sensing pad 108) or is relatively thin and therefore negligible (for the clothing on user's body target 114). After the user wears wearable joint-action sensor 100 on the body, capacitance 116 of user's body target 114 to ground is relative constant, so the capacitance obtained from capacitive proximity sensor 102 can be directly used for representing separation 130, without computing the separation of the air gap, because the capacitance increases as separation 130 decreases, and vice versa, and each value of the capacitance corresponds to a specific value of separation 130 in this case.

Optional signal guards 110a, 110b, 110c, 310a, and 310b (in FIGS. 1 and 3B) around sensing pad 108 are driven by a signal-guard output 106 of capacitive proximity sensor 102 with low output impedance to match the voltage of sensing pad 108, so that there is almost no electrical field between sensing pad 108 and signal guards 110a, 110b, 110c, 310a, and 310b. By having signal guards 110a, 110b, 110c, 310a, and 310b around sensing pad 108, the base capacitance of sensing pad 108 is almost zero, so the capacitance detected by using sensing pad 108 of capacitive proximity sensor 102 is largely affected by capacitance 116 of user's body target 114 to ground and separation 130 between sensing pad 108 and user's body target 114. When wearable joint-action sensor 100 is worn on the user's body (this part of the user's body is not shown in FIG. 1) with sensing pad 108 detecting separation 130 between sensing pad 108 on sensing plate 118 and user's body target 114, the capacitance detected by using sensing pad 108 on sensing plate 118 increases as separation 130 decreases, and vice versa.

A ground plane 112 on the back of sensing plate 118 shields sensing pad 108 and signal guards 110a, 110b, 110c, 310a, and 310b from unwanted electric fields in the environment around sensing plate 118. Ground plane 112, sensing pad 108, and signal guards 110a, 110b, 110c, 310a, and 310b are made of any electrically conductive material, such as the copper layers of a multi-layer printed circuit board, and signal guards 110a, 310b, 110b and 310a join together to become the four sides of a single electrically conductive trace around sensing pad 108, as illustrated in FIG. 3B. If optional signal guards 110a, 110b, 110c, 310a, and 310b are not used, the base capacitance of sensing pad 108 is mostly the capacitance between sensing pad 108 and ground plane 112. When necessary, this base capacitance can be reduced to improve sensitivity of capacitive proximity sensor 102 to separation 130 by increasing the separation between sensing pad 108 and ground plane 112, or by cross-hatching ground plane 112.

The circuit ground 120 of capacitive proximity sensor 102 is connected to ground plane 112, so that capacitive proximity sensor 102 senses capacitances of channel 104, channel 124, and channel 126 to ground plane 112. Capacitive proximity sensing of channel 124 and channel 126 is adjusted to a very short range for sensing optional touch keys 134 and 136, respectively, which is used for user interface. Although three capacitive proximity sensing channels 104, 124, and 126 of capacitive proximity sensor 102 are illustrated in FIG. 1, more or fewer capacitive proximity sensing channels can be employed as needed for an embodiment. Similarly, although one signal-guard output 106 is shown in FIG. 1, capacitive proximity sensor 102 can have more signal-guard outputs or no signal-guard output at all.

Capacitive proximity sensor 102 uses a bus 122, such as an inter-integrated circuit bus or a serial peripheral interface bus, to communicate with an embedded controller 132, which usually comprises a microprocessor with memory for data storage. The capacitance sensed by using sensing pad 108 on sensing plate 118, as well as the capacitive touch statuses of touch keys 134 and 136, are sent to embedded controller 132 through bus 122. On the other hand, embedded controller 132 uses bus 122 to configure capacitive proximity sensor 102 for appropriate proximity and touch-key sensing. Embedded controller 132 uses an output bus 142 to drive an optional display 140, such as an LCD module, for user interface. Embedded controller 132 also uses a bus 128, such as an inter-integrated circuit bus or a serial peripheral interface bus, to communicate with an optional communication device 138. Communication device 138, such as a USB (Universal Serial Bus), Bluetooth®, Wi-Fi®, or NFC (near-field communication) device, or any radio-frequency, optical, acoustic, or wired communication device, provides wired or wireless communication for embedded controller 132 to communicate with a computing device (not shown in FIG. 1), such as a smartwatch, fitness wristband, smartphone, or computer. Embedded controller 132 can use the display of the computing device for displaying any data or result, so that display 140 is not needed. Communication device 138 can also connect wearable joint-action sensor 100 to the internet to make wearable joint-action sensor 100 a part of the Internet of Things (IoT).

Embedded controller 132 processes capacitance data obtained from capacitive proximity sensor 102, which represents data of separation 130, to determine joint actions, such as flexion and extension, and the result can be shown on display 140, or the display of a computing device by using communication device 138. Alternatively, by using communication device 138, the capacitance data obtained from capacitive proximity sensor 102 can be downloaded to a computing device (not shown in FIG. 1) or to any device that is connected to the internet (such as the cloud or a smartphone) for data processing and display, so that embedded controller 132 and display 140 are not needed in wearable joint-action sensor 100. Similarly, the computing device or any device that is connected to the internet can send configuration data and instructions to capacitive proximity sensor 102 directly to control its operation, so that touch keys 134 and 136 are not needed.

Joint-Action Detection Operation

FIG. 2

Figure 2:
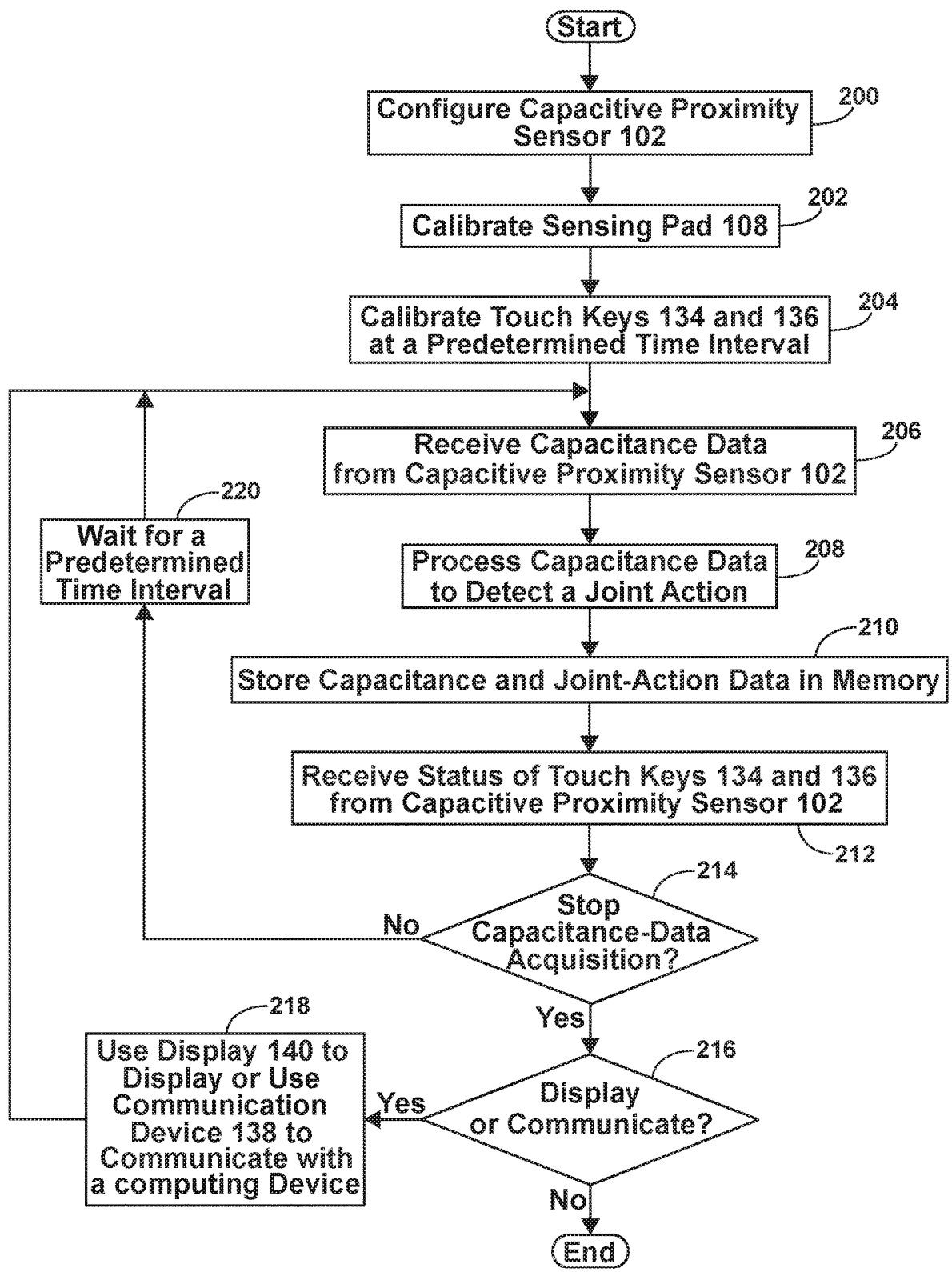
FIG. 2 is a flow diagram illustrating the operation of the wearable joint-action sensor in FIG. 1 in accordance with the embodiments of the invention.

FIG. 2 is a flow diagram illustrating the joint-action detection operation of wearable joint-action sensor 100 in FIG. 1. In FIG. 2, after wearable joint-action sensor 100 has been turned on, embedded controller 132 sends configuration data, such as gain and sensitivity, through bus 122 to set up capacitive proximity sensor 102 at step 200, for proximity sensing using sensing pad 108 and for touch sensing using conventional touch keys 134 and 136.

At step 202, embedded controller 132 uses bus 122 to initiate capacitive proximity sensor 102 to calibrate sensing pad 108 for determining the base capacitance of sensing pad 108 when user's body target 114 is furthest away from sensing pad 108, and if possible, for determining the total capacitance resulting from the covering materials in series with capacitance 116 when the air gap between the covering materials is closed. The calibration process can be performed by instructing the user to perform a predetermined joint action (such as a full flexion or extension of a joint), or during the manufacturing process or the operation of wearable joint-action sensor 100 (such as during the operation of the first embodiment, as discussed below), so that the user does not need to perform the calibration process at step 202. Capacitive proximity sensor 102 uses the base capacitance of sensing pad 108 as the reference to obtain capacitance data when user's body target 114, with its capacitance 116 to ground, approaches sensing pad 108 on sensing plate 118 with separation 130.

At step 204, embedded controller 132 uses bus 122 to initiate capacitive proximity sensor 102 to calibrate touch keys 134 and 136 at a predetermined time interval, which may be set up at step 200. For touch keys 134 and 136, the calibration process is performed periodically at the predetermined time interval for determining the base capacitances of touch keys 134 and 136, so that a touch is detected when the capacitance of touch key 134 or 136 exceeds a threshold capacitance (which may also be set up at step 200) above the base capacitance of touch key 134 or 136. After a user wears wearable joint-action sensor 100 and moves around, the periodic calibration reduces the environment's influence on changes in capacitances during the touch-detection process for touch keys 134 and 136. On the other hand, a user is required to perform a predetermined joint action, such as a full flexion or extension of a joint, for calibrating sensing pad 108 on sensing plate 118, and the calibration process is performed much less frequently (or not at all) after the user wears joint-action sensor 100, because the capacitance sensed by using sensing pad 108 is mostly a series combination of the capacitance resulting from separation 130 (between sensing pad 108 on sensing plate 118 and user's body target 114) and capacitance 116 of user's body target to ground, which is a relatively constant capacitance after the user wears wearable joint-action sensor 100 on the body.

By using bus 122 at step 206, embedded controller 132 receives capacitance data that represents data of separation 130 between sensing pad 108 on sensing plate 118 and user's body target 114 from capacitive proximity sensor 102. At step 208, a software or hardware joint-action detector in embedded controller 132 uses the capacitance data and the rate of change of the data (if necessary) to detect a joint action, such as flexion or extension, of the joint sensed by wearable joint-action sensor 100. The joint-action data obtained from step 208, as well as the raw capacitance data obtained from step 206, are stored in the memory of embedded controller 132 at step 210. By using bus 122 at step 212, embedded controller 132 receives the touch statuses of touch keys 134 and 136 from capacitive proximity sensor 102 to find out at steps 214 and 216 if the user wants to control the operation of embedded controller 132, such as to stop capacitance-data acquisition for joint-action detection, to display data, or to communicate with a computing device, such as a smartwatch, fitness wristband, smartphone, or computer. Under computer program control, embedded controller 132 can also stop capacitance-data acquisition for joint-action detection, display data, or communicate with a computing device, without requiring the user to use touch key 134 or 136.

If capacitance-data acquisition is not stopped at step 214 under computer program control, embedded controller 132 waits for a predetermined time interval at step 220 before it returns to step 206 to receive more capacitance data from capacitive proximity sensor 102. On the other hand, if capacitance-data acquisition is stopped at step 214 under computer program control (such as when a predetermined joint action or a specific pattern of the touch statuses of touch keys 134 and 136 has been detected), embedded controller 132 can end all the processes shown in FIG. 2 at step 216. It can also go to step 218 to display any data stored in the memory of embedded controller 132 by using display 140 or communicate with a computing device by using communication device 138. If embedded controller 132 does not end all the processes shown in FIG. 2 at step 216, embedded controller 132 returns to step 206 to receive more capacitance data from capacitive proximity sensor 102 after displaying data or communicating with a computing device at step 218.

Although a user of wearable joint-action sensor 100 is typically a human being, a user can be a four-limbed animal, such as a monkey, dog, cat, goose, or elephant, for which joint actions are being detected by wearing wearable joint-action sensor 100 using similar proximity sensing techniques as disclosed in the embodiments. Furthermore, the following description of the embodiments is not intended to limit the invention to these embodiments, but rather to enable any person skilled in the art to make and use the invention.

Figure 3A:
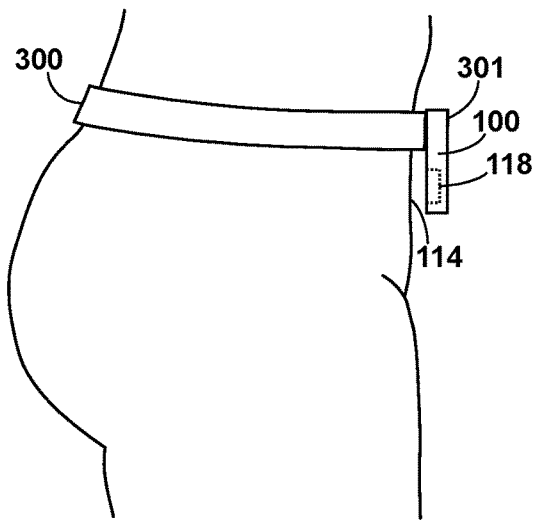
FIG. 3A is a graphical illustration of a possible location of the wearable joint-action sensor for detecting actions of the right hip joint of a user in accordance with the first embodiment.
Figure 3B:
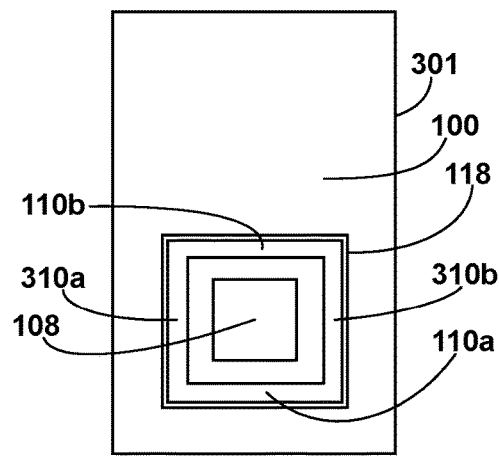
FIG. 3B is a front view (the surface that faces the right abdomen of the user) of the wearable joint-action sensor in FIG. 3A.

FIGS. 3A and 3B

First Embodiment

A first embodiment of the wearable joint-action sensor is illustrated in FIGS. 3A and 3B. FIG. 3A is a side view of wearable joint-action sensor 100 inside a housing 301 worn on the right waist of the torso (the torso is the first body segment in this embodiment) of a user (a human being in this embodiment) with a waist belt 300 for detecting joint actions, such as flexion and extension, of the right hip joint of the user. Wearable joint-action sensor 100 inside housing 301 incorporates sensing plate 118 (details in FIGS. 1 and 3B), which is illustrated by a dotted outline. The right hip joint links the right abdomen of the torso to the right thigh of the right upper leg (the right upper leg is the second body segment in this embodiment), and sensing pad 108 on sensing plate 118 of wearable joint-action sensor 100 is in the proximity of the first body segment (the right abdomen of the torso above the right thigh) for detecting separation 130 (in FIG. 1) between capacitive proximity sensor 102 (i.e. sensing plate 118 of capacitive proximity sensor 102) and the first body segment, which serves as user's body target 114 for sensing plate 118.

FIG. 3B is a front view (the surface that faces the right abdomen of the user) of wearable joint-action sensor 100 inside housing 301 in FIG. 3A. Sensing pad 108 is at the center of sensing plate 118, with optional signal guards 110a, 110b, 310a, and 310b around sensing pad 108. Signal guards 110a, 310b, 110b and 310a join together to become the four sides of a single electrically conductive trace around sensing pad 108. Optional signal guard 110c (in FIG. 1) is underneath sensing pad 108, as well as underneath signal guards 110a, 110b, 310a, and 310b, so it is not shown in FIG. 3B. In FIG. 3B, although sensing pad 108 on sensing plate 118 shown in the front view of housing 301 is exposed with no covering material, sensing pad 108 on sensing plate 118 can be covered with a protective material or be placed inside housing 301 without being exposed. Furthermore, sensing pad 108 and sensing plate 118 can be of any shape, although they are shown to be rectangular in FIG. 3B.

Wearable joint-action sensor 100 inside housing 301 can be attached to waist belt 300 by using a mounting clip, which is commonly used for wearing a mobile phone or pager on the waist of a user. Wearable joint-action sensor 100 inside housing 301 can be attached to waist belt 300 by any other mechanism, such as by sewing, or by using any type of magnetic, adhesive, or adhering device. Wearable joint-action sensor 100 inside housing 301 can also be attached directly, such as by adhesive or adhesive tape, to the right waist of a user without using waist belt 300, or be clipped to a pants pocket that is close to the right waist. Furthermore, wearable joint-action sensor 100 can be incorporated inside the housing of a smartphone that is worn on the right waist of a user, so that housing 301 is not needed. As illustrated in FIG. 3A, there is an appropriate separation between sensing plate 118 and user's body target 114 when the user is standing. We presently contemplate using a square copper pad (approximately 2.5 cm×2.5 cm) on a printed circuit board as sensing pad 108 (in FIGS. 1 and 3B) with ground plane 112 but without any signal guard on sensing plate 118. In this case, separation 130 between sensing pad 108 on sensing plate 118 and user's body target 114 (i.e. between sensing plate 118 and user's body target 114, because the thickness of sensing pad 108 is negligible) is less than 1.5 cm, although sensing pad 108 of any other size or shape, with or without signal guard or ground plane, and a different amount of separation 130 between sensing pad 108 on sensing plate 118 and user's body target 114 can also be used. User's body target 114 at the right abdomen of the torso is usually covered with clothing, but we have found that sensing plate 118 can still be used for sensing the amount of separation 130 and the rate of change between sensing plate 118 and user's body target 114, because typical clothing materials do not alter the electric field between sensing pad 108 on sensing plate 118 and user's body target 114 severely.

Although only one sensing plate 118 is illustrated in FIGS. 3A and 3B, multiple smaller sensing plates, which can be arranged in a one- or two-dimensional array, or in any spatial pattern, can be incorporated in wearable joint-action sensor 100 to obtain more separation data for the right abdomen of the torso as a user flexes or extends the right hip joint. Wearable joint-action sensor 100 with multiple sensing plates can be used for detecting distortion of the right abdomen of the torso of a user when the user abducts or adducts the right hip joint, or when the user performs a combination of actions (for example, flexion combined with abduction) of the right hip joint, such as when the user is dancing. Wearable joint-action sensor 100 with multiple sensing plates can also facilitate obtaining appropriate separation data for the right abdomen of the torso even when a user does not wear wearable joint-action sensor 100 exactly as directed, because in this case some of the sensing plates could still be located at an appropriate proximity of the right abdomen of the torso for detecting actions of the right hip joint of the user.

Joint-Action Detection Operation

Figure 4A:
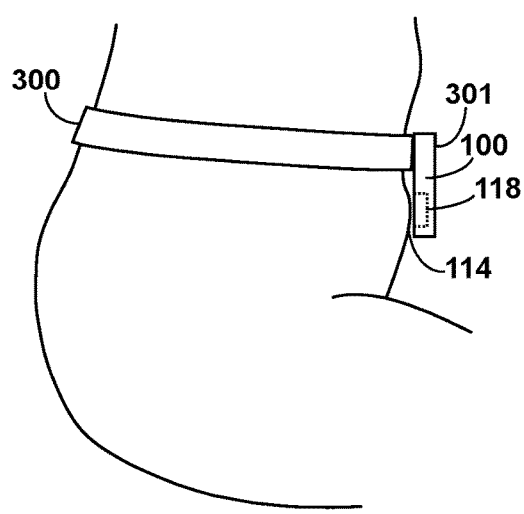
FIG. 4A is a graphical illustration of a decrease in the amount of separation between the capacitive proximity sensor (i.e. the sensing plate of the capacitive proximity sensor) and the right abdomen above the right thigh as the right hip joint of the user in FIG. 3A is flexed.
Figure 4B:
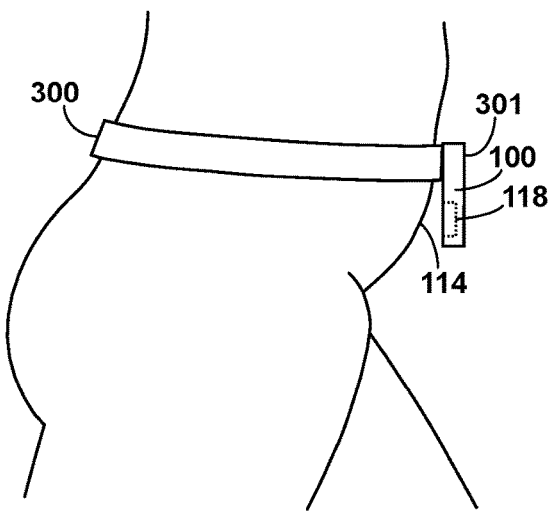
FIG. 4B is a graphical illustration of an increase in the amount of separation between the capacitive proximity sensor and the right abdomen above the right thigh as the right hip joint of the user in FIG. 3A is extended.

FIGS. 4A and 4B

FIG. 4A illustrates a decrease in the amount of separation 130 (in FIG. 1) between sensing plate 118 of capacitive proximity sensor 102 (in FIG. 1) and user's body target 114 (i.e. between capacitive proximity sensor 102 and user's body target 114) as the right abdomen of the torso bulges out when a user flexes the right hip joint. The bulging out of the right abdomen of the torso is initiated by contractions of the right psoas major and iliacus muscles, which flex the right hip joint and cause bulging out of the soft tissues of the right abdomen of the torso. The decrease in the amount of separation 130 results in an increase in capacitance of sensing pad 108 (in FIG. 1) on sensing plate 118 to ground, which is detected by capacitive proximity sensor 102. In FIG. 4A, although there is still a small amount of separation 130 between sensing plate 118 and user's body target 114 when the right hip joint of the user is flexed, sensing plate 118 can touch (or almost touch) user's body target 114 for detecting flexion of the right hip joint, such as when the user is sitting.

On the other hand, FIG. 4B illustrates an increase in the amount of separation 130 between sensing plate 118 and user's body target 114 as the right abdomen of the torso stretches out when the user extends the right hip joint. The stretching out of the right abdomen of the torso is caused by relaxation of the right psoas major and iliacus muscles and by pulling of the soft tissue of the right abdomen of the torso when the right hip joint extends. The increase in the amount of separation 130 results in a decrease in capacitance of sensing pad 108 on sensing plate 118 to ground, which is detected by capacitive proximity sensor 102.

When a user walks or runs, the right hip joint flexes as the user takes a step forward with the right leg, and the right hip joint extends as the user takes a step forward with the left leg (in FIG. 4B). Wearable joint-action sensor 100 inside housing 301 in the first embodiment can be used as a physical-activity monitor by using sensing pad 108 on sensing plate 118 to sense the periodic variation of the capacitance to ground, which represents the periodic variation of separation 130, and measuring the rate of change of the capacitance to ground when the user walks or runs. The number of steps that the user takes can be detected by analyzing the waveform of the capacitance to ground with various techniques, such as by detecting the total number of peaks and valleys of the waveform, which corresponds to the total number of maximum flexions and maximum extensions of the right hip joint, respectively. Alternatively, multiplying the number of significant flexions of the right hip joint by a factor of two can produce the number of steps that the user takes, where significant flexion is any degree of flexion that is larger than the minimum degree of flexion of the right hip joint required for the user to take an ambulating step forward with the right leg. A significant flexion can be detected from the waveform of the capacitance to ground by using a capacitance threshold (i.e. a threshold for the degree of flexion), which can be determined based on the amplitude of the waveform, such as using a threshold at a predetermined percentage of the amplitude of the waveform above or below the midline of the waveform, depending on the specific design of wearable joint-action sensor 100. Unlike a pedometer that uses an accelerometer to detect steps, wearable joint-action sensor 100 does not mistakenly count steps when a user's body vibrates on a traveling vehicle, because the right hip joint does not flex and extend alternately in this case.

One advantage of using wearable joint-action sensor 100 as a physical-activity monitor is that it can detect whether a user is sitting or standing when the user is not walking or running. As illustrated in the block diagram (in FIG. 17) for the seventh embodiment, wearable joint-action sensor 100 in the first embodiment can also be used as a sitting detector for reminding a user (such as by vibration, sound, voice, light, or a message on display 140 or on the display of a computing device) that the user has been sitting for too long. The timer for reminding the user can be implemented by a hardware or software timer in embedded controller 132 or in reminder 1700 (in FIG. 17). Furthermore, reminder 1700 can be incorporated inside housing 301 of wearable joint-action sensor 100.

Wearable joint-action sensor 100 can detect sitting and standing accurately after capacitive proximity sensor 102 is calibrated for the degree of flexion of the right hip joint of a user. With less elaborate calibration, wearable joint-action sensor 100 can still detect sitting and standing quite accurately by using a timer to determine the duration of significant flexion or no significant flexion of a user's right hip joint, respectively. This is based on the fact that the right hip joint is in significant flexion for a long duration when the user is sitting, and the right hip joint is not in significant flexion for a long duration when the user is standing. When a user is doing squats for exercise instead of either sitting or standing, the right hip joint is alternating between significant flexion and no significant flexion, which can be detected by wearable joint-action sensor 100, so long as the duration of significant flexion or no significant flexion (or both) is longer than a predetermined duration for walking or running, indicating that the user is not walking or running.

The duration of significant flexion or no significant flexion, or the duration of any detected action of a joint, especially of a joint that is directly involved in ambulation, can be determined by a hardware or software timer implemented in embedded controller 132 (at least one hardware timer is usually incorporated in a microprocessor, and a software timer can be implemented by counting the number of times a computer program loop with a predetermined execution time has been executed). Sitting or standing (i.e. the user is not ambulating) can be detected by wearable joint-action sensor 100 when the duration of any detected action of a joint exceeds a predetermined duration. This can also distinguish between sitting and standing if the joint is a hip joint, as discussed above. If wearable joint-action sensor 100 is only used for detecting sitting, capacitive proximity sensor 102 can simply be a capacitive touch sensor, which is commonly incorporated in many microprocessors for sensing a capacitive touch key, and sensing pad 108 on sensing plate 118 of capacitive proximity sensor 102 can be designed to touch or be in close proximity to the right abdomen (likely though clothing) of a user when the user is sitting.

For example, instead of sensing actions of a hip joint for detecting sitting or standing, sitting or standing can be detected with less accuracy by using a hardware or software timer implemented in embedded controller 132 to determine the duration of the degree of flexion of a knee joint, which tends to be flexed significantly (i.e. the degree of flexion exceeds a predetermined threshold) when sitting, and not significantly flexed (i.e. the degree of flexion below the predetermined threshold) when standing. By using a similar detection principle, sitting or standing can be detected with even less accuracy by sensing actions of an elbow joint (instead of a hip or knee joint), which tends to be flexed (in FIG. 13) for a long duration when sitting, and extended (in FIG. 12) for a long duration when standing (detecting flexion and extension of the right elbow joint is discussed in the fifth embodiment). Furthermore, when a user is either sitting or standing instead of ambulating, the actions (also including the degree of the actions) of the user's joints, especially of the joints that are involved in ambulation directly, tend to decrease significantly. When the duration of a decrease in action of a joint (i.e. a decrease in the movement of a joint) determined by a timer exceeds a predetermined duration, sitting or standing (i.e. the user is not ambulating) is detected, although a decrease in action of most of the user's joints cannot be used for distinguishing between sitting and standing, except for some of the joints discussed above.

Wearable joint-action sensor 100 can use its communication device 138 and a signal link 1702 to communicate with reminder 1700 (in FIG. 17), which can be a voice recorder, vibrator, beeper, display, or simply a light-emitting diode (LED), for reminding a user that a predetermined action of the right hip joint, such as sitting or standing, is or has been detected. Reminder 1700 can also be far away from the user for reminding someone else, such as a caregiver of the user. Furthermore, wearable joint-action sensor 100 in the first embodiment can be used for detecting how much time a user spends in each of sitting, standing, and ambulating (i.e. either walking or running, with or without counting steps). The time distribution among these three types of physical activity that the user performs could be more relevant to the user for maintaining a good health than the number of steps counted with a prior-art pedometer.

Although FIGS. 4A and 4B illustrate that wearable joint-action sensor 100 is worn on the right waist of the torso of a user using waist belt 300 for detecting actions of the right hip joint, wearable joint-action sensor 100 can be worn on the left waist of the torso of a user with waist belt 300 for detecting actions of the left hip joint by using the same detection principle. Furthermore, wearable joint-action sensor 100 can be worn on the lower back of the torso above the buttock (i.e. the gluteal region of the upper leg) of the left or right upper leg using waist belt 300 to detect actions of the left or right hip joint, respectively, by using the same detection principle, because the buttock of the upper leg bulges out as the hip joint of the upper leg extends, and the buttock of the upper leg stretches out as the hip joint flexes. In this case, the change in separation 130 between sensing plate 118 and the top of the buttock of the upper leg, which serves as user's body target 114, is used for detecting actions of the hip joint. Wearable joint-action sensor 100 in the first embodiment can be used for detecting any type of physical activity that involves a hip joint, without the inconvenience of attaching a sensor to the thigh of the upper leg of a user, as necessary in the prior arts for sensing actions of a hip joint.

FIG. 5

Second Embodiment

Figure 5:
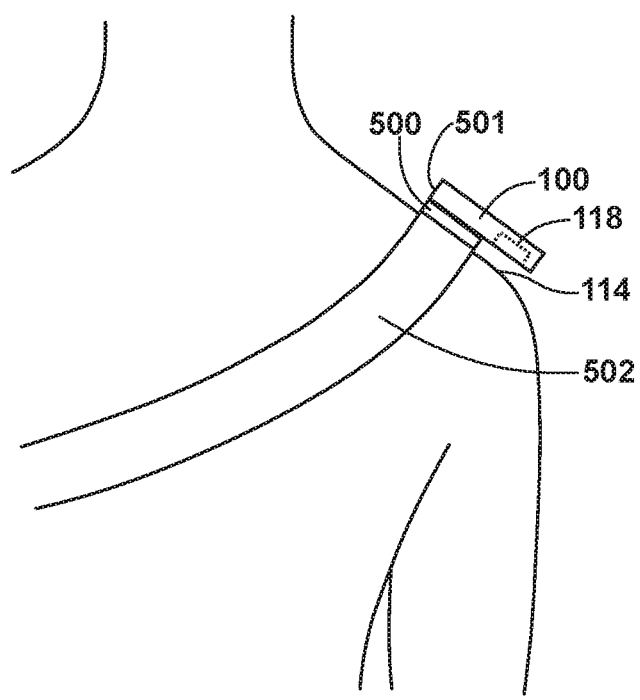
FIG. 5 is a graphical illustration of a possible location of the wearable joint-action sensor for detecting actions of the right shoulder joint of a user in accordance with the second embodiment.

A second embodiment of the wearable joint-action sensor is illustrated in FIG. 5. FIG. 5 is a side view of wearable joint-action sensor 100 inside a housing 501 worn on the right shoulder of the torso (the torso is the first body segment in this embodiment) of a user (a human being in this embodiment), on a shoulder pad 500 with a shoulder strap 502, for detecting actions, such as abduction and adduction, of the right shoulder joint of the user. Wearable joint-action sensor 100 inside housing 501 incorporates sensing plate 118, which is illustrated by a dotted outline. Sensing plate 118 of wearable joint-action sensor 100 is in the proximity of the user's right shoulder of the torso and the top of the right upper arm (the right upper arm is the second body segment in this embodiment), and both the right shoulder of the torso and the top of the right upper arm (i.e. the region comprising both the first and second body segments) serve as user's body target 114 for sensing plate 118. The right shoulder joint is adducted in FIG. 5, with soft tissues of the right shoulder and the top of the right upper arm stretched out.

Wearable joint-action sensor 100 inside housing 501 can be attached to shoulder pad 500 by using a mounting clip, or it can be attached to shoulder pad 500 by any other mechanism, such as by sewing, or by using any type of magnetic, adhesive, or adhering device. Furthermore, wearable joint-action sensor 100 can also be attached directly, such as by adhesive or adhesive tape, to the right shoulder of a user without using shoulder pad 500 and shoulder strap 502. As illustrated in FIG. 5, there is an appropriate separation between sensing plate 118 and user's body target 114 when the user's right shoulder joint is adducted.

Although only one sensing plate 118 is illustrated in FIG. 5, multiple sensing plates can be arranged around shoulder pad 500 to detect other actions of the right shoulder joint, such as flexion and extension. Wearable joint-action sensor 100 with multiple sensing plates can also facilitate obtaining appropriate separation data for the region comprising both the right shoulder and the top of the right upper arm even when a user does not wear wearable joint-action sensor 100 exactly as directed, because in this case some of the sensing plates could still be located at an appropriate proximity of the right shoulder and the top of the right upper arm for detecting actions of the right shoulder joint of the user.

Joint-Action Detection Operation

FIG. 6

Figure 6:
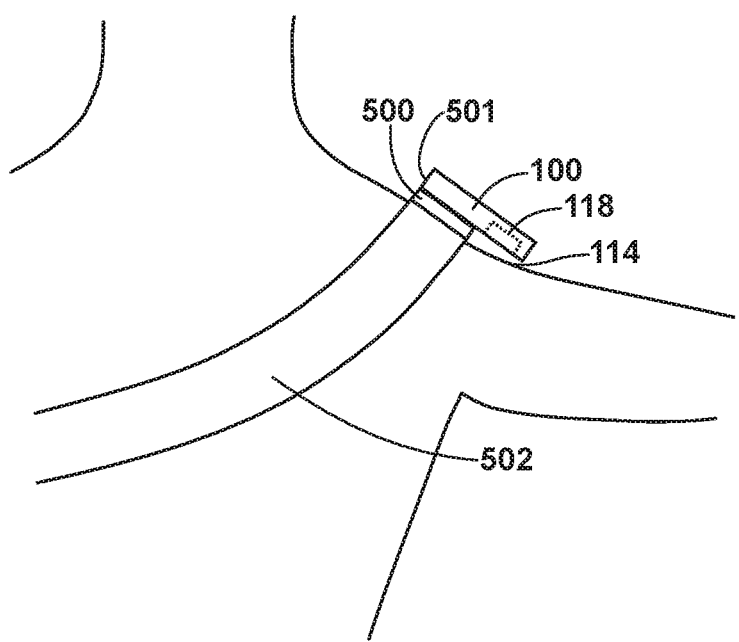
FIG. 6 is a graphical illustration of a decrease in the amount of separation between the capacitive proximity sensor and the region comprising both the right shoulder and the top of the right upper arm as the right shoulder joint of the user in FIG. 5 is abducted.

FIG. 6 illustrates a decrease in the amount of separation 130 (in FIG. 1) between sensing plate 118 of capacitive proximity sensor 102 (in FIG. 1) and user's body target 114 (i.e. between capacitive proximity sensor 102 and user's body target 114) as both the right shoulder of the torso and the top of the right upper arm become closer to sensing plate 118 when the user abducts the right shoulder joint, with soft tissues of the right shoulder and the top of the right upper arm bulging out. The decrease in the amount of separation 130 results in an increase in capacitance of sensing pad 108 (in FIG. 1) on sensing plate 118 to ground, which is detected by capacitive proximity sensor 102. In FIG. 6, although there is a small amount of separation 130 between sensing plate 118 and user's body target 114 when the right shoulder joint of the user is abducted, sensing plate 118 can touch (or almost touch) user's body target 114 for detecting abduction of the right shoulder joint.

When the user performs a physical activity that involves the right shoulder joint, such as swinging, lifting, or jumping rope, one or more sensing plates can be attached to shoulder pad 500 to detect the activity, so long as capacitive proximity sensor 102 of wearable joint-action sensor 100 can detect the amount of separation 130 and the rate of change between sensing plate 118 and user's body target 114 on the right shoulder and the top of the right upper arm (i.e. the region comprising both the right shoulder and the top of the right upper arm) as the right shoulder joint performs the action.

Although FIG. 6 illustrates that wearable joint-action sensor 100 inside housing 501 is worn on the right shoulder of the user with shoulder pad 500 and shoulder strap 502 for detecting actions of the right shoulder joint, wearable joint-action sensor 100 can be worn on the left shoulder of the user for detecting actions of the left shoulder joint by using the same detection principle.

FIG. 7

Third Embodiment

Figure 7:
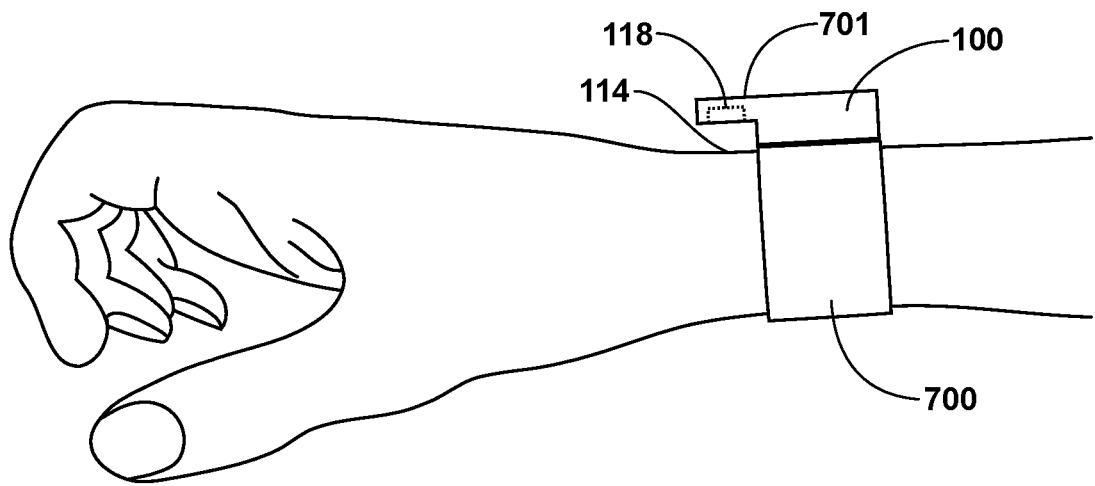
FIG. 7 is a graphical illustration of a possible location of the wearable joint-action sensor for detecting actions of the right wrist joint of a user in accordance with the third embodiment.

A third embodiment of the wearable joint-action sensor is illustrated in FIG. 7. FIG. 7 is a side view of wearable joint-action sensor 100 inside a housing 701 worn on the wrist region of the right forearm (the right forearm is the first body segment in this embodiment) of a user (a human being in this embodiment) with a wristband 700 for detecting joint actions, such as flexion and extension, of the right wrist joint of the user. Wearable joint-action sensor 100 inside housing 701 incorporates sensing plate 118, which is illustrated by a dotted outline. Sensing plate 118 of wearable joint-action sensor 100 is in the proximity of the wrist region of the right hand (the right hand is the second body segment in this embodiment) and the wrist region of the right forearm. The right wrist joint links the wrist region of the right forearm to the wrist region of the right hand, and both the wrist region of the right forearm and the wrist region of the right hand (i.e. the region comprising both the first and second body segments) serve as user's body target 114 for sensing plate 118.

Wearable joint-action sensor 100 inside housing 701 can be attached to wristband 700 by using any mechanism for attaching a wristwatch to a wristband, or by using any type of magnetic, adhesive, or adhering device. Wearable joint-action sensor 100 can also be attached directly, such as by adhesive or adhesive tape, to the wrist region of the right forearm of a user without using wristband 700. Furthermore, wearable joint-action sensor 100 can be incorporated inside the housing of a smartwatch, which is worn on the wrist region of the right forearm of a user, so that housing 701 is not needed. As illustrated in FIG. 7, there is an appropriate separation 130 (in FIG. 1) between sensing plate 118 and user's body target 114 when the right wrist joint is not flexed or extended.

Although only one sensing plate 118 is illustrated in FIG. 7, multiple sensing plates can be incorporated in wearable joint-action sensor 100 to obtain more separation data for the region comprising both the wrist region of the right hand and the wrist region of the right forearm as the user flexes or extends the right wrist joint. Wearable joint-action sensor 100 with multiple sensing plates can facilitate obtaining appropriate separation data for the region comprising both the wrist region of the right hand and the wrist region of the right forearm even when a user does not wear wearable joint-action sensor 100 exactly as directed, because in this case some of the sensing plates could still be located at an appropriate location in the proximity of the wrist region of the right hand and the wrist region of the right forearm for detecting actions of the right wrist joint of the user.

Joint-Action Detection Operation

Figure 8A:
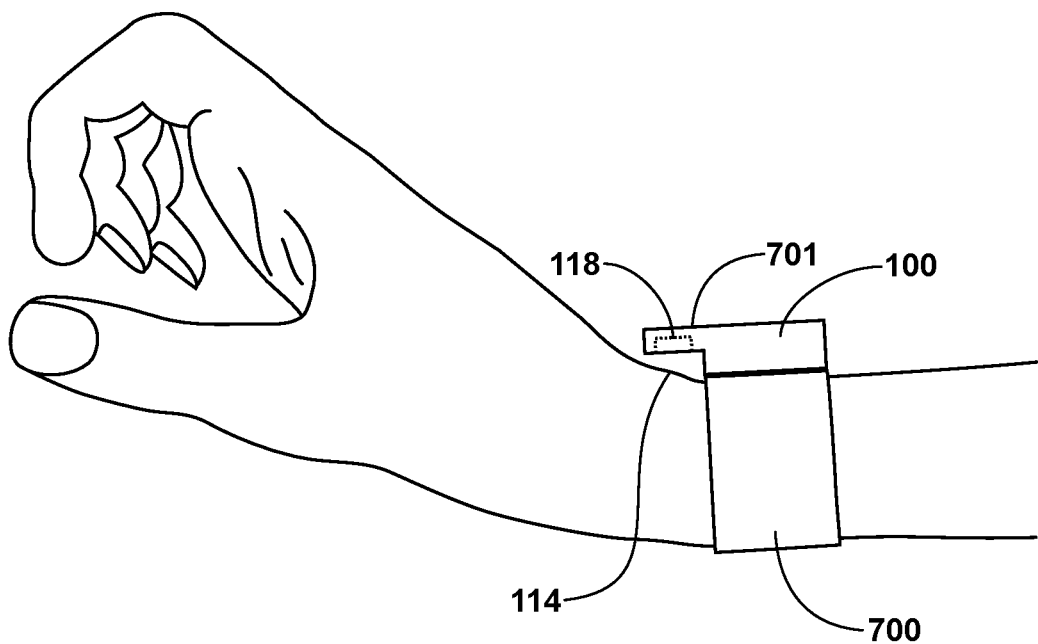
FIG. 8A is a graphical illustration of a decrease in the amount of separation between the capacitive proximity sensor and the wrist regions of the right hand and the right forearm as the right wrist joint of the user in FIG. 7 is extended.
Figure 8B:
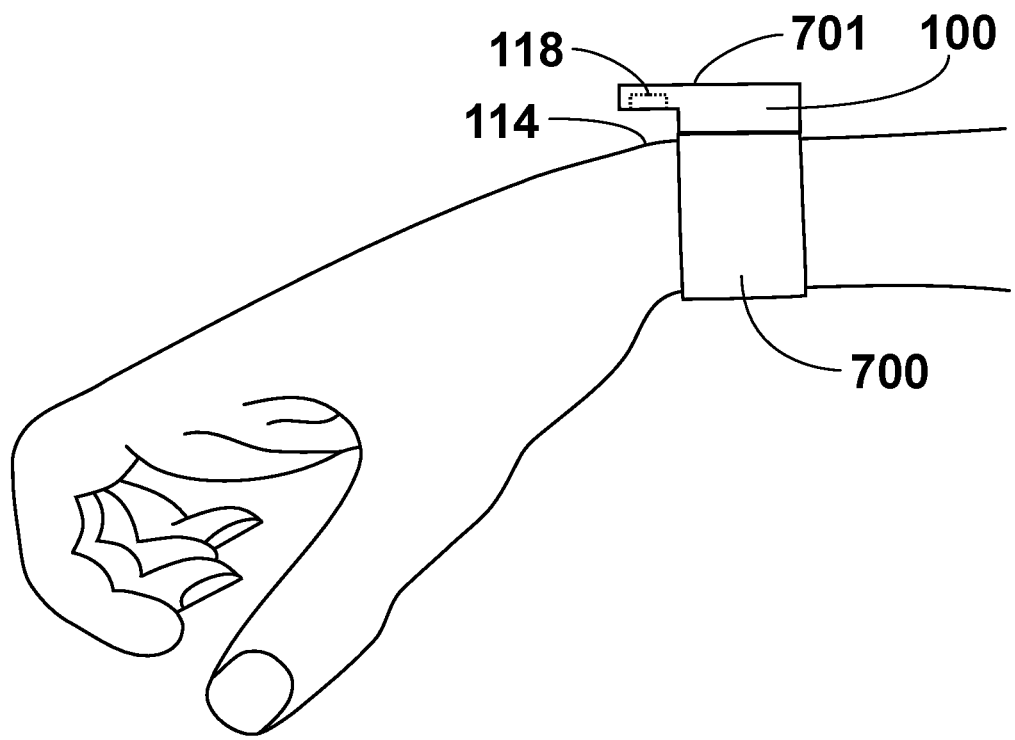
FIG. 8B is a graphical illustration of an increase in the amount of separation between the capacitive proximity sensor and the wrist regions of the right hand and the right forearm as the wrist joint of the user in FIG. 7 is flexed.

FIGS. 8A and 8B

FIG. 8A illustrates a decrease in the amount of separation 130 (in FIG. 1) between sensing plate 118 of capacitive proximity sensor 102 (in FIG. 1) and user's body target 114 (i.e. between capacitive proximity sensor 102 and user's body target 114) as the wrist region of the right forearm and the wrist region of the right hand become closer to sensing plate 118, with soft tissues at the top of the wrist regions bulging out, when the user extends the right wrist joint. The decrease in the amount of separation 130 results in an increase in capacitance of sensing pad 108 (in FIG. 1) on sensing plate 118 to ground, which is detected by capacitive proximity sensor 102. In FIG. 8A, although there is a small amount of separation 130 between sensing plate 118 and user's body target 114 when the right wrist joint of the user is extended, sensing plate 118 can touch (or almost touch) user's body target 114 to detect extension of the right wrist joint.

On the other hand, FIG. 8B illustrates an increase in the amount of separation 130 between sensing plate 118 and user's body target 114 as the wrist region of the right forearm and the wrist region of the right hand become farther away from sensing plate 118, with soft tissues at the wrist regions stretching out, when the user flexes the right wrist joint. The increase in the amount of separation 130 causes a decrease in capacitance of sensing pad 108 on sensing plate 118 to ground, which is detected by capacitive proximity sensor 102.

When a user performs a physical activity that involves the right wrist joint, such as waving, pushing, slapping, weight-lifting, one or more sensing plates can be incorporated in wearable joint-action sensor 100 to detect the activity, so long as capacitive proximity sensor 102 of wearable joint-action sensor 100 can detect the amount of separation 130 and the rate of change between sensing plate 118 and user's body target 114 as the right wrist joint performs the action.

Although FIGS. 7, 8A, and 8B illustrate that wearable joint-action sensor 100 inside housing 701 is worn on the wrist region of the right forearm of a user for detecting actions of the right wrist joint, wearable joint-action sensor 100 can be worn on the wrist region of the left forearm of the user for detecting actions of the left wrist joint by using the same detection principle. The same detection principle can also be used for sensing plate 118 of wearable joint-action sensor 100 located in the proximity of the user's palm of the right hand (the second body segment) and the wrist region of the right forearm (the first body segment, where a user wears wearable joint-action sensor 100), with both the first and second body segments (i.e. the region comprising both the first and second body segments) serving as user's body target 114 for sensing plate 118. Furthermore, the same detection principle can be used for detecting abduction and adduction of a wrist joint when sensing plate 118 of wearable joint-action sensor 100 is placed in the proximity of one side (or one sensing plate 118 on each side) of the wrist region of the hand and the wrist region of the forearm of a user.

Many common daily physical activities involve complex actions of a wrist joint, and wearable joint-action sensor 100 in the third embodiment can be used for detecting these physical activities involving a wrist joint by incorporating multiple sensing plates around the wrist joint (i.e. around the wrist regions of the wrist joint) of a user. For example, wearable joint-action sensor 100 with multiple sensing plates around a wrist joint can be used for detecting handwashing, so that the number, duration, and time of handwashing performed by the user can be recorded for monitoring the user's compliance in maintaining excellent personal hygiene. This is important if the user is a child, and is particularly important if the user is a physician, nurse, or healthcare provider. Wearable joint-action sensor 100 with multiple sensing plates around a wrist joint can detect the actions of the wrist joint during handwashing with water, soap, or any hand sanitizer. If running water is used for handwashing, another sensor, such as a sound transducer, water-droplet detector, or humidity sensor, can be added to further confirm detection of handwashing by sensing the sound (audible or inaudible) when water impacts the hand (or the wash sink) or when water exits the faucet, by detecting water droplets in the proximity of or in contact with the water-droplet detector, or by sensing an increase in humidity around a steam or pool of water, respectively.

Control of Computing Devices with Joint-Action Detection

FIG. 9

Figure 9:
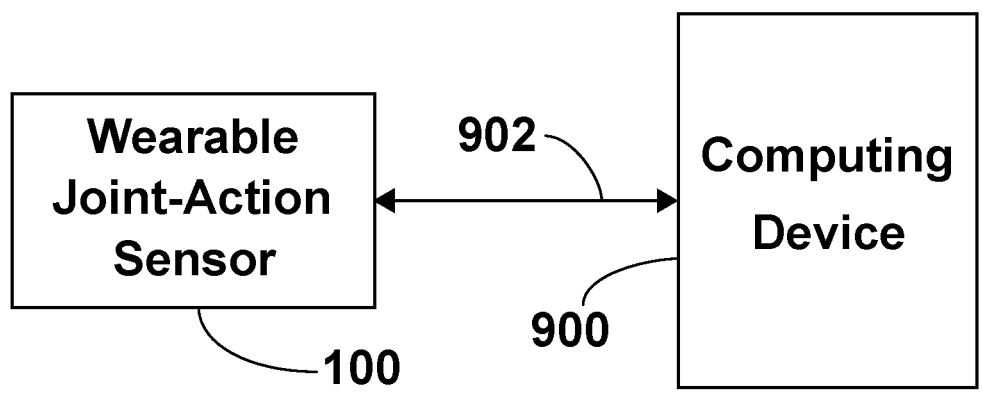
FIG. 9 is a block diagram showing schematically the communication between the wearable joint-action sensor and a computing device for controlling the operation of the computing device by using an action of a joint.

FIG. 9 shows a block diagram of a computing device 900 using wearable joint-action sensor 100 for controlling the operation of computing device 900. Computing device 900 can be a smartwatch, fitness wristband, smartphone, computer, or any device that has a CPU (central processing unit) or logic circuits (for performing logical operations), with an appropriate wired or wireless communication device, which can simply be an electrical cable, for communicating with wearable joint-action sensor 100. As illustrated in FIGS. 1, 2, and 9, wearable joint-action sensor 100 can detect actions of a joint and use its wired or wireless communication device 138 (in FIG. 1) and a signal link 902 for controlling computing device 900 by informing computing device 900 that a predetermined joint action is or has been detected. Signal link 902 can simply be a wired connection, such as electrical conductors or an electrical cable (for example, a Universal-Serial-Bus cable), or any wireless connection, such as a radio-frequency (for example, a Bluetooth®, Wi-Fi®, or near-field-communication connection), optical, or acoustic connection. Computing device 900 uses the received information of the joint action detected by wearable joint-action sensor 100 to determine its operation. On the other hand, computing device 900 can use its communication device (not shown in FIG. 9) and signal link 902 to download a computer program to embedded controller 132 (in FIG. 1), so that embedded controller 132 can execute the downloaded computer program for controlling the operation of wearable joint-action sensor 100.

For example, if computing device 900 is a smartphone, it can download an appropriate computer program to wearable joint-action sensor 100, so that wearable joint-action sensor 100 is programmed to inform computing device 900 when wearable joint-action sensor 100 detects a user waving the right hand by flexing and extending the right wrist joint alternately. Based on the received information of the joint action or actions detected by wearable joint-action sensor 100, computing device 900 can perform a predetermined operation, such as turning on or off its display, playing back a voice recorded message, or receiving or terminating a phone call.

When wearable joint-action sensor 100 is used for controlling computing device 900, wearable joint-action sensor 100 can be incorporated in the housing of computing device 900 and communicate with computing device 900 by a bus (for example, an inter-integrated circuit bus or a serial peripheral interface bus) if computing device 900 is also a wearable device, such as a smartwatch or fitness wristband. In this case, sensing plate 118 of wearable joint-action sensor 100 can be incorporated on the bottom of the housing of computing device 900 in the proximity of the wrist region of the hand (or the palm of the hand, if computing device 900 is worn at the bottom of the wrist) and the wrist region of the right forearm. Based on the received information of the joint action or actions detected by wearable joint-action sensor 100, computing device 900 can perform a predetermined operation, such as turning on or off its display of time, reporting time audibly, or recording an audio message. It should be noted that sensing plate 118 can be incorporated on the side, instead of the bottom, of the housing of computing device 900 that faces the hand if wearable joint-action sensor 100 only detects extension of the wrist joint (or flexion of the wrist joint, if computing device 900 is worn at the bottom of the wrist). Alternatively, wearable joint-action sensor 100 can be physically separated from computing device 900 and use its wired or wireless communication device 138 and signal link 902 to communicate with computing device 900. For example, wearable joint-action sensor 100 can use USB (Universal Serial Bus), Bluetooth®, Wi-Fi®, NFC (near-field communication), or any radio-frequency, optical, or acoustic communication to control computing device 900, such as a smartphone or computer, which can be nearby or far away from wearable joint-action sensor 100.

In FIG. 9, computing device 900 can be controlled by any of the embodiments, not just the third embodiment for the wrist joint. For example, when wearable joint-action sensor 100 is used for detecting abduction and adduction of the right shoulder joint, as discussed in the second embodiment, computing device 900 can increase the volume of recorded music being played back after receiving information from wearable joint-action sensor 100, indicating that the user has raised the right arm by abducting the right shoulder joint. Furthermore, when wearable joint-action sensor 100 is used for detecting flexion and extension of a finger joint, as discussed in the sixth embodiment, wearable joint-action sensor 100, each worn on a finger of one or both hands of a user (in FIG. 16), can be used by the user to perform complex control of computing device 900, such as an electronic piano (or any electronic music instrument), electronic game console, or computer, when it is located far away from the user, or when there is no physical keyboard or control panel for the electronic piano (or any electronic music instrument), electronic game console, or computer.

FIG. 10

Fourth Embodiment

Figure 10:
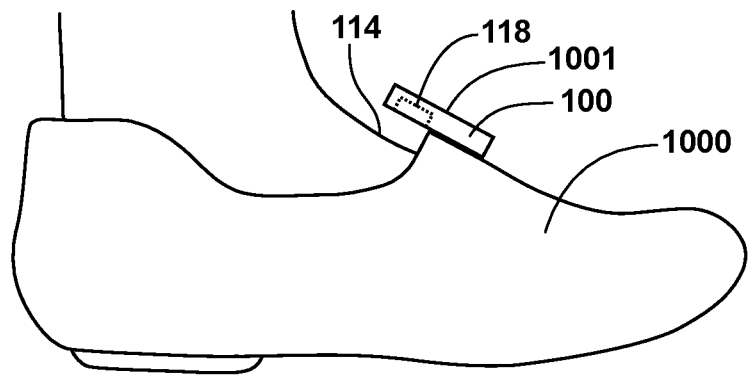
FIG. 10 is a graphical illustration of a possible location of the wearable joint-action sensor for detecting actions of the right ankle joint of a user in accordance with the fourth embodiment.

A fourth embodiment of the wearable joint-action sensor is illustrated in FIG. 10. FIG. 10 is a side view of wearable joint-action sensor 100 inside a housing 1001 mounted on the instep of a right footwear 1000 that is worn on the right foot (the right foot is the first body segment in this embodiment) by a user (a human being in this embodiment) for detecting joint actions, such as flexion (plantar flexion) and extension (dorsiflexion), of the right ankle joint, which links the right foot to the ankle region of the right lower leg (the right lower leg is the second body segment in this embodiment) of the user. Wearable joint-action sensor 100 inside housing 1001 incorporates sensing plate 118, which is illustrated by a dotted outline. Sensing plate 118 of wearable joint-action sensor 100 is in the proximity of the instep of the right foot, and the instep of the right foot (the first body segment) serves as user's body target 114 for sensing plate 118. When compared with prior-art instep sensors that are constructed with strain transducers, piezoelectric elements, or switches, the fourth embodiment of the wearable joint-action sensor is more reliable and durable because there is no wear and tear of the mechanical parts after repeated use.

Wearable joint-action sensor 100 inside housing 1001 can be attached to the instep of right footwear 1000 by using a mounting clip. Wearable joint-action sensor 100 can also be attached to the instep of right footwear 1000 by any other mechanism, such as by sewing, or by using any type of magnetic, adhesive, or adhering device. Furthermore, wearable joint-action sensor 100 inside housing 1001 can be attached directly, such as by adhesive or adhesive tape, to the right foot of a user without using right footwear 1000. As illustrated in FIG. 10, there is an appropriate separation 130 (in FIG. 1) between sensing plate 118 and user's body target 114 when the right ankle joint is not flexed or extended.

Although only one sensing plate 118 is illustrated in FIG. 10, multiple sensing plates can be incorporated in wearable joint-action sensor 100 to obtain more separation data for the instep of the right foot as the user flexes or extends the right ankle joint. Wearable joint-action sensor 100 with multiple sensing plates can facilitate obtaining appropriate separation data for the instep of the right foot even when a user does not wear wearable joint-action sensor 100 exactly as directed, because in this case some of the sensing plates could still be located at an appropriate proximity of the instep of the right foot for detecting actions of the right ankle joint of the user.

Joint-Action Detection Operation

Figure 11A:
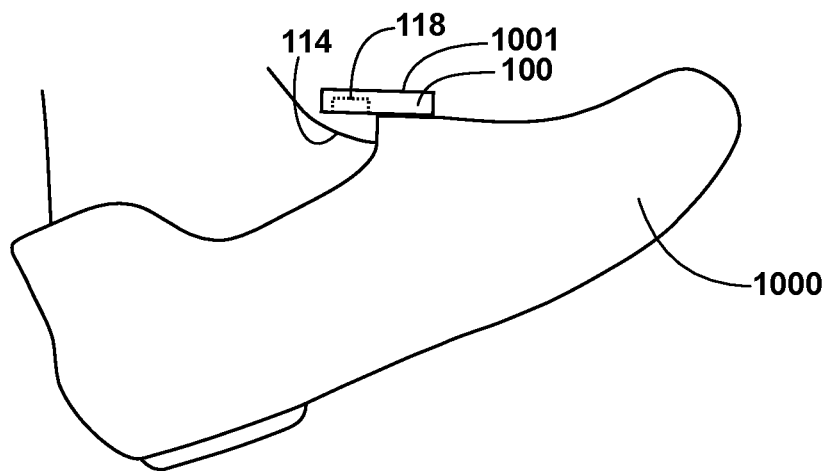
FIG. 11A is a graphical illustration of a decrease in the amount of separation between the capacitive proximity sensor and the instep of the right foot as the right ankle joint of the user in FIG. 10 is extended (dorsiflexion).
Figure 11B:
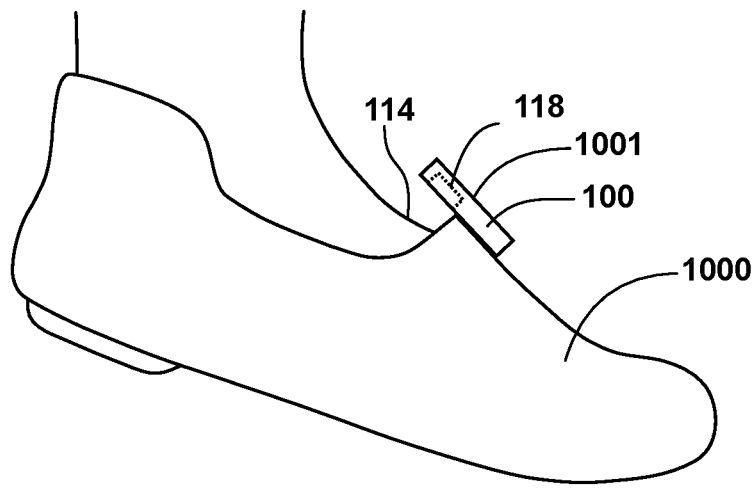
FIG. 11B is a graphical illustration of an increase in the amount of separation between the capacitive proximity sensor and the instep of the right foot as the right ankle joint of the user in FIG. 10 is flexed (plantar flexion).

FIGS. 11A and 11B

FIG. 11A illustrates a decrease in the amount of separation 130 (in FIG. 1) between sensing plate 118 of capacitive proximity sensor 102 (in FIG. 1) and user's body target 114 (i.e. between capacitive proximity sensor 102 and user's body target 114) as the instep of the right foot becomes closer to sensing plate 118, with soft tissue at the instep of the right foot bulging out, when the user extends the right ankle joint. The decrease in the amount of separation 130 results in an increase in capacitance of sensing pad 108 on sensing plate 118 to ground, which is detected by capacitive proximity sensor 102. In FIG. 11A, although there is a small amount of separation 130 between sensing plate 118 and user's body target 114 when the right ankle joint of the user is extended, sensing plate 118 can touch (or almost touch) user's body target 114 for detecting extension of the right ankle joint.

On the other hand, FIG. 11B illustrates an increase in the amount of separation 130 between sensing plate 118 and user's body target 114 as the instep of the right foot becomes farther away from sensing plate 118, with soft tissue at the instep of the right foot stretching out when the user flexes the right ankle joint. The increase in the amount of separation 130 causes a decrease in capacitance of sensing pad 108 on sensing plate 118 to ground, which is detected by capacitive proximity sensor 102.

When a user performs a physical activity that involves the right ankle joint, such as kicking, tip toeing, walking, or running, one or more sensing plates can be incorporated in wearable joint-action sensor 100 to detect the activity, so long as capacitive proximity sensor 102 of wearable joint-action sensor 100 can detect the amount of separation 130 and the rate of change between sensing plate 118 and user's body target 114 at the instep of the right foot as the right ankle joint performs the action.

Although FIGS. 10, 11A, and 11B illustrate that wearable joint-action sensor 100 inside housing 1001 is worn on the instep of right footwear 1000 of the user for detecting actions of the right ankle joint, wearable joint-action sensor 100 can be worn on the instep of the left footwear of the user for detecting actions of the left ankle joint by using the same detection principle. The same detection principle can also be used for detecting internal rotation and external rotation of an ankle joint when sensing plate 118 of wearable joint-action sensor 100 is located on one side (or one sensing plate 118 on each side) of the footwear in the proximity of a user's foot and appropriately separated from the user's foot.

FIG. 12

Fifth Embodiment

Figure 12:
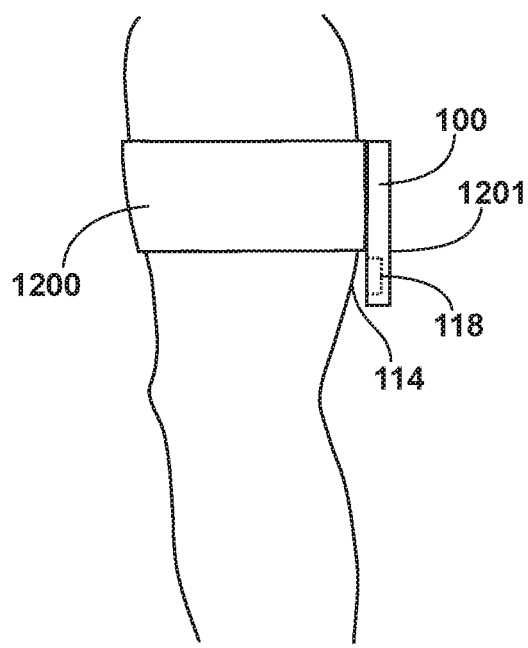
FIG. 12 is a graphical illustration of a possible location of the wearable joint-action sensor for detecting actions of the right elbow joint of a user in accordance with the fifth embodiment.

A fifth embodiment of the wearable joint-action sensor is illustrated in FIG. 12. FIG. 12 is a side view of wearable joint-action sensor 100 inside a housing 1201 worn on the right upper arm (the right upper arm is the first body segment in this embodiment) of a user (a human being in this embodiment) with an armband 1200 for detecting joint actions, such as flexion and extension, of the right elbow joint of the user. Wearable joint-action sensor 100 inside housing 1201 incorporates sensing plate 118, which is illustrated by a dotted outline. Armband 1200 is preferably made of an elastic material, although other types of materials can also be used, so long as armband 1200 can hold wearable joint-action sensor 100 in an appropriate location on the right upper arm when the muscles of the right upper arm change their shapes during flexion and extension of the right elbow joint, which links the right upper arm to the right forearm (the right forearm is the second body segment in this embodiment). Sensing plate 118 of wearable joint-action sensor 100 is in the proximity of the user's right upper arm (the first body segment) above the elbow pit (antecubital fossa), which serves as user's body target 114 for sensing plate 118.

Wearable joint-action sensor 100 inside housing 1201 can be attached to armband 1200 by using a mounting clip, or it can be attached to armband 1200 by any other mechanism, such as by sewing, or by using any type of magnetic, adhesive, or adhering device. Furthermore, wearable joint-action sensor 100 inside housing 1201 can also be attached directly, such as by adhesive or adhesive tape, to the upper arm of a user without using armband 1200. Although FIG. 12 shows a small amount of separation 130 between sensing plate 118 and user's body target 114 when the user's right elbow joint is fully extended, sensing plate 118 can touch (or almost touch) user's body target 114 to detect full extension, or any degree of extension, of the right elbow joint.

Although only one sensing plate 118 is illustrated in FIG. 12, multiple sensing plates can be incorporated in wearable joint-action sensor 100 to obtain more separation data for the right upper arm above the elbow pit as the user flexes or extends the right elbow joint. Wearable joint-action sensor 100 with multiple sensing plates can also facilitate obtaining appropriate separation data for the right upper arm above the elbow pit even when a user does not wear wearable joint-action sensor 100 exactly as directed, because in this case some of the sensing plates could still be located at an appropriate proximity of the right upper arm above the elbow pit for detecting actions of the right elbow joint of the user.

Joint-Action Detection Operation

FIG. 13

Figure 13:
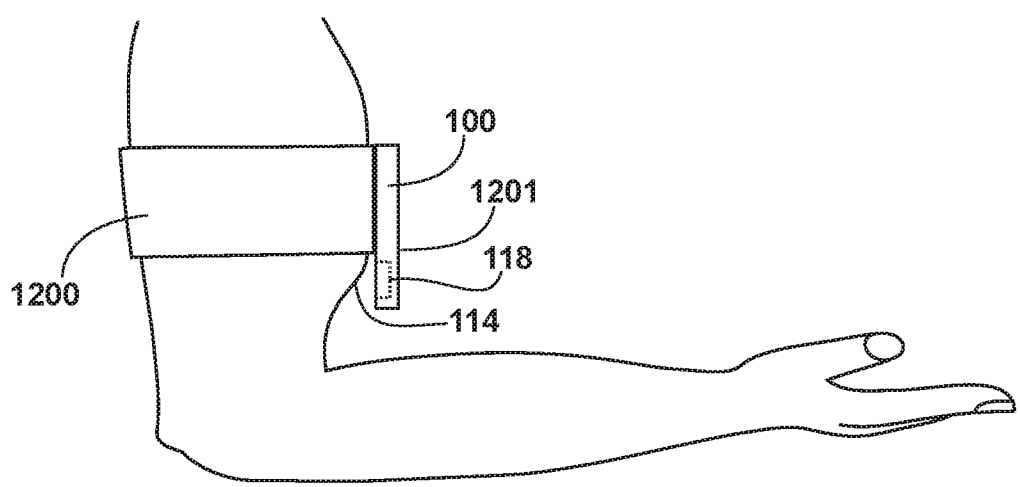
FIG. 13 is a graphical illustration of an increase in the amount of separation between the capacitive proximity sensor and the right upper arm above the elbow pit as the right elbow joint of the user in FIG. 12 is flexed.

FIG. 13 illustrates an increase in the amount of separation 130 (in FIG. 1) between sensing plate 118 of capacitive proximity sensor 102 (in FIG. 1) and user's body target 114 (i.e. between capacitive proximity sensor 102 and user's body target 114) as the biceps muscle of the right upper arm bulges out when the user flexes the right elbow joint. The increase in the amount of separation 130 results in a decrease in capacitance of sensing pad 108 (in FIG. 1) on sensing plate 118 to ground, which is detected by capacitive proximity sensor 102.

When a user performs a physical activity that involves the right elbow joint, such as lifting, stretching, or punching, one or more sensing plates can be incorporated in wearable joint-action sensor 100 to detect the activity, so long as capacitive proximity sensor 102 of wearable joint-action sensor 100 can detect the amount of separation 130 and the rate of change between sensing plate 118 and user's body target 114 on the right upper arm above the elbow pit as the right elbow joint performs the action.

Although FIGS. 12 and 13 illustrate that wearable joint-action sensor 100 inside housing 1201 is worn on the right upper arm of the user for detecting actions of the right elbow joint, wearable joint-action sensor 100 can be worn on the left upper arm of the user for detecting actions of the left elbow joint by using the same detection principle. Furthermore, the user's right forearm (the second body segment) instead of the right upper arm (the first body segment) can serve as user's body target 114 for detecting actions of the right elbow joint. In this case, wearable joint-action sensor 100 can be worn on the right upper arm just above the elbow pit with sensing pad 108 on sensing plate 118 in the proximity of the right forearm (instead of the right upper arm) to detect the amount of separation 130 between sensing plate 118 and the right forearm as the user flexes the right elbow joint. Alternatively, wearable joint-action sensor 100 can use an active infrared proximity sensor, which typically has a longer sensing range than a capacitive proximity sensor, for sensing the separation between the active infrared proximity sensor (which is worn on the right upper arm) and the right forearm. The operation of the active infrared proximity sensor for detecting the degree of flexion of the right elbow joint is similar to the operation of active infrared proximity sensor 2004 (in FIGS. 20A, 21A, and 21B) for detecting the degree of flexion of the right hip joint in the eighth embodiment.

FIG. 14

Sixth Embodiment

Figure 14:
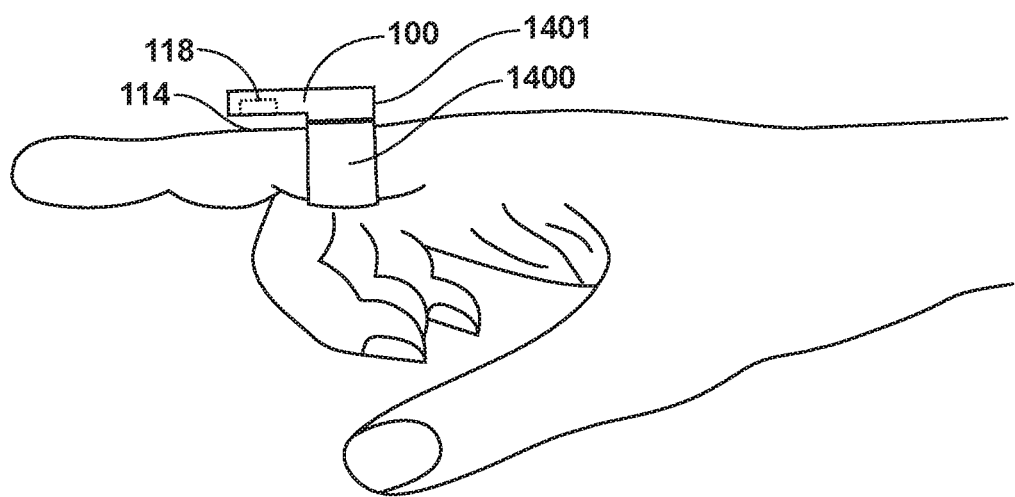
FIG. 14 is a graphical illustration of a possible location of the wearable joint-action sensor for detecting actions of the first finger joint (the proximal interphalangeal joint) of the right index finger of a user in accordance with the sixth embodiment.

A sixth embodiment of the wearable joint-action sensor is illustrated in FIG. 14. FIG. 14 is a side view of wearable joint-action sensor 100 inside a housing 1401 worn on the first segment (the proximal phalanx, which is the first body segment in this embodiment) of the right index finger of a user (a human being in this embodiment), with a ring 1400 for detecting joint actions, such as flexion and extension, of the first finger joint (the proximal interphalangeal joint) of the right index finger of the user. Wearable joint-action sensor 100 inside housing 1401 incorporates sensing plate 118, which is illustrated by a dotted outline. Sensing plate 118 of wearable joint-action sensor 100 is in the proximity of the first segment and the second segment (the middle phalanx, which is the second body segment in this embodiment) of the right index finger near the first finger joint, which links the first segment to the second segment of the right index finger. Both the first segment and the second segment of the right index finger (i.e. the region comprising both the first and second body segments) serve as user's body target 114 for sensing plate 118.

Wearable joint-action sensor 100 inside housing 1401 can be attached to ring 1400 by using a mounting clip, or it can be attached to ring 1400 by any other mechanism, such as by sewing (if ring 1400 is made of a fabric material), or by using any type of magnetic, adhesive, or adhering device. Furthermore, wearable joint-action sensor 100 inside housing 1401 can also be attached directly, such as by adhesive or adhesive tape, to the first segment of the right index finger of a user without using ring 1400. In FIG. 14, although there is a small amount of separation 130 between sensing plate 118 and user's body target 114 when the first finger joint of the user's right index finger is fully extended, sensing plate 118 can touch (or almost touch) user's body target 114 for detecting extension of the first finger joint.

Although only one sensing plate 118 is illustrated in FIG. 14, multiple sensing plates can be incorporated in wearable joint-action sensor 100 to obtain more separation data for the region comprising both the first and second segments of the right index finger near the first finger joint of the right index finger as the user flexes or extends the first finger joint. Wearable joint-action sensor 100 with multiple sensing plates can also facilitate obtaining appropriate separation data for the region comprising both the first and second segments of the right index finger near the first finger joint even when a user does not wear wearable joint-action sensor 100 exactly as directed, because in this case some of the sensing plates could still be located at an appropriate proximity of the region comprising both the first and second segments of the right index finger near the first finger joint for detecting actions of the first finger joint of the right index finger.

Joint-Action Detection Operation

FIG. 15

Figure 15:
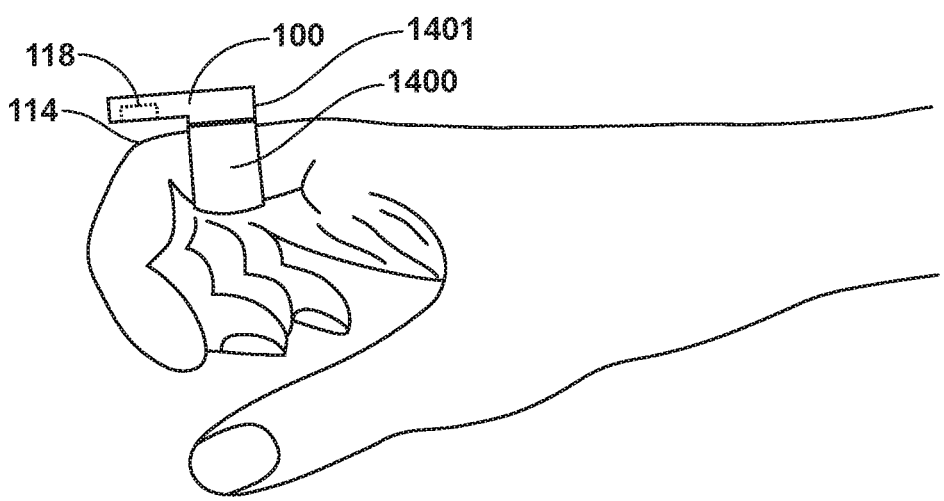
FIG. 15 is a graphical illustration of an increase in the amount of separation between the capacitive proximity sensor and the right index finger near the first finger joint as the first finger joint of the right index finger of the user in FIG. 14 is flexed.

FIG. 15 illustrates an increase in the amount of separation 130 (in FIG. 1) between sensing plate 118 of capacitive proximity sensor 102 (in FIG. 1) and user's body target 114 (i.e. between capacitive proximity sensor 102 and user's body target 114) as the user flexes the first finger joint of the right index finger. During this movement, soft tissues at the top of the first and second segments of the right index finger near the first finger joint stretch out. The increase in the amount of separation 130 results in a decrease in capacitance of sensing pad 108 (in FIG. 1) on sensing plate 118 to ground, which is detected by capacitive proximity sensor 102.

When the user performs a physical activity that involves the first finger joint of the right index finger, such as typing, flicking, or pointing, one or more sensing plates can be incorporated in wearable joint-action sensor 100 to detect the activity, so long as capacitive proximity sensor 102 of wearable joint-action sensor 100 can detect the amount of separation 130 and the rate of change between sensing plate 118 and user's body target 114 near the first finger joint of the right index finger as the first finger joint performs the action.

In FIG. 14, sensing plate 118 of wearable joint-action sensor 100 is in the proximity of the first and second segments of the right index finger near the first finger joint, and both the first and second segments of the right index finger (i.e. the region comprising both the first and second body segments) serve as user's body target 114 for sensing plate 118. If sensing plate 118 is placed on top of the second segment of the right index finger (by using a different design of housing 1401) and is distant from the first segment of the right index finger, then only the second segment of the right index finger (i.e. only the second body segment) serves as user's body target 114, because there is insignificant change in the separation between sensing plate 118 and the first segment of the right index finger (i.e. the first body segment) when the extended first finger joint is flexed. In this arrangement, the capacitance contribution of the first body segment for detecting the separation is insignificant, because the relatively constant capacitance to ground of the first body segment contributes to the total base capacitance instead. This illustrates the fact that when both the first and second body segments (i.e. when a region comprising both the first and second body segments) serve as user's body target 114 in any embodiment, one of the two body segments can dominate or even completely control the detection of separation 130 (i.e. the capacitance that represents separation 130) for detecting actions of the joint that links the first body segment to the second body segment.

Although FIG. 15 illustrates that wearable joint-action sensor 100 inside housing 1401 is worn on the first segment of the right index finger of a user for detecting actions of the first finger joint of the right index finger, wearable joint-action sensor 100 can be worn on the first segment of the left index finger of a user for detecting actions of the first finger joint of the left index finger by using the same detection principle. In fact, wearable joint-action sensor 100 can be worn on the first segment (the proximal phalanx), the second segment (the middle phalanx), or the third segment (the distal phalanx) of any finger of a user, including the thumb (which has only two segments; the proximal and distal phalanxes), to detect any action of any finger joint, such as the joint at the base of a finger (the metacarpophalangeal joint), the first finger joint (the proximal interphalangeal joint), or the second finger joint (the distal interphalangeal joint). For example, wearable joint-action sensor 100 can be worn on the first segment of a thumb for detecting a thumbs-up action of the first finger joint of the thumb.

Furthermore, by using a similar detection principle, wearable joint-action sensor 100 can be worn on the thigh above a knee cap or on the lower leg below a knee cap with an athletic knee brace for detecting actions of the knee joint, which links the thigh of the upper leg to the lower leg, because the actions of a knee joint and those of the first finger joint of a finger are very similar. When wearable joint-action sensor 100 is worn on the thigh of the upper leg above the knee cap, the thigh of the upper leg is the first body segment and the lower leg is the second body segment, and the thigh of the upper leg (the first body segment) is user's body target 114 for sensing plate 118. Separation 130 (in FIG. 1) between sensing plate 118 and the thigh decreases when the knee joint is extended, because the soft tissue of the thigh above the knee cap (such as the quadriceps tendon) bulges out. Likewise, separation 130 between sensing plate 118 and the thigh increases when the knee joint is flexed, because the soft tissue of the thigh above the knee cap stretches out. On the other hand, if wearable joint-action sensor 100 is worn on the lower leg below the knee cap, the lower leg becomes the first body segment and the thigh of the upper leg becomes the second body segment, and the lower leg (the first body segment) becomes user's body target 114 for sensing plate 118. Separation 130 between sensing plate 118 and the lower leg decreases when the knee joint is extended, because the soft tissue of the lower leg below the knee cap (such as the patellar ligament) bulges out. Likewise, separation 130 between sensing plate 118 and the lower leg increases when the knee joint is flexed, because the soft tissue of the lower leg below the knee cap stretches out.

The detection principle for detecting actions of the knee joint can also be used for detecting actions of an elbow joint (i.e. an alternative for the fifth embodiment for the right elbow joint) that links an upper arm to a forearm. In this case, wearable joint-action sensor 100 can be worn on the upper arm above the olecranon (the bony prominence of the elbow) or on the forearm below the olecranon with an athletic elbow brace, and the upper arm or the forearm serves as user's body target 114, respectively. The soft tissues around the olecranon bulge out when the elbow joint is extended, and the soft tissues around the olecranon stretch out when the elbow joint is flexed, so the decrease and increase in separation 130 between sensing plate 118 and the soft tissues can be used for detecting extension and flexion of the elbow joint, respectively.

As discussed in the third embodiment and illustrated in FIG. 9, wearable joint-action sensor 100 of the sixth embodiment or of any embodiment can also be used for controlling a computing device, such as a smartwatch, fitness wristband, smartphone, or computer. In the prior arts, a capacitive touch sensor (i.e. a capacitive proximity sensor adjusted to a very short range) is used for controlling a computing device by using the tip of a finger to touch a capacitive sensing pad. Instead of using the prior-art approach for controlling a computing device, wearable joint-action sensor 100 is worn on the first body segment for detecting an action of a joint that links the first body segment to the second body segment with a proximity sensor. The proximity sensor detects a separation between the proximity sensor and the first body segment, the second body segment, or both the first and second body segments (i.e. the region comprising both the first and second body segments), for detecting the joint action, which is used for controlling a computing device. This approach for controlling a computing device does not require a user to use the tip of a finger to touch a capacitive sensing pad, as required by the prior-art approach. For example, as illustrated in FIGS. 14 and 15, flexion of the first finger joint of the right index finger, with wearable joint-action sensor 100 worn on the first segment of the right index finger, can be used for controlling a computing device, without requiring a user to touch sensing pad 108 on sensing plate 118 (in FIG. 1) with the tip of any finger.

Using wearable joint-action sensor 100 to control a computing device is a compact and efficient control mechanism, because an action of just a single joint, with wearable joint-action sensor 100 worn on one of the two body segments linked by the joint, is used to control a computing device. For example, wearable joint-action sensor 100 in the sixth embodiment can be used for unlocking a secured computing device, such as a smartphone or a computer, or for sending a secured passcode to a computer program running on a computing device by using communication device 138 to transmit a joint-action signature of the first finger joint of the right index finger to the computing device. The joint-action signature is created by a sequence of actions (i.e. flexion and extension) of the first finger joint of the right index finger, and each action has a predetermined degree of action and duration that a user typically uses, resembling a signature by the user. The computing device can use a timer (a microprocessor usually incorporates at least one timer) and a software or hardware comparator to decode and verify the joint-action signature when the sequence of joint actions, which also includes the degree of each joint action, is received from wearable joint-action sensor 100. Furthermore, as discussed below, when wearable joint-action sensor 100 is worn on each finger of both hands of a user, an action of a joint of each finger can be used for controlling a computing device, without requiring the user to touch sensing pad 108 on sensing plate 118 with the tip of any finger.

Complex Control of a Computing Device with Multiple Joint-Action Detections

FIG. 16

Figure 16:
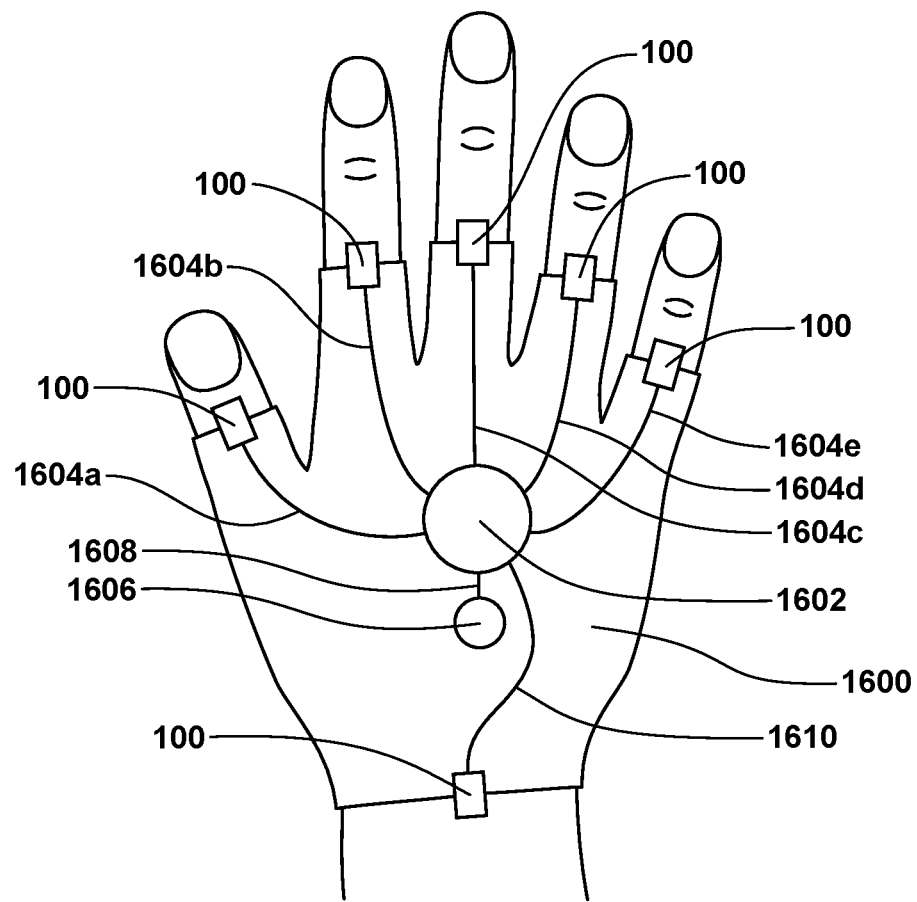
FIG. 16 is a graphical illustration of using a glove for attaching the wearable joint-action sensor in the proximity of the wrist joint and in the proximity of each of the first finger joints of the fingers of the right hand of a user.

FIG. 16 illustrates wearable joint-action sensor 100 inside a housing (housings are not illustrated with reference numerals in FIG. 16 for simplicity) worn in the proximity of the first finger joint of each finger of the right hand of a user for detecting flexion and extension of the first finger joint. A glove 1600 that encloses most of the first segment (the proximal phalanx) of each finger is used for attaching each wearable joint-action sensor 100 in the proximity of a first finger joint, with sensing plate 118 underneath wearable joint-action sensor 100 (the side view is similar to that shown in FIG. 14). In FIG. 16, sensing plate 118 and body target 114 are not illustrated because they are not visible from the top of wearable joint-action sensor 100. FIG. 16 also illustrates wearable joint-action sensor 100 worn on the wrist region of the right hand of the user with glove 1600 for detecting flexion and extension of the right wrist joint. The operation of wearable joint-action sensor 100 attached to glove 1600 at the wrist region of the hand for detecting flexion and extension of the right wrist joint is similar to that of wearable joint-action sensor 100 in the third embodiment, except that wearable joint-action sensor 100 is attached to glove 1600 at the wrist region of the right hand (the right hand is the first body segment in this case) with sensing plate 118 in the proximity of the wrist regions of the right hand and the right forearm (the right forearm is the second body segment in this case) as shown in FIG. 16, instead of attached to the wrist region of the right forearm with wristband 700 as shown in FIG. 7.

Wearable joint-action sensor 100 can be attached to glove 1600 by using a mounting clip, or it can be attached to glove 1600 by any other mechanism, such as by sewing, or by using any type of magnetic, adhesive, or adhering device. Furthermore, wearable joint-action sensor 100 can also be attached directly, such as by adhesive or adhesive tape, to the right hand of a user without using glove 1600.

FIG. 16 shows that wearable joint-action sensor 100 in the proximity of the first finger joint of each finger communicates with a sensing hub 1602 with an electrical cable 1604a, 1604*b*, 1604*c*, 1604*d*, or 1604*e*, and wearable joint-action sensor 100 in the proximity of the right wrist joint communicates with sensing hub 1602 with an electrical cable 1610. Sensing hub 1602 can be an embedded controller that serves each wearable joint-action sensor 100. Sensing hub 1602 uses an electrical connection 1608 to connect to a communication device 1606 for communicating with a computing device (not shown in FIG. 16), such as an electronic piano (or any electronic music instrument), electronic game console, smartwatch, fitness wristband, smartphone, or computer. Sensing hub 1602 and communication device 1606 can be incorporated in the same housing instead of being separated as shown in FIG. 16. Communication device 1606, such as a USB (Universal Serial Bus), Bluetooth®, Wi-Fi®, or NFC (near-field communication) device, an electrical cable, or any radio-frequency, optical, acoustic, or wired communication device, provides wired or wireless communication for sensing hub 1602 to communicate with the computing device. Wearable joint-action sensor 100 can also use communication device 138 (in FIG. 1) to communicate with sensing hub 1602 wirelessly, instead of using electrical cable 1604*a*, 1604*b*, 1604*c*, 1604*d*, 1604*e*, or 1610.

Sensing hub 1602 can perform some or all of the function of embedded controller 132 (in FIG. 1) of wearable joint-action sensor 100, so that the hardware in wearable joint-action sensor 100 can be reduced. For example, capacitive proximity sensor 102 (in FIG. 1) in wearable joint-action sensor 100 can communicate directly with sensing hub 1602, which can be an embedded controller, so that embedded controller 132 is not needed in wearable joint-action sensor 100. In addition, electrical power can be delivered to wearable joint-action sensor 100 from a battery (not shown in FIG. 16) in sensing hub 1602 through electrical cable 1604*a*, 1604*b*, 1604*c*, 1604*d*, 1604*e*, or 1610, so that a battery is not needed in wearable joint-action sensor 100. Hardware in wearable joint-action sensor 100 can be further reduced by moving its capacitive proximity sensor 102 to sensing hub 1602, which can have capacitive proximity sensor 102 with multiple channels for proximity sensing, so that only sensing plate 118 is needed in wearable joint-action sensor 100.

Although FIG. 16 illustrates wearable joint-action sensor 100 worn on the right hand of a user with glove 1600, wearable joint-action sensor 100 can be worn on the left hand of a user with a glove that is similar to (such as a mirror image of) glove 1600. Furthermore, glove 1600 can be designed for attaching wearable joint-action sensor 100 near any joint of a finger, including the second finger joint (the distal interphalangeal joint) or the finger joint at the base of a finger (the metacarpophalangeal joint), to detect actions of the joint of the finger.

Complex control of a computing device, such as an electronic piano (or any electronic music instrument), electronic game console, or computer, can be performed by a combination of the degrees of flexions or extensions of the first finger joints of all the fingers of a user, and optionally the degree of flexion or extension of the wrist joint of the user. For example, if the left hand of a user also wears a glove that is similar to (such as a mirror image of) glove 1600, the user can play an electronic piano (or any electronic music instrument) or electronic game console, provide typing input to a computer that is far away from the user, or provide input when there is no physical keyboard or control panel for the electronic piano (or any electronic music instrument), electronic game console, or computer.

For detecting actions of a joint of a toe, a sock that has all or part of the toe exposed can be used for attaching wearable joint-action sensor 100 in the proximity of the joint of the toe. For example, a sock with an entire big toe exposed can be used for attaching wearable joint-action sensor 100 in the proximity of the big-toe joint at the base of the big toe (the metatarsophalangeal joint) for detecting flexion and extension of the big-toe joint. In fact, wearable joint-action sensor 100 can be attached to a sock or glove (such as an elastic surgical glove) that does not expose a toe or finger, respectively, so long as the sock or glove is made of a flexible material or has extra space near a joint that can facilitate an increase in separation between sensing plate 118 and user's body target 114 near the joint, so that flexion and extension of the joint can be detected. An elastic surgical glove with wearable joint-action sensor 100 attached in the proximity of one or more finger joints can allow a surgeon who wears the surgical glove to control a surgical assistance robot during a surgery.

Figure 17:
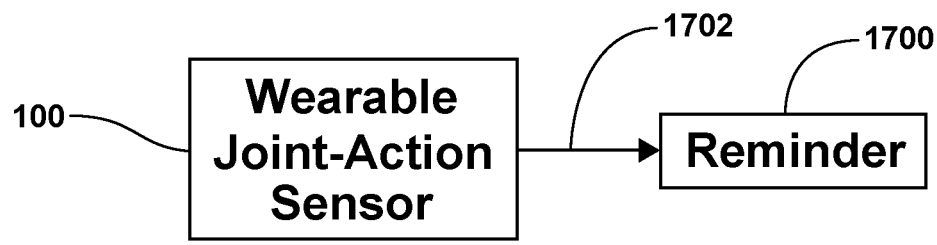
FIG. 17 is a block diagram showing schematically the wearable joint-action sensor communicating with a reminder in accordance with the seventh embodiment.
Figure 18:
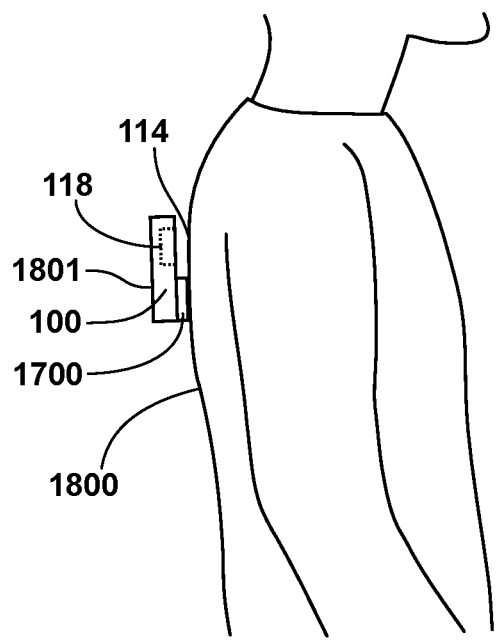
FIG. 18 is a graphical illustration of a possible location of the wearable joint-action sensor for detecting actions of the upper spinal column of a user in accordance with the seventh embodiment.

FIGS. 17 and 18

Seventh Embodiment

A seventh embodiment of the wearable joint-action sensor is illustrated in FIGS. 17 and 18. FIG. 17 shows wearable joint-action sensor 100 using its communication device 138 (in FIG. 1) and a signal link 1702 to communicate with a reminder 1700, which can be a voice recorder, vibrator, beeper, display, or simply a light-emitting diode (LED), for reminding or notifying a user or someone else (such as a caregiver of the user) that a predetermined joint action is or has been detected. Depending on the type of communication device 138, signal link 1702 can be simply electrical conductors or an electrical cable, or any wired or wireless connection, such as USB (Universal Serial Bus), Bluetooth®, Wi-Fi®, or NFC (near-field communication) connection, or any radio-frequency, optical, or acoustic connection.

FIG. 18 is a side view of wearable joint-action sensor 100 inside a housing 1801 and reminder 1700 worn on a shirt 1800 on top of the upper spinal column of a user (a human being in this embodiment) for detecting flexion and extension of the upper spinal column of the user. Wearable joint-action sensor 100 inside housing 1801 incorporates sensing plate 118, which is illustrated by a dotted outline. Although FIG. 18 shows that reminder 1700 (housing of reminder 1700 is not illustrated with a reference numeral in FIGS. 18 and 19 for simplicity) is separated from housing 1801 of wearable joint-action sensor 100, reminder 1700 can be incorporated in housing 1801 of wearable joint-action sensor 100, and signal link 1702 (in FIG. 17) can be a bus, such as an inter-integrated circuit bus or a serial peripheral interface bus, or simply electrical conductors.

A spinal column has many facet joints that link the vertebrae of the spinal column together and give them the flexibility to move against each other as the spinal column flexes (bends forward) or extends (bends backward). In this embodiment, each vertebra or section of the spinal column (i.e. a section of vertebrae), including the soft tissue around the section of the spinal column, is treated as a body segment, with the body segments linked by the facet joints. For this reason, flexion or extension of a section of the spinal column involves actions of many facet joints, not just an action of one facet joint. During flexion or extension of a section of the spinal column, the type of joint action (i.e. the type of facet-joint movement) of all the facet joints in the section of the spinal column is the same, although the degrees of the joint action (i.e. the amount of facet-joint movement) of the facet joints in the section of the spinal column can be different, with the degrees of the joint action of the facet joints increasing as the degree of flexion or extension of the section of the spinal column increases, and vice versa.

Wearable joint-action sensor 100 is worn by the user on top of a first section of the upper spinal column (the first section of the upper spinal column is the first body segment in this embodiment) and adjacent to a second section of the upper spinal column (the second section of the upper spinal column is the second body segment in this embodiment), and both the first and second sections of the upper spinal column (i.e. the region comprising both the first and second body segments) serve as user's body target 114 for sensing plate 118 of capacitive proximity sensor 102 (in FIG. 1) in wearable joint-action sensor 100. Although user's body target 114 is covered with shirt 1800, sensing plate 118 can still be used for detecting the amount of separation 130 (in FIG. 1) and the rate of change between sensing plate 118 and user's body target 114, because typical clothing materials do not alter the electric field between sensing plate 118 and user's body target 114 severely.

Wearable joint-action sensor 100 inside housing 1801 and reminder 1700 can be attached to shirt 1800 by using a mounting clip or pin, or it can be attached to shirt 1800 by any other mechanism, such as by sewing, or by using any type of magnetic, adhesive, or adhering device. Furthermore, wearable joint-action sensor 100 can also be attached directly, such as by adhesive or adhesive tape, to the upper spinal column of a user without using shirt 1800. In FIG. 18, although there is separation 130 between sensing plate 118 and user's body target 114 when the user's posture is balanced and upright, sensing plate 118 can touch (or almost touch) user's body target 114 to detect a balanced and upright posture.

Although only one sensing plate 118 is illustrated in FIG. 18, multiple sensing plates can be incorporated in wearable joint-action sensor 100 to obtain more separation data for the upper spinal column as the user flexes or extends the upper spinal column. Wearable joint-action sensor 100 with multiple sensing plates can also facilitate obtaining appropriate separation data for the upper spinal column even when a user does not wear wearable joint-action sensor 100 exactly as directed, because in this case some of the sensing plates could still be located at an appropriate proximity of the upper spinal column for detecting joint actions of the upper spinal column.

Joint-Action Detection Operation

FIG. 19

Figure 19:
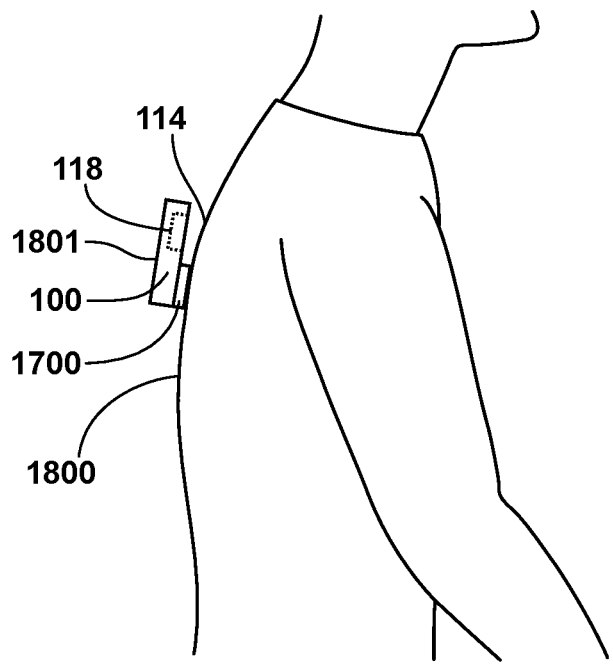
FIG. 19 is a graphical illustration of an increase in the amount of separation between the capacitive proximity sensor and the upper spinal column of the user in FIG. 18 as the user flexes the upper spinal column.

FIG. 19 illustrates an increase in the amount of separation 130 (in FIG. 1) between sensing plate 118 of capacitive proximity sensor 102 (in FIG. 1) and user's body target 114 (i.e. between capacitive proximity sensor 102 and user's body target 114) as the user flexes the upper spinal column. The increase in the amount of separation 130 results in a decrease in capacitance of sensing pad 108 (in FIG. 1) on sensing plate 118 to ground, which is detected by capacitive proximity sensor 102. When the amount of separation 130 exceeds a predetermined threshold, wearable joint-action sensor 100 uses its communication device 138 (in FIG. 1) and signal link 1702 (in FIG. 17) to communicate with reminder 1700, which can speak, vibrate, beep, display, or generate any noticeable signal for reminding the user that a poor posture is or has been detected, so that the user can maintain a good upright posture of the upper spinal column. On the other hand, although not illustrated in a figure here, the amount of separation 130 between sensing plate 118 and user's body target 114 decreases as the user extends the upper spinal column, and such a decrease in separation 130 can also be detected by capacitive proximity sensor 102 for reminding the user (by using signal link 1702 and reminder 1700), so that the user can maintain an appropriate amount of extension of the upper spinal column, such as when the user is doing certain exercise. Reminder 1700 can produce different levels of intensity of vibration, sound, voice, light, or produce different verbal or visual messages (for encouragement or discouragement to the user), corresponding to the degree of flexion or extension of the upper spinal column of the user.

When the user's spinal column is involved in a physical activity, such as sitting, standing, walking, running, or dancing, one or more sensing plates can be incorporated in wearable joint-action sensor 100 worn on top of the spinal column to detect actions of the spinal column, and to remind the user with reminder 1700 that a desired or undesired action of the spinal column is or has been detected, so long as capacitive proximity sensor 102 of wearable joint-action sensor 100 can detect the amount of separation 130 and the rate of change between sensing plate 118 and user's body target 114 on the sections of the spinal column that are involved in the physical activity.

Although FIG. 19 illustrates that wearable joint-action sensor 100 inside housing 1801 and reminder 1700 are worn on the upper spinal column of a user to remind the user that a poor posture involving the upper spinal column is or has been detected, wearable joint-action sensor 100 inside housing 1801 and reminder 1700 can be worn anywhere along the spinal column to remind the user that a desired or undesired action of certain sections of the spinal column is detected by using the same detection principle, so long as all the facet joints in the sections of the spinal column have the same joint action during flexion or extension of the sections of spinal column. Furthermore, reminder 1700 can be located far away from wearable joint-action sensor 100 to remind someone else (such as a caregiver of the user) that a poor posture is or has been detected. Reminder 1700 can also be implemented in a computing device, such as a smartwatch, fitness wristband, smartphone, or computer, and use the display, speaker, light-emitting diode (LED), or vibrator of the computing device to remind a user or a caregiver of the user that a desired or undesired action of certain sections of the spinal column is or has been detected.

Reminder 1700 can be used in any embodiment to remind a user, or someone else, such as a caregiver of the user, that a predetermined joint action is or has been detected. For example, reminder 1700, which can include a timer and be incorporated in housing 301 (in FIGS. 3A and 3B) of wearable joint-action sensor 100 in the first embodiment, can remind a user that the user has been sitting for too long. Furthermore, in any embodiment, reminder 1700 can include a timer and be incorporated in wearable joint-action sensor 100 to remind a user or someone else, such as a caregiver of the user (for example, the mother of a child), that a predetermined joint action is detected or not detected for a predetermined period of time.

Figure 22:
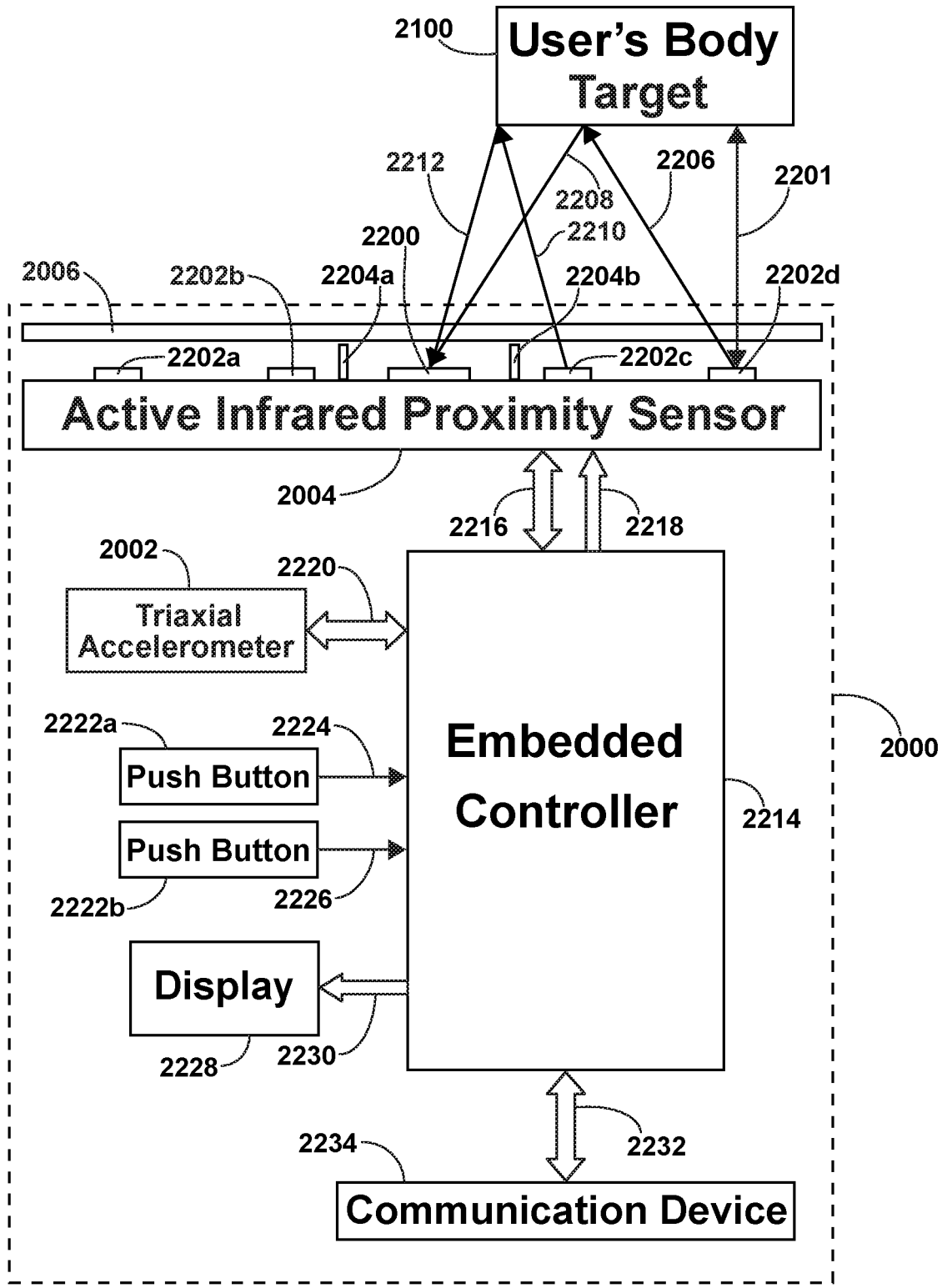
FIG. 22 is a block diagram showing schematically the wearable joint-action sensor incorporating the active infrared proximity sensor and the triaxial accelerometer in accordance with the eighth embodiment.

FIGS. 20A, 20B, and 22

Eighth Embodiment

An eighth embodiment of the wearable joint-action sensor is illustrated in FIGS. 20A, 20B, and 22. FIG. 20A is a side view of a wearable joint-action sensor 2000 inside a housing 2001 worn on the right waist of the torso (the torso is the first body segment in this embodiment) of a user (a human being in this embodiment) above the right thigh of the right upper leg (the right upper leg is the second body segment in this embodiment) with a waist belt 2008 to detect joint actions, such as flexion, extension, abduction, and adduction, of the right hip joint, which links the right thigh to the torso. Wearable joint-action sensor 2000 inside housing 2001 incorporates an active infrared proximity sensor 2004, which is illustrated by a dotted outline. An overlay 2006, which is usually made of glass or plastic, is in front of active infrared proximity sensor 2004 and allows infrared light to pass through. In this embodiment, a user's body target 2100 for active infrared proximity sensor 2004 is the right thigh of the right upper leg (the second body segment), which is illustrated in FIGS. 21A and 21B.

An active infrared proximity sensor comprises an infrared proximity sensor and an infrared-light source (the active element for infrared proximity sensing), such as an infrared light-emitting diode (LED). The reflected infrared-light intensity from a target in the proximity of the active infrared proximity sensor is sensed by the infrared proximity sensor to detect the separation between the active infrared proximity sensor and the target. A time-of-flight proximity sensor is also an active infrared proximity sensor (it is an advanced active infrared proximity sensor), but it uses an infrared laser diode instead of an infrared light-emitting diode (LED) as the infrared-light source. It measures the time light takes to travel from the time-of-flight proximity sensor to the target and reflect back to the time-of-flight proximity sensor to detect the separation, which is the range measured by the time-of-flight proximity sensor. The range obtained from a time-of-flight proximity sensor can be in a standard measurement unit, such as millimeter, or it can be in any unit (such as picosecond of time of flight or the count of a time counter) that is proportional to a standard measurement unit. The advantage of a time-of-flight proximity sensor is that the detected separation (i.e. the range based on the time of flight of light) does not depend on the infrared-light reflectance of the target as the detected separation of active infrared proximity sensor 2004 does. For this reason, a time-of-flight proximity sensor can replace active infrared proximity sensor 2004 in wearable joint-action sensor 2000 for achieving an improved performance, in cases where the likely higher cost and power consumption of a time-of-flight proximity sensor are acceptable.

In FIG. 20A, the user is standing, and the right thigh is not in the vertically downward line of sight of active infrared proximity sensor 2004, so no user's body target for active infrared proximity sensor 2004 is illustrated. In this case, the target of active infrared proximity sensor 2004 is the floor or ground (not shown in FIG. 20A) on which the user is standing. Although the floor or ground is not a user's body target per se, because it is not a part of the user's body, it can still be a useful target for detecting actions of the right hip joint when it is in the proximity of the right hip joint. For example, wearable joint-action sensor 2000 can detect abduction of the right hip joint as the user opens out the right leg to the right side, with both the right and left foot remaining on the floor or ground, bringing active infrared proximity sensor 2004 on the right waist closer to the floor or ground. When the floor or ground falls into the sensing range of active infrared proximity sensor 2004, the detected separation between active infrared proximity sensor 2004 and the floor or ground decreases as the degree of abduction increases.

Wearable joint-action sensor 2000 inside housing 2001 also incorporates a triaxial (three-axis) accelerometer 2002, which is illustrated by a dotted outline, to sense acceleration in three orthogonal axes X, Y, and Z for detecting the user's body actions. In this case, the torso is the body segment sensed by triaxial accelerometer 2002, and a body action comprises movement and orientation of the body segment. To simplify discussion of the orientation of triaxial accelerometer 2002 with respect to the vertically downward direction of the earth's gravitational acceleration G, the directions of the X, Y, and Z axes are chosen such that the static earth's gravitational acceleration sensed along each axis is set to G when the axis points vertically downward, even if the acceleration data obtained from triaxial accelerometer 2002 for the axis is −G in this orientation. Only the Y and Z axes of triaxial accelerometer 2002 are illustrated in FIG. 20A, because the X axis points out of the figure.

The eighth embodiment combines the detected joint actions and body actions of a user to detect the types of physical activity performed by the user. Although triaxial accelerometer 2002 is used in the eighth embodiment for detecting body actions of the user, a one-axis (also called single-axis or uniaxial) or a two-axis (also called dual-axis or biaxial) accelerometer, or a combination of the same or different types of accelerometers, can also be used instead, depending on the types of body actions of a body segment needed to be detected for determining the types of physical activity performed by a user. Furthermore, if necessary, a gyroscope can be used to detect rotation of the body segment, which is a type of movement of the body segment.

FIG. 20B is a front view (the surface that faces the right abdomen of the user) of wearable joint-action sensor 2000 inside housing 2001 in FIG. 20A. Active infrared proximity sensor 2004 (illustrated by a dotted outline) and overlay 2006 are placed along the lower portion of housing 2001 to facilitate detection of abduction (opening out to the side of the user's body) and adduction (opposite to abduction) of the right hip joint, so long as the right hip joint is at least slightly flexed such that the right thigh is in the line of sight of active infrared proximity sensor 2004. Otherwise the floor or ground could become the target as discussed above. FIG. 20B also shows triaxial accelerometer 2002 (also illustrated by a dotted outline) inside housing 2001, and only the X and Z axes of triaxial accelerometer 2002 are illustrated, because the Y axis points into the figure.

Wearable joint-action sensor 2000 inside housing 2001 can be attached to waist belt 2008 by using a mounting clip, which is commonly used for wearing a mobile phone or pager on the waist of a user. Wearable joint-action sensor 2000 inside housing 2001 can be attached to waist belt 2008 by any other mechanism, such as by sewing, or by using any type of magnetic, adhesive, or adhering device. Wearable joint-action sensor 2000 inside housing 2001 can also be attached directly, such as by adhesive or adhesive tape, to the waist of a user without using waist belt 2008, or be clipped to a pants pocket that is close to the waist. Furthermore, wearable joint-action sensor 2000 can be incorporated inside the housing of a smartphone, which is worn on the waist of a user, so that housing 2001 is not needed. As illustrated in FIG. 20A, the right thigh is not in the vertically downward line of sight of active infrared proximity sensor 2004 when the user is standing.

We presently contemplate using an infrared proximity sensor that is available from Maxim Integrated Products Inc. of California (Product Number: MAX44000) as the infrared proximity sensor in active infrared proximity sensor 2004, although an infrared proximity sensor manufactured by another company, or another type of proximity sensor, such as an ultrasonic proximity sensor or a single-chip radar, can also be used. One or more infrared LEDs in active infrared proximity sensor 2004 serve as the infrared-light sources for active infrared proximity sensing. As discussed above, a time-of-flight proximity sensor, which is an advanced active infrared proximity sensor, instead of active infrared proximity sensor 2004, can also be used in the eighth embodiment. A time-of-flight proximity sensor module, which includes an infrared laser diode, is available from STMicroelectronics of Switzerland (Product Number: VL6180X). We presently contemplate using a triaxial accelerometer that is available from M-CUBE Inc. of California (Product Number: MC3610) as triaxial accelerometer 2002, although an accelerometer manufactured by another company can also be used.

FIG. 22 shows a block diagram of wearable joint-action sensor 2000 incorporating active infrared proximity sensor 2004 and triaxial accelerometer 2002. FIG. 22 also shows a side view of active infrared proximity sensor 2004 illustrating its infrared proximity sensor 2200, and infrared LEDs 2202a, 2202b, 2202c, and 2202d, which serve as the infrared-light sources. As illustrated in FIG. 22, when an infrared-light beam 2206 emitted from infrared LED 2202d is reflected by user's body target 2100, which is the user's right thigh in this embodiment, a reflected infrared-light beam 2208 reaches infrared proximity sensor 2200. Using a small rectangular user's body target 2100 to illustrate the user's right thigh and treating the surface of user's body target 2100 as a specular reflector instead of a diffuse reflector simplifies discussion of the operation of active infrared proximity sensor 2004. Furthermore, user's body target 2100 can be covered with clothing that has certain reflection and transmission characteristics for infrared light. The effect of variations in infrared-light reflection characteristic of user's body target 2100 (with or without clothing) can be reduced by performing a calibration process after wearable joint-action sensor 2000 is worn on the waist of a user. When a user walks or runs, active infrared proximity sensor 2004 can use the waveform of the reflected infrared-light-intensity to determine a reflected infrared-light-intensity threshold for detecting significant flexion of a user's right hip joint, where significant flexion is any degree of flexion that is larger than the minimum degree of flexion required for the user to take an ambulating step forward with the right leg by flexing the right hip joint, as discussed below.

When an infrared-light beam 2210 emitted from infrared LED 2202c is reflected by the edge of user's body target 2100, a less intense reflected infrared-light beam 2212 reaches infrared proximity sensor 2200, because the reflecting surface is substantially reduced near the edge. On the left side of active infrared proximity sensor 2004, any infrared-light beam emitted from infrared LED 2202a or 2202b cannot produce a reflected infrared-light beam from user's body target 2100 that can reach infrared proximity sensor 2200, unless user's body target 2100 moves to the left side of active infrared proximity sensor 2004.

In FIG. 22, a separation 2201 between active infrared proximity sensor 2004 and user's body target 2100 is not to scale. Optional optical components, such as lens and reflectors, can be used for infrared LEDs 2202a, 2202b, 2202c, and 2202d, as well as for infrared proximity sensor 2200, to change the directions and shapes of the emitted infrared-light beams from the infrared LEDs and the reflected infrared-light beams to infrared proximity sensor 2200. The direction of the emitted infrared-light beam from an infrared LED can also be changed by tilting the infrared LED toward the desired direction of the infrared-light beam when mounting the infrared LED on active infrared proximity sensor 2004.

Under the control of an embedded controller 2214 through buses 2216 and 2218, active infrared proximity sensor 2004 sequentially emits an infrared-light beam from one of infrared LEDs 2202a, 2202b, 2202c, and 2202d (the particular infrared LED is selected by embedded controller 2214 using bus 2218), and the resulting reflected infrared-light intensity for each infrared LED is sensed by infrared proximity sensor 2200. Bus 2216 is a standard communication bus, such as an inter-integrated circuit bus or a serial peripheral interface bus, while bus 2218 is a custom bus whose purpose is to select one of the four infrared LEDs at a time to be driven by active infrared proximity sensor 2004. The reflected infrared-light intensity for each of the four infrared LEDs is sent to embedded controller 2214 sequentially through bus 2216, and the reflected infrared-light intensities for all four infrared LEDs are used together to detect the amount of separation 2201 (i.e. the height of an isosceles triangle formed by infrared-light beams 2210 and 2212, and the distance between infrared proximity sensor 2200 and infrared LED 2202c) between active infrared proximity sensor 2004 and user's body target 2100. This detection process also detects the deviation of user's body target 2100 from the midline of active infrared proximity sensor 2004 at infrared proximity sensor 2200. For example, user's body target 2100 in FIG. 22 is deviated to the right side of the midline (i.e. the right side of infrared proximity sensor 2200) of active infrared proximity sensor 2004. Embedded controller 2214 also uses bus 2216 to configure active infrared proximity sensor 2004 for appropriate proximity sensing, such as to set the drive current for the infrared LEDs and the sampling rate for the reflected infrared-light intensities. The amount of separation 2201 between active infrared proximity sensor 2004 and user's body target 2100, as well as the amount of deviation of user's body target 2100 from the midline of active infrared proximity sensor 2004, is used for detecting actions of the right hip joint (the right hip joint is not shown in FIG. 22), such as flexion, abduction, and adduction.

Infrared light can pass through overlay 2006 of active infrared proximity sensor 2004, which can be transparent or be coated with a film that absorbs visible light. Active infrared proximity sensor 2004 drives each of infrared LEDs 2202a, 2202b, 2202c, and 2202d sequentially with very short pulses to reduce power consumption and to facilitate cancellation of ambient infrared radiation. Infrared proximity sensor 2200 of active infrared proximity sensor 2004 typically has a mechanism for cancelling (such as by subtraction) the ambient infrared-light intensity, which is the baseline infrared-light intensity sensed by infrared proximity sensor 2200 before the reflected infrared-light beam of an infrared LED is sensed. This cancellation mechanism allows active infrared proximity sensor 2004 to operate under a large amount of ambient infrared radiation, such as under the sun. When there is a large 100 or 120-Hertz fluctuation of ambient infrared-light intensity, such as when incandescent light bulbs are powered by the mains electricity, the effect of this fluctuation of ambient infrared-light intensity can be reduced by obtaining data from active infrared proximity sensor 2004 at a 100 or 120-Hertz sampling rate, depending on the frequency of the mains electricity. Light barriers 2204a and 2204b, one on each side of infrared proximity sensor 2200, form a complete optical block. Light barriers 2204a and 2204b can be made of any material, such as natural rubber or copper, that does not allow infrared light to pass through, so that an infrared-light beam emitted from any infrared LED 2202a, 2202b, 2202c, or 2202d is not able to reach infrared proximity sensor 2200 by reflection under overlay 2006. The need for light barriers 2204a and 2204b can be reduced by placing infrared proximity sensor 2200 and infrared LEDs 2202a, 2202b, 2202c, and 2202d as close to overlay 2006 as possible.

When wearable joint-action sensor 2000 inside housing 2001 is mounted on waist belt 2008 (in FIGS. 20A, 21A, and 21B), it is important to keep a minimum separation between active infrared proximity sensor 2004 and user's body target 2100, so that at least one of infrared LEDs 2202a, 2202b, 2202c, and 2202d can produce a strong reflected infrared-light beam that reaches infrared proximity sensor 2200 when user's body target 2100 is at the minimum separation. Such minimum separation can be guaranteed by various designs, such as by designing housing 2001 to be mounted high enough on waist belt 2008, or by placing overlay 2006 (or active infrared proximity sensor 2004 without overlay 2006) in a recess at the bottom of housing 2001. Another possible design is to place overlay 2006 away from light barriers 2204a and 2204b, forming a partial optical block (i.e. a certain acceptable amount of infrared-light reflection under overlay 2006 can reach infrared proximity sensor 2200) instead of the complete optical block illustrated in FIG. 22, so that at least one of infrared LEDs 2202a, 2202b, 2202c, and 2202d can produce a strong reflected infrared light beam (from user's body target 2100) that reaches infrared proximity sensor 2200 when user's body target 2100 presses on overlay 2006.

The reflected infrared-light intensity obtained from infrared proximity sensor 2200 is typically a binary number that is proportional to a standard measurement of the reflected infrared-light intensity in watts per square meter, and converting the reflected infrared-light-intensity binary number to a standard measurement of reflected infrared-light intensity is usually unnecessary. The reflected infrared-light intensity obtained from infrared proximity sensor 2200 can be used directly in embedded controller 2214 after a calibration process that relates the reflected infrared-light-intensity to the amount of separation 2201 between active infrared proximity sensor 2004 and user's body target 2100, as well as the amount of deviation of user's body target 2100 from the midline of active infrared proximity sensor 2004. This calibration process can be performed during the manufacturing of wearable joint-action sensor 2000 with objects similar in shape and size to human thighs, it can be performed by instructing a user to perform certain actions of the right hip joint while wearing wearable joint-action sensor 2000 on the right waist of the user, or it can be performed while a user is walking or running, producing a periodic reflected infrared-light-intensity waveform that can be analyzed with various techniques, as discussed below.

Although four infrared LEDs of active infrared proximity sensor 2004 are illustrated in FIG. 22, more or fewer infrared LEDs can be used in active infrared proximity sensor 2004. In fact, only one infrared LED is needed for detecting separation 2201 between active infrared proximity sensor 2004 and user's body target 2100, if user's body target 2100 does not significantly deviate from the midline of active infrared proximity sensor 2004 (i.e. the right hip joint is not significantly abducted or adducted). However, at least two infrared LEDs, with one infrared LED on each side of infrared proximity sensor 2200, are required for sensing the amount of deviation of user's body target 2100 from the midline of active infrared proximity sensor 2004 based on the relative intensities of the reflected infrared-light beams obtained from the two infrared LEDs. Instead of arranging the infrared LEDs in a one-dimensional array, as illustrated in FIG. 22, the infrared LEDs can be arranged in a two-dimensional array, or in any spatial pattern to facilitate determination of the amount of separation 2201 between active infrared proximity sensor 2004 and user's body target 2100, as well as the amount of deviation of user's body target 2100 from the midline of active infrared proximity sensor 2004. Furthermore, active infrared proximity sensor 2004, including its infrared LEDs, can be mounted on a flexible printed circuit or other surface, so that it can be incorporated inside waist belt 2008, or along the surface of waist belt 2008. In fact, the entire wearable joint-action sensor 2000, including active infrared proximity sensor 2004 and its infrared LEDs, can be incorporated inside waist belt 2008 or along the surface of waist belt 2008 by using similar mounting techniques.

Embedded controller 2214 uses a bus 2220, such as an inter-integrated circuit bus or a serial peripheral interface bus, to configure triaxial accelerometer 2002, such as to set the sensitivity and sampling rate, and to receive data from triaxial accelerometer 2002 with regard to accelerations along its X, Y, and Z axes. For a user interface, embedded controller 2214 reads signals 2224 and 2226 from push buttons 2222a and 2222b, respectively, and uses an output bus 2230 to drive an optional display 2228, such as an LCD module. Embedded controller 2214 also uses a bus 2232, such as an inter-integrated circuit bus or a serial peripheral interface bus, to communicate with an optional communication device 2234. Communication device 2234, such as a USB (Universal Serial Bus), Bluetooth®, Wi-Fi®, or NFC (near-field communication) device, or any radio-frequency, optical, acoustic, or wired communication device, provides wired or wireless communication for embedded controller 2214 to communicate with a computing device (not shown in FIG. 22), such as a smartwatch, fitness wristband, smartphone, or computer. Embedded controller 2214 can use the display of the computing device for displaying any data or detection result, so that display 2228 is not needed. Communication device 2234 can also connect wearable joint-action sensor 2000 to the internet to make wearable joint-action sensor 2000 a part of the Internet of Things (IoT).

Embedded controller 2214 processes the reflected infrared-light-intensity data obtained from active infrared proximity sensor 2004 and the acceleration data obtained from triaxial accelerometer 2002 to detect a joint action with a software or hardware joint-action detector and a body action with a software or hardware body-action detector. Embedded controller 2214 also combines the detected joint-action and body-action to detect the type of physical activity performed by a user with a software or hardware physical-activity detector. Alternatively, by using communication device 2234, embedded controller 2214 can send the reflected infrared-light-intensity data and the acceleration data to a computing device (not shown in FIG. 22), such as a smartwatch, fitness wristband, smartphone, or computer, or to any device that is connected to the internet (such as the cloud) for detecting joint actions, body actions, and physical activities with the corresponding software or hardware detectors, and for displaying the data or detection result (so that display 2228 is not needed in wearable joint-action sensor 2000). The computing device or any device that is connected to the internet can also send configuration data and instructions to embedded controller 2214 to control its operation, so that push buttons 2222a and 2222b are not needed.

Joint-Action and Physical-Activity Detection Operations

Figure 23:
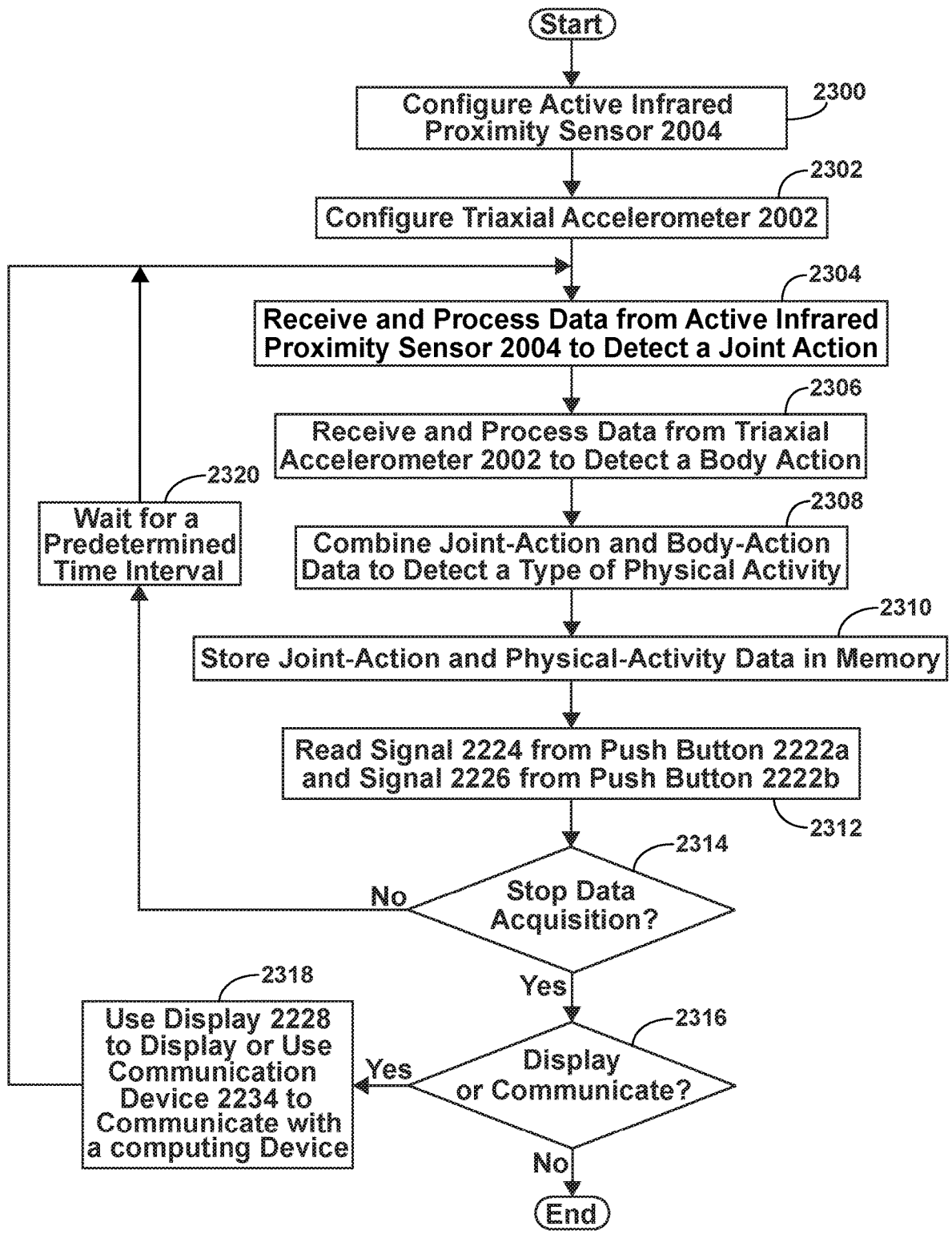
FIG. 23 is a flow diagram illustrating the operation of the wearable joint-action sensor in FIG. 22 in accordance with the eighth embodiment.

FIGS. 21A, 21B, and 23

In FIG. 21A, wearable joint-action sensor 2000 incorporating active infrared proximity sensor 2004 inside housing 2001 is worn on the right waist of the user above the right thigh with waist belt 2008. FIG. 21A shows separation 2201 (in FIG. 22) between active infrared proximity sensor 2004 (illustrated by a dotted outline) and user's body target 2100 (the right thigh of the user) when the user flexes the right hip joint, such as when the user is sitting. User's body target 2100 reflects the infrared-light beam emitted (through overlay 2006) from an infrared LED of active infrared proximity sensor 2004, and the reflected infrared-light intensity is sensed (also through overlay 2006) by infrared proximity sensor 2200 to detect separation 2201 between active infrared proximity sensor 2004 and user's body target 2100 for detecting actions of the right hip joint. Wearable joint-action sensor 2000 also incorporates triaxial accelerometer 2002, which is also illustrated by a dotted outline, for detecting body actions of the torso of the user. Only the Y and Z axes of triaxial accelerometer 2002 are illustrated in FIG. 21A, because the X axis points out of the figure.

FIG. 21B illustrates an increase in the amount of separation 2201 between active infrared proximity sensor 2004 and user's body target 2100 when the user decreases the degree of flexion of the right hip joint, such as when the user gets up from the sitting position illustrated in FIG. 21A. The increase in the amount of separation 2201 results in a decrease in the reflected infrared-light intensity sensed (through overlay 2006) by infrared proximity sensor 2200 of active infrared proximity sensor 2004, so wearable joint-action sensor 2000 inside housing 2001 can detect a decrease in the degree of flexion of the right hip joint. Wearable joint-action sensor 2000 can also detect the upright posture of the torso of the user from the acceleration data received from triaxial accelerometer 2002, because the acceleration sensed along its Z axis is about −G, where G is the earth's gravitational acceleration that is pointing vertically downward (not shown in FIG. 21B). The accelerations sensed along the X and Y axis are about zero (the X axis is not illustrated in FIG. 21B because it is pointing out of the figure), because the X and Y axis are almost orthogonal to the direction of the earth's gravitational acceleration G. Wearable joint-action sensor 2000 combines the detected joint action (a decrease in the degree of flexion of the right hip joint) and the detected body action (the torso maintains an approximately upright posture) to detect that the physical activity performed by the user is the action of getting up from a sitting position. On the other hand, if the detected joint action is still a decrease in the degree of flexion of the right hip joint, but the acceleration sensed along the Y axis is about G, and the accelerations sensed along the X and Z axis are about zero, then wearable joint-action sensor 2000 detects that the physical activity performed by the user is the action of crawling on the floor instead, because the detected body action of the torso is that the torso is about orthogonal to the earth's gravitational acceleration G, with the abdomen of the torso facing the floor or ground.

Triaxial accelerometer 2002 is inside housing 2001, which is attached to the waist of a user with waist belt 2008. Techniques of using acceleration data from a waist-worn triaxial accelerometer for counting steps have been developed for prior-art waist-worn pedometers, and these techniques can be combined with those for detecting actions of the right hip joint in wearable joint-action sensor 2000 to improve accuracy in detection of steps when the user walks or runs, and to detect other types of physical activity performed by the user. As discussed above, the orientation of the torso with respect to the direction of the earth's gravitational acceleration G is detected by triaxial accelerometer 2002, and the orientation of the torso is important for detecting the type of physical activity performed by the user.

The orientation of the torso (i.e. the body action of the torso) sensed by triaxial accelerometer 2002 is also important for detecting extension, abduction, or adduction of the right hip joint of the user indirectly. When the right hip joint is extended, the right thigh is not in the line of sight of active infrared proximity sensor 2004, so the reflected infrared-light intensity is very low (the floor or ground, which is significantly farther away, could be out of the sensing range of active infrared proximity sensor 2004), but a forward inclination of the torso of the user (a body action for balancing) can be detected by triaxial accelerometer 2002 and be used by wearable joint-action sensor 2000 for detecting extension of the right hip joint indirectly. Similarly, by detecting a sideways inclination of the torso of the user (a body action for balancing) in combination with a very low reflected infrared-light intensity sensed by infrared proximity sensor 2200 of active infrared proximity sensor 2004 when the right hip joint is not flexed significantly, wearable joint-action sensor 2000 can detect abduction or adduction of the right hip joint indirectly. When the user is standing, the right thigh is not in the vertically downward line of sight of active infrared proximity sensor 2004 (in FIG. 20A), so the reflected infrared-light intensity is very low, but the acceleration along the Z axis of triaxial accelerometer 2002 is about −G, so wearable joint-action sensor 2000 detects standing by combining the joint-action data (which shows that the right hip joint is not flexed) obtained from active infrared proximity sensor 2004 and the body-action data obtained from triaxial accelerometer 2002.

When the user walks or runs, the right hip joint flexes as the user takes a step forward with the right leg, and the right hip joint extends as the user takes a step forward with the left leg. Wearable joint-action sensor 2000 can be used as a physical-activity monitor by using active infrared proximity sensor 2004 to sense the periodic variation of the reflected infrared-light intensity, which represents the periodic variation of separation 2201, and measuring the rate of change of the reflected infrared-light intensity when the user walks or runs. The number of steps that the user takes can be detected by analyzing the waveform of the reflected infrared-light intensity with various techniques, such as by detecting the total number of peaks of the waveform, which corresponds to the total number of maximum flexions of the right hip joint. Multiplying the number of maximum flexions or the number significant flexions of the right hip joint by a factor of two can produce the number of steps that the user takes, where significant flexion is any degree of flexion that is larger than the minimum degree of flexion of the right hip joint required for the user to take an ambulating step forward with the right leg. A significant flexion can be detected from the waveform of the reflected infrared-light intensity by using an infrared-light intensity threshold (i.e. a threshold for the degree of flexion), which can be determined based on the amplitude of the waveform, such as using a threshold at a predetermined percentage of the amplitude of the waveform above or below the midline of the waveform, depending on the specific design of wearable joint-action sensor 2000. Unlike a pedometer that use just an accelerometer to detect steps, wearable joint-action sensor 2000, which also detects actions of the right hip joint, does not mistakenly count steps when a user's body vibrates on a traveling vehicle, because the right hip joint does not flex and extend alternately in this case.

The repeated flexions of the right hip joint when the user walks or runs can be detected by using just one infrared LED in active infrared proximity sensor 2004 for detecting separation 2201 between active infrared proximity sensor 2004 and the right thigh. In this case, if processing data obtained from triaxial accelerometer 2002 with prior-art techniques for step counting indicates that the user has taken a number of steps, but processing data obtained from active infrared proximity sensor 2004 indicates that the user has taken a significantly fewer number of steps, this indicates that the user has not been walking or running in a typical manner. For simplicity, this type of atypical walking or running activity is called dancing activity in this description.

Wearable joint-action sensor 2000 detects dancing activity when a user actually dances or when the user just taking small irregular steps when doing chores, without ambulating (i.e. without walking or running) from one place to another place a distance away. When the user actually dances, the right hip joint flexes and extends with the right thigh deviate frequently away from the line of sight of active infrared proximity sensor 2004 with just one infrared LED, so wearable joint-action sensor 2000 might not be able to detect some of the dancing steps from the reflected infrared-light-intensity data obtained from active infrared proximity sensor 2004. On the other hand, based on the acceleration data obtained from triaxial accelerometer 2002, wearable joint-action sensor 2000 likely detects more steps than the user actually takes for dancing, because the user tends to wiggle the waist while dancing, resulting in counting steps when the user just wiggles triaxial accelerometer 2002 in housing 2001 worn on the waist without actually taking an ambulating step. Similarly, when the user takes small steps irregularly when doing chores, such as when the user is sweeping the floor, the degrees of flexion of the right hip joint could be too small (i.e. the right hip joint is not significantly flexed) that wearable joint-action sensor 2000 might not count some of these small steps as ambulating steps based on the reflected infrared-light-intensity data obtained from active infrared proximity sensor 2004. On the other hand, wearable joint-action sensor 2000 likely counts these small steps as ambulating steps based on the data obtained from triaxial accelerometer 2002, because the waist of the torso of the user still vibrates when the user takes small steps.

Wearable joint-action sensor 2000 can differentiate between actual dancing and taking small irregular steps by using one or more infrared LEDs on each side of infrared proximity sensor 2200 (in FIG. 22, there are two infrared LEDs on each side of infrared proximity sensor 2200) of active infrared proximity sensor 2004 to detect frequent deviations of the right thigh to the left and right sides of the midline of active infrared proximity sensor 2004 when a user actually dances. When a user takes small steps, the right thigh does not deviate to the left and right sides of the midline of active infrared proximity sensor 2004 as frequently as when the user dances. Dancing activity, which includes actual dancing and taking small irregular steps in this description, consumes a different number of calories in a period of time when compared to walking or running, so it should be treated as a different type of physical activity for estimating energy expenditure. While prior-art pedometers often mistakenly treat dancing activity as ambulation, wearable joint-action sensor 2000 in the eighth embodiment can detect dancing activity.

Another advantage of using wearable joint-action sensor 2000 as a physical-activity monitor is that it can also detect whether a user is sitting or standing when the user is not walking or running. As illustrated in the block diagram for the seventh embodiment (in FIG. 17), wearable joint-action sensor 2000 in the eighth embodiment can also communicate with reminder 1700 that includes a timer to be used as a sitting detector for reminding a user (such as by vibration, sound, voice, light, or a message on a display) that the user has been sitting for too long. The timer function can also be implemented by a hardware or software timer in embedded controller 2214, without requiring that reminder 1700 includes a timer.

Wearable joint-action sensor 2000 can detect sitting or standing accurately after the reflected infrared-light intensity sensed by infrared proximity sensor 2200 of active infrared proximity sensor 2004 is calibrated for the degree of flexion of the right hip joint when a user is sitting or standing, respectively. With less elaborate calibration, wearable joint-action sensor 2000 can still detect sitting and standing quite accurately by sensing the duration of significant flexion and no significant flexion of a user's right hip joint, respectively, where significant flexion is any degree of flexion that is larger than the minimum degree of flexion required for the user to take an ambulating step forward with the right leg by flexing the right hip joint. This is based on the fact that the right hip joint is in significant flexion for a long duration when the user is sitting, and the right hip joint is not in significant flexion for a long duration when the user is standing. The duration of significant flexion or no significant flexion, or the duration of any detected joint action, can be determined by a hardware or software timer implemented in embedded controller 2214. When the duration of a detected significant flexion of the right hip joint exceeds a predetermined duration, sitting is detected. On the other hand, when the duration of a detected no significant flexion of the right hip joint exceeds a predetermined duration, standing is detected. When a user is doing squats for exercise instead of either sitting or standing, the right hip joint is in significant flexion and no significant flexion alternately, which can be detected by wearable joint-action sensor 2000, so long as the duration of significant flexion or no significant flexion (or both) is longer than a predetermined duration for walking or running, indicating that the user is not walking or running.

As discussed above, wearable joint-action sensor 2000 can also use its communication device 2234 and signal link 1702 to communicate with reminder 1700 (in FIG. 17) for reminding a user. Reminder 1700 can be incorporated inside housing 2001 and use simple electrical connections for communicating with wearable joint-action sensor 2000, or it can be far away from the user for reminding someone else, such as a caregiver of the user. Communication device 2234 can be a USB (Universal Serial Bus), Bluetooth®, Wi-Fi®, or NFC (near-field communication) device, or any radio-frequency, optical, acoustic, or wired communication device that provides wired or wireless communication. Wearable joint-action sensor 2000 can use communication device 2234 to communicate with a computing device, such as a smartwatch, fitness wristband, smartphone, or computer, to control the computing device (as illustrated in FIG. 9) to deliver the reminding or notifying messages with its display or speaker, instead of using reminder 1700 to deliver the reminding or notifying messages. Wearable joint-action sensor 2000 can also detect how much time (with a hardware or software timer implemented in embedded controller 2214) a user spends in each of sitting, standing, dancing, and ambulating (i.e. either walking or running, with or without counting steps). The time distribution among these types of physical activity performed by the user could be more relevant for improving the user's health than the number of steps counted with a prior-art pedometer, which cannot reliably distinguish between sitting, standing, and dancing.

Wearable joint-action sensor 2000 can be used for detecting any type of physical activity that involves the right hip joint, without the inconvenience of attaching a sensor to the right thigh of a user, as suggested by the prior arts for sensing actions of the right hip joint. Although FIGS. 20A, 21A, and 21B illustrate that wearable joint-action sensor 2000 is worn on the right waist of a user above the right thigh using waist belt 2008 for detecting actions of the right hip joint, wearable joint-action sensor 2000 can be worn on the left waist of a user using waist belt 2008 for detecting actions of the left hip joint by using the same detection principle.

FIG. 23 is a flow diagram illustrating the joint-action and body-action detection operations of wearable joint-action sensor 2000 in FIG. 22. In FIG. 23, after wearable joint-action sensor 2000 has been turned on, embedded controller 2214 sends configuration data through bus 2216 to set up active infrared proximity sensor 2004 at step 2300, and sends configuration data through bus 2220 to set up triaxial accelerometer 2002 at step 2302 for detecting a joint action of the right hip joint and a body action of the torso, respectively.

At step 2304, embedded controller 2214 sequentially selects one of infrared LEDs 2202a, 2202b, 2202c, and 2202d as the infrared-light source, and then uses bus 2216 to receive the corresponding reflected infrared-light-intensity data from active infrared proximity sensor 2004. Embedded controller 2214 processes the reflected infrared-light-intensity data for infrared LEDs 2202a, 2202b, 2202c, and 2202d together at step 2304 for detecting an action of the right hip joint with a software or hardware joint-action detector implemented in embedded controller 2214. For example, if significant reflected infrared-light intensity is detected only when infrared LEDs 2202c and 2202d on the right side of the midline of active infrared proximity sensor 2004 are used as the infrared-light sources, the user's right thigh (i.e. user's body target 2100) must be deviated to the right side of the midline of active infrared proximity sensor 2004 (infrared proximity sensor 2200 is at the midline of active infrared proximity sensor 2004) when the right hip joint is abducted, as illustrated in FIG. 22. On the other hand, if significant reflected infrared-light intensity is detected only when infrared LEDs 2202a and 2202b on the left side of the midline of active infrared proximity sensor 2004 are used as the infrared-light sources, the user's right thigh must be deviated to the left side of the midline of active infrared proximity sensor 2004 when the right hip joint is adducted (not illustrated in FIG. 22).

In order for infrared proximity sensor 2200 of active infrared proximity sensor 2004 to sense any reflected infrared light from the right thigh, the right hip joint has to be at least slightly flexed to bring the right thigh into the line of sight of active infrared proximity sensor 2004. Also, when wearable joint-action sensor 2000 is worn on the right waist above the right thigh, the line of sight of active infrared proximity sensor 2004 (i.e. the midline of active infrared proximity sensor 2004 at infrared proximity sensor 2200) should approximately aim at the midline of the right thigh, where the reflected infrared-light intensity detected by infrared proximity sensor 2200 for infrared light beams emitted from infrared LED 2202a and 2202d (or from infrared LED 2202b and 2202c) are about the same if the right hip joint is at least slightly flexed but not abducted or adducted.

At step 2306, embedded controller 2214 receives acceleration data along the X, Y, and Z axes from triaxial accelerometer 2002, and then embedded controller 2214 processes the data to detect a body action, such as bending of the torso of a user forward, backward, sideways, or in any other direction, with a software or hardware body-action detector implemented in embedded controller 2214. As discussed above, embedded controller 2214 can use data from triaxial accelerometer 2002 for joint-action detection indirectly when the user is standing or when the right hip joint is extended, abducted, or adducted. Embedded controller 2214 combines the reflected infrared-light-intensity data for one or more infrared LEDs that produce significant reflected infrared-light intensities (such as infrared LEDs 2202c and 2202d in FIG. 22) to estimate separation 2201 between active infrared proximity sensor 2004 and user's body target 2100 (i.e. the right thigh in this embodiment), and the very low reflected infrared-light intensities of the other infrared LEDs (i.e. infrared LEDs 2202a and 2202b in FIG. 22) are not used for the estimation. As discussed above, embedded controller 2214 uses the reflected infrared-light-intensity data for all four LEDs to estimate the amount of right or left deviation of the right thigh from the midline of active infrared proximity sensor 2004.

At step 2308, embedded controller 2214 uses the joint-action data obtained from step 2304 and the body-action data obtained from step 2306 to detect a type of physical activity, such as jumping, somersaulting, dancing, sitting up, pushing up, or biking, with a software or hardware physical-activity detector implemented in embedded controller 2214. For example, when a user is doing push-ups, the user's abdomen is facing the floor or ground, and embedded controller 2214 can detect push-up activity by combining acceleration data received from triaxial accelerometer 2002 along the Y axis (which varies around G) and along the X and Z axes (which varies around very small fractions of G, because X and Z axes are almost orthogonal to the earth's gravitational acceleration G), and the very low reflected infrared-light intensities for infrared LEDs 2202a, 2202b, 2202c, and 2202d, because the degree of flexion of the right hip joint is small during push-ups. The number of push-ups performed by the user is equal to the number of peaks or valleys of the acceleration along the Y axis. An additional active infrared proximity sensor 2004 for proximity sensing along the Y axis can be incorporated in wearable joint-action sensor 2000 for sensing the periodic variation of the separation between housing 2001 and the floor or ground when the user is doing push-ups (not illustrated in any figure here) to further confirm the push-up activity. This additional active infrared proximity sensor 2004 is particularly important for detecting push-up activity if triaxial accelerometer 2002 is not incorporated in wearable joint-action sensor 2000. As discussed below, an altimeter (i.e. barometer) with a high resolution can also be used for sensing the ups-and-downs of the waist during push-ups to confirm the push-up activity. Embedded controller 2214 can also detect sit-up activity based on the variation of the degree of flexion of the right hip joint and the large variation of the Z-axis acceleration between approximately zero (when the torso is horizontal) and −G (when the torso is upright). Similarly, embedded controller 2214 can detect biking from the forward-inclined or upright torso of a user and the cyclic variation of the degree of flexion of the right hip joint of the user.

At step 2310, the joint-action data obtained from step 2304, as well as the physical-activity data obtained from step 2308, is stored in the memory of embedded controller 2214. The body-action data obtained from step 2306 can also be stored in the memory of embedded controller 2214 at step 2310 if necessary. At step 2312, embedded controller 2214 reads signals 2224 and 2226 from push buttons 2222a and 2222b, respectively, to find out at steps 2314 and 2316 if the user wants to control the operation of embedded controller 2214, such as to stop data acquisition for joint-action and physical-activity detections, to display data, or to communicate with a computing device, such as a smartwatch, fitness wristband, smartphone, or computer. Under computer program control, embedded controller 2214 can also stop the data acquisition for joint-action and physical-activity detections, display data, or communicate with a computing device, without requiring the user to use push button 2222a or 2222b.

If the data acquisition is not stopped at step 2314 under computer program control, embedded controller 2214 waits for a predetermined time interval at step 2320 before it returns to step 2304 to receive more reflected infrared-light-intensity data from active infrared proximity sensor 2004. On the other hand, if the data acquisition is stopped at step 2314 under computer program control (such as when a predetermined joint action, a predetermined physical activity, or a specific pattern of signals 2224 and 2226 from push buttons 2222a and 2222b, respectively, is detected), embedded controller 2214 can end all the processes shown in FIG. 23 at step 2316. It can also go to step 2318 to display any data or detection result stored in the memory of embedded controller 2214 by using display 2228 or communicate with a computing device by using communication device 2234. If embedded controller 2214 does not end all the processes shown in FIG. 23 at step 2316, embedded controller 2214 returns to step 2304 to receive more reflected infrared-light-intensity data from active infrared proximity sensor 2004 after displaying data or communicating with a computing device at step 2318.

FIG. 23 can also be the flow diagram for illustrating the joint-action and physical-activity detection operations if a time-of-flight proximity sensor, which is an advanced active infrared proximity sensor, is used in the eighth embodiment instead of active infrared proximity sensor 2004. In this case, infrared LEDs 2202a, 2202b, 2202c, and 2202d in FIG. 22 are replaced with infrared laser diodes, and infrared proximity sensor 2200 is replaced with a time-of-flight detector that measures the time light takes to travel from each laser diode to user's body target 2100 and reflect back to the time-of-flight detector to determine the range, such as the distance travelled by infrared-light beams 2210 or 2212. Based on the geometry of the isosceles triangle formed by the equal distances travelled by the emitted and reflected infrared-light beams (such as the equal distances travelled by infrared-light beams 2210 and 2212), and the known distance between the infrared laser diode (that emits the infrared-light beam) and the time-of-flight detector, the height of the isosceles triangle, which is separation 2201 between the time-of-flight proximity sensor and user's body target 2100, can be detected. If only one infrared laser diode is used in active infrared proximity sensor 2004 for sensing just separation 2201 between the time-of-flight proximity sensor and user's body target 2100, the infrared laser diode can be very close to the time-of-flight detector (that detects the range based on the infrared-light travelling time), so that the range obtained from the time-of-flight proximity sensor is approximately equal to separation 2201 between the time-of-flight proximity sensor and user's body target 2100.

Since a time-of-flight proximity sensor measures the infrared-light travelling time, but not the reflected infrared-light intensity, it can measure separation 2201 between the time-of-flight proximity sensor and user's body target 2100 accurately even when an emitted infrared-light beam, such as infrared-light beam 2210, reaches an edge of user's body target 2100, so long as the reflected infrared-light intensity is adequate for the time-of-flight detector to function properly. When the emitted infrared-light beam misses user's body target 2100 entirely, the next closest target, such as the floor or ground, reflects the emitted infrared-light beam instead, and the time-of-flight detector could detect that the next closest target is out of its maximum detection range if the reflected infrared-light intensity is too low for it to function properly. For this reason, a time-of-flight proximity sensor can locate an edge of user's body target 2100 more accurately than a conventional active infrared proximity sensor, which would sense a gradual change in reflected infrared-light intensity that represents a gradual change in the separation between the conventional active infrared proximity sensor and user's body target 2100 when an emitted infrared-light beam reaches an edge of user's body target 2100.

Instead of using a single time-of-flight detector and multiple infrared laser diodes to implement an advanced active infrared proximity sensor similar to the one illustrated in FIG. 22, one or more time-of-flight proximity sensor modules, each including a time-of-flight detector and an infrared laser diode, such as the VL6180X module available from STMicroelectronics of Switzerland, can be used to measure separation 2201 between each time-of-flight proximity sensor module and user's body target 2100. Multiple time-of-flight proximity sensor modules, with one module activated at a time, can be arranged in an array of one or two dimensions or in any special pattern for detecting the location of user's body target 2100 with respect to the time-of-flight proximity sensor modules.

Although a user of wearable joint-action sensor 2000 is typically a human being, a user can be a four-limbed animal, such as a monkey, dog, cat, goose, or elephant, for which joint actions and physical activities are being detected by using the same joint-action and physical-activity detection principles as disclosed in the eighth embodiment. Furthermore, the description of the eighth embodiment above is not intended to limit the invention to the eighth embodiment, but rather to enable any person skilled in the art to make and use the invention. For example, capacitive proximity sensor 102 (in FIG. 1) can replace active infrared proximity sensor 2004 in the eighth embodiment, and active infrared proximity sensor 2004 can replace capacitive proximity sensor 102 in the other embodiments, without departing from the spirit and the scope of the embodiments. Furthermore, when the ambient infrared-light intensity is adequate, such as when wearable joint-action sensor 2000 is worn by a user under the sun, active infrared proximity sensor 2004 can use sunlight instead of any of the infrared LEDs as the infrared light source, and use infrared proximity sensor 2200 to detect any change in the separation between infrared proximity sensor 2200 and the right thigh (i.e. to detect the relative motion between the right thigh and infrared proximity sensor 2200). In this case, a one- or two-dimensional visible- or infrared-light imaging sensor instead of active infrared proximity sensor 2004 can be incorporated in wearable joint-action sensor 2000 for sensing motion of the right thigh to detect actions of the right hip joint.

Alternate Sensor Combinations in the First and Eighth Embodiments

FIGS. 1, 3A, 3B, 4A, 4B, 20A, 20B, 21A, 21B, and 22

Both the first and eighth embodiments are used for detecting actions of the right hip joint (or the left hip joint by using the same detection principle) and physical activities of a user. In the first or eighth embodiment, wearable joint-action sensor 100 or 2000, respectively, is worn on the waist of the torso of the user (the torso is the first body segment in the first or eighth embodiment) above the right thigh of the right upper leg (the right upper leg is the second body segment in the first or eighth embodiment). In the first embodiment (in FIGS. 1, 3A, 3B, 4A, and 4B), capacitive proximity sensor 102 is used for detecting separation 130 between sensing pad 108 on sensing plate 118 and the right abdomen of the torso (the first body segment), while in the eighth embodiment (FIGS. 20A, 20B, 21A, 21B, and 22), active infrared proximity sensor 2004 is used for detecting separation 2201 between active infrared proximity 2004 and the right thigh of the right upper leg (the second body segment) instead.

Although triaxial accelerometer 2002 is incorporated in wearable joint-action sensor 2000, triaxial accelerometer 2002 can also be incorporated in wearable joint-action sensor 100 for detecting body actions of the user by using the same detection principle. The three sensors in the first and eighth embodiments, capacitive proximity sensor 102, active infrared proximity sensor 2004, and triaxial accelerometer 2002, can be combined in any form (i.e. by using any one, two, or all three of the sensors) in any embodiment, not just in the first or eighth embodiment, to function synergistically (when more than one of the three sensors are used) to create a new embodiment. Furthermore, another sensor, such as an ultrasonic proximity sensor, single-chip radar, visible- or infrared-light imaging sensor (a two-dimensional imaging sensor or one-dimensional line-scan imaging sensor), altimeter (i.e. barometer), or gyroscope, can also be used to cooperate with any one, two, or all of the three sensors for joint-action and physical-activity detections in the first or eighth embodiment, or in any embodiment.

For example, when active infrared proximity sensor 2004 of wearable joint-action sensor 2000 is replaced by capacitive proximity sensor 102, push buttons 2222a and 2222b can also be replaced by capacitive touch keys 134 and 136 (in FIG. 1). One or more proximity sensing plates can be placed at the bottom of housing 2001 of wearable joint-action sensor 2000 to replace active infrared proximity sensor 2004 and its overlay 2006 (in FIGS. 20A and 20B). One or more proximity sensing plates can also be placed at the front of housing 2001 that faces the right abdomen of a user, similar to the arrangement in the first embodiment, so that embedded controller 2214 can detect flexion, extension, abduction, and adduction of the right hip joint directly.

When capacitive proximity sensor 102 or active infrared proximity sensor 2004 is used as a simple sitting and standing sensor (in FIGS. 3A, 4A, 20A, and 21A), wearable joint-action sensor 2000 can use data received from triaxial accelerometer 2002 for counting steps only when a user is not sitting or standing, so that wearable joint-action sensor 2000 does not count steps mistakenly when the waist of a user just vibrates, such as when the user is sitting or standing in a travelling vehicle. Furthermore, a high-resolution altimeter (low-resolution barometers have been incorporated in prior-art activity trackers for sensing climbing a flight of stairs, etc.), such as a digital output barometer that is available from STMicroelectronics of Switzerland (Product Number: LPS22HB), can be added to confirm detection of sitting or standing by wearable joint-action sensor 2000 as follows. A large increase in the degree of flexion of the right hip joint (sensed by active infrared proximity sensor 2004) in combination with a rapid decrease in altitude of at least 30 cm (sensed by an altimeter), for example, is strong evidence that a user changes from standing to sitting. On the other hand, a large decrease in the degree of flexion of the right hip joint in combination with a rapid increase in altitude of at least a 30 cm, for example, is strong evidence that a user changes from sitting to standing. If a user changes from standing to sitting or from sitting to standing rapidly, the acceleration along the Z-axis sensed by triaxial accelerometer 2002 can also be used for confirming detection of sitting or standing. This example illustrates some of the benefits of using multiple sensors that work synergistically in wearable joint-action sensor 2000 to improve accuracy of joint-action and physical-activity detections.

Wearable joint-action sensor 2000 can incorporate both capacitive proximity sensor 102 and active infrared proximity sensor 2004 for detecting actions of the right hip joint, because capacitive proximity sensor 102 can sense extension of the right hip joint (in FIG. 4B) directly even through clothing, without relying on detecting the orientation of the torso of a user with triaxial accelerometer 2002, as discussed above. On the other hand, active infrared proximity sensor 2004, especially with a number of infrared LEDs, can directly sense actions (except extension) of the right hip joint, such as flexion, abduction, and adduction, more accurately, because active infrared proximity sensor 2004 can have a longer sensing range than that of capacitive proximity sensor 102, unless the size of sensing plate 118 is large.

When both capacitive proximity sensor 102 and active infrared proximity sensor 2004 are incorporated in wearable joint-action sensor 2000, a software or hardware physical-activity detector in embedded controller 2214 can use a first joint-action detector with data obtained from capacitive proximity sensor 102 to detect flexion and extension of the right hip joint, and use a second joint-action detector with data obtained from active infrared proximity sensor 2004 to detect abduction and adduction, which cannot be reliably detected by the first joint-action detector with data obtained from capacitive proximity sensor 102 using one sensing plate 118. The physical-activity detector in embedded controller 2214 can use the second joint-action detector with data obtained from active infrared proximity sensor 2004 and a body-action detector with data obtained from triaxial accelerometer 2002 to detect standing, as discussed above. When the physical-activity detector detects standing (i.e. when the right hip joint is not flexed or extended) by using the second joint-action detector and the body-action detector, the first joint-action detector can be calibrated to distinguish between flexion and extension of the right hip joint by storing the corresponding capacitance data obtained from capacitive proximity sensor 102 as the reference. After the calibration process, the physical-activity detector can use the first joint-action detector with data obtained from capacitive proximity sensor 102 to detect walking, running, standing, and sitting, because capacitive proximity sensor 102 tends to consume less power than active infrared proximity sensor 2004, as discussed above. At any time when the physical-activity detector detects standing by using the second joint-action detector and the body-action detector, the calibration process can be repeated. Furthermore, the physical-activity detector can use the second joint-action detector with data obtained from active infrared proximity sensor 2004 (instead of the first joint-action detector with data obtained from capacitive proximity sensor 102) to detect a physical activity, such as dancing activity (discussed above), that cannot be detected as reliably by using the first joint-action detector with data obtained from capacitive proximity sensor 102.

Although body actions can also be detected by using proximity sensors instead of triaxial accelerometer 2002, such as by placing sensing plate 118 of capacitive proximity sensor 102 in the proximity of the upper spinal column of a user for detecting flexion and extension of the upper spinal column, as discussed in the seventh embodiment, using triaxial accelerometer 2002 on the waist of the torso of a user for detecting body actions of the torso is more convenient in this case, because active infrared proximity sensor 2004 (or capacitive proximity sensor 102) for detecting actions of the right hip joint and triaxial accelerometer 2002 can both be incorporated in housing 2001 worn on the right waist. When necessary, triaxial accelerometer 2002 can be worn on a different body segment of the user, such as on the head, for detecting body actions of the body segment, and acceleration data from triaxial accelerometer 2002 can be sent to wearable joint-action sensor 2000 worn on the right waist by wired or wireless communication. Depending on the types of body action to be detected, a one-axis, two-axis, or three-axis (triaxial) accelerometer can be used in any embodiment to detect body actions of a body segment of the user, such as the wrist region of the right forearm (the third embodiment) or a finger segment (the sixth embodiment). Furthermore, if necessary, a gyroscope can be used to detect rotation of the body segment, which is a type of movement of the body segment. Types of physical activity can then be detected by combining joint-action data with body-action data.

There is a significant benefit for wearable joint-action sensor 2000 to incorporate any two or all three of active infrared proximity sensor 2004, capacitive proximity sensor 102, and triaxial accelerometer 2002 for detecting actions of the right hip joint. As discussed above, each of the three sensors has its own advantages and disadvantages in detecting actions of the right hip joint, so they can calibrate against each other when they are incorporated in wearable joint-action sensor 2000. For example, when a user is ambulating, a software or hardware physical-activity detector in embedded controller 2214 of wearable joint-action sensor 2000 can use triaxial accelerometer 2002 to detect ambulation, and then use the capacitance waveform obtained from capacitive proximity sensor 102 to determine a capacitance threshold for detecting significant flexion of the right hip joint, where significant flexion is any degree of flexion that is larger than the minimum degree of flexion of the right hip joint required for the user to take an ambulating step forward with the right leg, as discussed above. If the amplitude of the capacitance waveform obtained from capacitive proximity sensor 102 is so small that no capacitance threshold can be reliably determined to differentiate between significant flexion and no significant flexion of the right hip joint, but data from triaxial accelerometer 2002 indicates that the user is ambulating, the user's body must be vibrating instead of ambulating. In this case, the capacitance sensed by capacitive proximity sensor 102 is high if the user is sitting with significant flexion of the right hip joint, and the capacitance is low if the user is standing with no significant flexion of the right hip joint. Similarly, when ambulation is detected by the physical-activity detector using data obtained from triaxial accelerometer 2002, the reflected infrared-light-intensity waveform obtained from active infrared proximity sensor 2004 can be used to determine a reflected infrared-light-intensity threshold for detecting significant flexion of the right hip joint, as discussed above.

Wearable joint-action sensor 2000 can use the capacitance data from capacitive proximity sensor 102 and a capacitance threshold to count steps, as well as to detect sitting (i.e. the right hip joint is in significant flexion for a long duration) and standing (i.e. no significant flexion of the right hip joint for a long duration), especially when combining the body-action data from triaxial accelerometer 2002. For example, if the capacitance sensed by capacitive proximity sensor 102 is constantly high for a long duration (i.e. the duration determined by a timer in embedded controller 2214 exceeds a predetermined duration), indicating that a user is sitting, but the body-action data from triaxial accelerometer 2002 indicates that the user is actually lying on the back, wearable joint-action sensor 2000 with housing 2001 worn on the right waist must be pulled down toward the right abdomen of the torso by the earth's gravitational force when the user is lying on the back, instead of the right abdomen of the torso bulging out toward sensing plate 118 of capacitive proximity sensor 102 (at the front of housing 2001 that faces the right abdomen) as when the user is sitting. Similarly, data from active infrared proximity sensor 2004 and data from triaxial accelerometer 2002 can also be calibrated against each other to optimize detection of actions of the right hip joint.

Active infrared proximity sensor 2004 of wearable joint-action sensor 2000 can also be replaced by a different type of proximity sensor, such as by one or more single-chip radars or by an ultrasonic proximity sensor with one or more ultrasonic transducers. Multiple ultrasonic transducers of an ultrasonic proximity sensor can form a phased array that is similar to that of an ultrasonic imaging sensor for imaging the surface of the right thigh to detect actions of the right hip joint. Similarly, multiple infrared proximity sensors (i.e. more than a single infrared proximity sensor 2200 in FIG. 22) with one or more infrared-light sources can be used for tracking the position of the right thigh. A visible- or infrared-light imaging sensor (or multiple visible- or infrared-light photodiodes arranged in any spatial pattern, such as a line-scan imaging sensor), with or without a light source, can also replace active infrared proximity sensor 2004 for detecting actions of the right hip joint by imaging the surface of the right thigh. For example, deviation of the right thigh from the midline of an imaging sensor can be detected by image processing, and the right thigh appears bigger in an image when it is closer (corresponds to a larger degree of flexion of the right hip joint) to the imaging sensor, and vice versa. Furthermore, an autofocus imaging sensor can detect the separation between the imaging sensor and the right thigh when the right thigh is brought into focus of the imaging sensor. Other imaging processing techniques, such as two-dimensional autocorrelation, can be used for detecting actions of the right hip joint from the infrared- or visible-light video images of the right thigh. When necessary, instead of using embedded controller 2214 to process the video-image data received from a video imaging sensor, embedded controller 2214 can use bus 2232 and communication device 2234 to send all the data, including the data from triaxial accelerometer 2002, to a more powerful computing device for joint-action and physical-activity detection operations. In fact, this technique for reducing the processing burden of the embedded controller in the wearable joint-action sensor can be used in any embodiment when necessary.

By combining data obtained from a wrist-worn device (such as the acceleration data obtained from a smartwatch or a fitness wristband, or the wrist joint-action data obtained from wearable joint-action sensor 100 in the third embodiment) of a user, wearable joint-action sensor 2000 can be used in a physical-activity monitoring system for detecting many types of physical activity, without requiring the user to attach an accelerometer to the thigh. The wrist-worn device is useful in detecting activities involving the upper extremities, while wearable joint-action sensor 2000 worn on the waist can detect activities involving the torso and the thigh of the user. For example, when a user is weightlifting, a wrist-worn device incorporating an accelerometer and wearable joint-action sensor 100 in the third embodiment can detect actions of the wrist joint and the orientation of the wrist region of the forearm with respect to the vertical direction of the earth's gravitational acceleration G, respectively, while wearable joint-action sensor 2000 can detect the orientation of the torso and the degree of flexion of the right hip joint of the user. An altimeter with high resolution can also be incorporated in the wrist-worn device for sensing the ups-and-downs of the wrist during weightlifting, providing additional evidence that the user is weightlifting. U.S. Pat. No. 8,050,881 (2011) to Yeung et al. (the same inventors of the present invention) discloses techniques for synchronization of data collected by a sensor (such as an accelerometer) worn on the wrist with data collected by wearable joint-action sensor 2000 worn on the waist to facilitate detection of the types of physical activity performed by a user.

For example, in a physical-activity monitoring system that employs wearable joint-action sensor 2000 and a wrist-worn device with an accelerometer (such as an accelerometer in a smartwatch or fitness wristband) to detect the types of physical activity performed by a user, display 2228 of wearable joint-action sensor 2000 can give the user a rough estimate of the level of physical activity by showing the step count, total sitting time, total standing time, total dancing time, and total ambulating time. Other types of physical activity can be detected after the data from active infrared proximity sensor 2004, triaxial accelerometer 2002, and the accelerometer in the wrist-worn device, are downloaded (by wired or wireless communication) to a computing device, such as a smartphone or computer, for joint-action detection, body-action detection, and physical-activity detection and display. The step count obtained from wearable joint-action sensor 2000 would be more reliable than the step count that can be obtained from a prior-art pedometer, because wearable joint-action sensor 2000 uses both joint-action data of the right hip joint and body-action data to detect ambulating steps. The computing device can provide the user a detailed breakdown of different types of physical activity performed by the user, so that the user can make appropriate modification to the types and distributions of physical activity for personalized health improvement. Furthermore, the calibrations of active infrared proximity sensor 2004 (or capacitive proximity sensor 102) and triaxial accelerometer 2002 of wearable joint-action sensor 2000 (or wearable joint-action sensor 100) for joint-action and physical-activity detections can be personalized for a user by using machine learning if wearable joint-action sensor 2000 (or wearable joint-action sensor 100) is worn by the same user regularly, so that fast and accurate joint-action and physical-activity detections can be achieved for the user.

Although the description above contains many specificities, these should not be construed as limiting the scope of the embodiments but as merely providing illustrations of some of the embodiments. For example, the above-described embodiments can be modified by one skilled in the art, especially in the combination of various described features, without departing from the spirit and the scope of the embodiments.

Furthermore, the figures in the description above illustrate the architecture, functionality, and operation of possible implementations of the embodiments, and each function specified in the flow diagrams may comprise one or more executable computer program instructions. In some alternative implementations, the functions noted can occur out of the order noted in the flow diagrams, and more or fewer functions in each block, as well as more and fewer blocks, can be used. For example, two blocks shown in succession may be executed substantially concurrently or in the reverse order, depending on the functionality involved. It should also be noted that each block and combination of blocks in the block diagrams and flow diagrams can be implemented by hardware, software (i.e. computer program), or a combination of hardware and software.

Thus the scope of the embodiments should be determined by the appended claims and their legal equivalents, rather than by the examples given.

We claim:

1. A hip joint-action detector comprising:
   (a) a housing adapted to be worn on or in the vicinity of the waist of a user in the proximity of a hip joint of the user;
   (b) a proximity sensor incorporated in said housing and adapted to be in the proximity of a body target linked by said hip joint of the user for obtaining separation data between said housing and said body target through an air gap; and
   (c) a joint-action detector for using said separation data obtained by said proximity sensor to detect at least one joint action of said hip joint of the user.

2. The hip joint-action detector according to claim 1 wherein said proximity sensor is a capacitive proximity sensor.

3. The hip joint-action detector according to claim 2 wherein a sensing plate of said capacitive proximity sensor is incorporated at the front of said housing and adapted to be in the proximity of the lower abdomen of the torso linked by said hip joint of the user, so that said body target is the lower abdomen of the torso linked by said hip joint of the user, and said joint-action detector uses said separation data between the front of said housing and said body target obtained by said capacitive proximity sensor using said sensing plate to detect at least one of flexion or extension of said hip joint of the user.

4. The hip joint-action detector according to claim 2 wherein a sensing plate of said capacitive proximity sensor is incorporated at the front of said housing and adapted to be in the proximity of the buttock of the upper leg that is linked to the torso by said hip joint of the user, so that said body target is the buttock of the upper leg that is linked to the torso by said hip joint of the user, and said joint-action detector uses said separation data between the front of said housing and said body target obtained by said capacitive proximity sensor using said sensing plate to detect at least one of flexion or extension of said hip joint of the user.

5. The hip joint-action detector according to claim 2 wherein a sensing plate of said capacitive proximity sensor is incorporated at the bottom of said housing and adapted to be in the proximity of the thigh of the upper leg that is linked to the torso by said hip joint of the user, so that said body target is the thigh of the upper leg that is linked to the torso by said hip joint of the user, and said joint-action detector uses said separation data between the bottom of said housing and said body target obtained by said capacitive proximity sensor using said sensing plate to detect flexion of said hip joint of the user.

6. The hip joint-action detector according to claim 2 wherein a sensing plate of said capacitive proximity sensor is incorporated at the bottom of said housing and adapted to be in the proximity of the lower abdomen of the torso linked by said hip joint of the user, so that said body target is the lower abdomen of the torso linked by said hip joint of the user, and said joint-action detector uses said separation data between the bottom of said housing and said body target obtained by said capacitive proximity sensor using said sensing plate to detect at least one of flexion or extension of said hip joint of the user.

7. The hip joint-action detector according to claim 2 wherein sensing plates of said capacitive proximity sensor comprises a front sensing plate incorporated at the front of said housing and adapted to be in the proximity of the lower abdomen of the torso linked by said hip joint of the user, and a bottom sensing plate incorporated at the bottom of said housing and adapted to be in the proximity of the lower abdomen of the torso linked by said hip joint of the user, so that said body target is the lower abdomen of the torso linked by said hip joint of the user, and said joint-action detector uses said separation data between the front of said housing and said body target obtained by said capacitive proximity sensor using said front sensing plate and/or between the bottom of said housing and said body target obtained by said capacitive proximity sensor using said bottom sensing plate to detect at least one of flexion or extension of said hip joint of the user.

8. The hip joint-action detector according to claim 3 wherein said joint-action detector uses a capacitance threshold for said separation data to detect at least one of flexion or extension of said hip joint of the user.

9. The hip joint-action detector according to claim 2 wherein a plurality of sensing plates of said capacitive proximity sensor are incorporated at the front of said housing and adapted to be in the proximity of the lower abdomen of the torso linked by said hip joint of the user, so that said body target is the lower abdomen of the torso linked by said hip joint of the user, and said joint-action detector uses said separation data between the front of said housing and said body target obtained by said capacitive proximity sensor using said plurality of sensing plates to detect at least one of flexion, extension, abduction, adduction, flexion combined with abduction, flexion combined with adduction, extension combined with abduction, or extension combined with adduction of said hip joint of the user.

10. The hip joint-action detector according to claim 3 further comprises:
(a) an accelerometer in said housing for obtaining acceleration data of the waist of the torso of the user; and
(b) a physical-activity detector for using said separation data obtained by said capacitive proximity sensor and said acceleration data obtained by said accelerometer to detect at least one physical activity of the user.

11. The hip joint-action detector according to claim 3 further comprises:
(a) an active infrared proximity sensor incorporated at the bottom of said housing and adapted to be in the proximity of the thigh of the upper leg that is linked to the torso by said hip joint of the user for obtaining bottom separation data between the bottom of said housing and the thigh of the upper leg that is linked to the torso by said hip joint of the user; and (b) an infrared joint-action detector for using said bottom separation data obtained by said active infrared proximity sensor to detect at least one of abduction or adduction of said hip joint of the user.

12. The hip joint-action detector according to claim 1 wherein said proximity sensor is an active infrared proximity sensor.

13. The hip joint-action detector according to claim 12 wherein said active infrared proximity sensor is incorporated at the bottom of said housing and adapted to be in the proximity of the thigh of the upper leg that is linked to the torso by said hip joint of the user, so that said body target is the thigh of the upper leg that is linked to the torso by said hip joint of the user, and said joint-action detector uses said separation data between the bottom of said housing and said body target obtained by said active infrared proximity sensor to detect flexion of said hip joint of the user.

14. The hip joint-action detector according to claim 13 wherein said joint-action detector uses an infrared-light intensity threshold for said separation data to detect flexion of said hip joint of the user.

15. The hip joint-action detector according to claim 12 wherein said active infrared proximity sensor comprising a plurality of infrared LEDs is incorporated at the bottom of said housing and adapted to be in the proximity of the thigh of the upper leg that is linked to the torso by said hip joint of the user, so that said body target is the thigh of the upper leg that is linked to the torso by said hip joint of the user, and said joint-action detector uses said separation data between the bottom of said housing and said body target obtained by said active infrared proximity sensor using said plurality of infrared LEDs to detect at least one of flexion, abduction, adduction, flexion combined with abduction, or flexion combined with adduction of said hip joint of the user.

16. The hip joint-action detector according to claim 1 wherein said proximity sensor is an imaging sensor incorporated at the bottom of said housing and adapted to be in the proximity of the thigh of the upper leg that is linked to the torso by said hip joint of the user, so that said body target is the thigh of the upper leg that is linked to the torso by said hip joint of the user, and said joint-action detector uses said separation data between the bottom of said housing and said body target obtained by said imaging sensor to detect at least one of flexion, abduction, adduction, flexion combined with abduction, or flexion combined with adduction of said hip joint of the user.

17. A hip joint-action detector comprising:
(a) a housing adapted to be worn on or in the vicinity of the waist in the proximity of a hip joint of a user;
(b) a capacitive proximity sensor;
(c) a front sensing plate, which is electrically connected to a front-sensing channel of said capacitive proximity sensor, incorporated at the front of said housing and adapted to be in the proximity of the lower abdomen of the torso linked by said hip joint of the user for obtaining front separation data between the front of said housing and the lower abdomen of the torso linked by said hip joint of the user; and
(d) a front detection means for using said front separation data obtained by said capacitive proximity sensor using said front sensing plate to detect sitting of the user.

18. The hip joint-action detector according to claim 17 further comprises:
(a) a bottom sensing plate, which is electrically connected to a bottom-sensing channel of said capacitive proximity sensor, incorporated at the bottom of said housing and adapted to be in the proximity of the lower abdomen of the torso linked by said hip joint of the user for obtaining bottom separation data between the bottom of said housing and the lower abdomen of the torso linked by said hip joint of the user; and (b) a sitting detection means for using said front separation data obtained by said capacitive proximity sensor using said front sensing plate and/or said bottom separation data obtained by said capacitive proximity sensor using said bottom sensing plate to detect sitting of the user.

19. The hip joint-action detector according to claim 17 further comprises a bottom sensing plate, which is electrically connected to said front sensing plate, incorporated at the bottom of said housing and adapted to be in the proximity of the lower abdomen of the torso linked by said hip joint of the user, whereby said front sensing plate incorporated at the front of said housing further comprises said bottom sensing plate incorporated at the bottom of said housing.

20. A hip joint-action detector comprising:
(a) a housing adapted to be worn on or in the vicinity of the waist in the proximity of a hip joint of a user;
(b) a proximity sensor incorporated at the bottom of said housing and adapted to be in the proximity of a body target, which is the lower abdomen of the torso linked by said hip joint of the user or the thigh of the upper leg that is linked to the torso by said hip joint of the user, for obtaining separation data between the bottom of said housing and said body target through an air gap; and (c) a detection means for using said separation data obtained by said proximity sensor to detect sitting of the user.

21. A hip joint-action detector adapted to be worn on or in the vicinity of the waist of a user in the proximity of a hip joint of the user, comprising:
(a) a proximity sensor adapted to be in the proximity of a body target linked by said hip joint of the user for obtaining separation data between said proximity sensor and said body target through an air gap; and
(b) a joint-action detector for using said separation data obtained by said proximity sensor to detect at least one joint action of said hip joint of the user.

22. The hip joint-action detector according to claim 21 wherein said proximity sensor is a capacitive proximity sensor.

23. The hip joint-action detector according to claim 21 wherein said proximity sensor is an active infrared proximity sensor.

24. The hip joint-action detector according to claim 21 wherein said proximity sensor is an imaging sensor.

25. The hip joint-action detector according to claim 21 further comprises:
(a) an accelerometer for obtaining acceleration data of the waist of the torso of the user; and
(b) a physical-activity detector for using said separation data obtained by said capacitive proximity sensor and said acceleration data obtained by said accelerometer to detect at least one physical activity of the user.

* * * * *